United States Patent [19]
Tan et al.

[11] Patent Number: 6,001,361
[45] Date of Patent: Dec. 14, 1999

[54] MYCOBACTERIUM VACCAE ANTIGENS

[75] Inventors: Paul Tan, Parnell; Jun Hiyama, Grey Lynn; Elizabeth Visser, Blockhouse Bay; Margot Skinner, Westmere; Linda Scott, Roslyn; Ross Prestidge, Creemars Bay, all of New Zealand

[73] Assignee: Genesis Research & Development Corporation Limited, Parnell, New Zealand

[21] Appl. No.: 08/873,970

[22] Filed: Jun. 12, 1997

Related U.S. Application Data

[63] Continuation-in-part of application No. 08/705,347, Aug. 29, 1996.

[51] Int. Cl.⁶ .......................... A61K 39/04; C07K 14/35; C07K 7/00
[52] U.S. Cl. ..................... 424/190.1; 424/184.1; 424/248.1; 424/234.1; 424/278.1; 530/300; 530/324; 530/325; 530/326; 530/327; 530/328; 530/329; 530/350
[58] Field of Search .................. 530/300, 350, 530/324, 325, 326, 327, 328, 329; 424/184.1, 248.1, 190.1, 234.1, 278.1

[56] References Cited

U.S. PATENT DOCUMENTS

| | | |
|---|---|---|
| 3,956,481 | 5/1976 | Jolles et al. . |
| 4,036,953 | 7/1977 | Adam et al. . |
| 4,716,038 | 12/1987 | Stanford et al. . |
| 4,724,144 | 2/1988 | Rook et al. . |
| 4,879,213 | 11/1989 | Fox et al. . |
| 5,599,545 | 2/1997 | Stanford et al. . |

FOREIGN PATENT DOCUMENTS

| | | |
|---|---|---|
| 0763361 | 3/1997 | European Pat. Off. . |
| 9002564 | 3/1990 | WIPO . |
| 9007935 | 7/1990 | WIPO . |
| 9101751 | 2/1991 | WIPO . |
| 9102542 | 3/1991 | WIPO . |
| 9208484 | 5/1992 | WIPO . |
| 9208488 | 5/1992 | WIPO . |
| 9316727 | 9/1993 | WIPO . |
| 9406466 | 3/1994 | WIPO . |
| 9514713 | 6/1995 | WIPO . |
| 9525744 | 9/1995 | WIPO . |
| 9526742 | 10/1995 | WIPO . |

OTHER PUBLICATIONS

Wiker et al. Injection & Immunity 1990 vol. 58, No. 1, 272–274.
Burgess et al. J. Cell Biol. 1990 vol. 111, 2129–2138.
Lazen et al. Mol. Cell. Biol. 1988 vol. 8, No. 3, 1247–1252.
Skinner, Immunization with Heat–Killed Mycobacterium vaccae Stimulates CD8⁺ Cytotoxic T Cells Specific for Macrophages Infected with *Mycobacterium tuberculosis, Infection and Immunity* 65:11,4525–4530, 1997.
R.G. White et al., "Correlation of Adjuvant Activity and Chemical Structure of Wax D Fractions of Mycobacteria," Immunology 7, pp. 158–171, 1964.
R.G. White, "Characterization of Micobacterial Components of Adjuvant Mixtures," Symposium Series Immunobiol. Standard 6, pp. 49–58, 1967.
R.G. White et al., The Influence of Components of M. Tuberculosis and other Mycobacteria upon Antibody Production to Ovalbumin, Immunology I, pp. 54–66, 1958.

*Primary Examiner*—Anthony C. Caputa
*Assistant Examiner*—Heather A. Bakalyar
*Attorney, Agent, or Firm*—Janet Sleath; Ann W. Speckman

[57] ABSTRACT

The present invention provides polypeptides comprising an immunogenic portion of a *M. vaccae* soluble protein and DNA molecules encoding such polypeptides, together with methods for their use in the diagnosis and treatment of mycobacterial infection. Methods for enhancing the immune response to an antigen including administration of *M. vaccae* culture filtrate or delipidated *M. vaccae* cells are also provided.

6 Claims, 11 Drawing Sheets

```
M. vaccae:  MRLLDRIRGPW...ARRFGVV.AVATAMMPALVGLAGGSATAGAFSRPGLPVEYLMVPSP
m. bovis:   MQLVDRVRGAVTGMSRRL.VVGAVGAALVSGLVGAVGGTATAGAFSRPGLPVEYLQVPSP
M. tb:      MQLVDRVRGAVTGMSRRL.VVGAVAR.LVSGLVGAVGGTATAGAFSRPGLPVEYLQVPSP
m. leprae.  MKFVDRFRGAVAGMLRRL.VVEAMGVALLSALIGVVG.SAPAEAFSRPGLPVEYLQVPSP
CONSENSUS:  M   DR RG      RR  VV A         L G  G    A A AFSRPGLPVEYL VPSP M. vaccae:  SMGRDIKIQFQSGGENSPALYLLDGLRAQEDFNGWDINTQAFEWFLDSGISVVMPVGGQS
m. bovis:   SMGRDIKVQFQSGGANSPALYLLDGLRAQDDFSGWDINTPAFEWYDQSGLSVVMPVGGQS
M. tb:      SMGRDIKVQFQSGGANSPALYLLDGLRAQDDFSGWDINTPAFEWYDQSGLSVVMPVGGQS
M. leprae:  SMGRDIKVQFQNGGANSPALYLLDGLRAQDDFSGWDINTTAFEWYYQSGISVVMPVGGQS
CONSENSUS:  SMGRDIK QFQ GG NSPALYLLDGLRA   F GWDINT AFEW   SG SVVMPVGGQS M. vaccae:  SFYTDWYAPARNKGPTVTYKWETFLTQELPGWLQANRAVKPTGSGPVGLSMAGSAALNLA
M. bovis:   SFYSDWYQPACGKAGCQTYKWETFLTSELPGWLQANRHVKPTGSAVVGLSMAASSALTLA
M. tb:      SFYSDWYQPACRKAGCQTYKWETFLTSELPGWLQANRHVKPTGSAVVGLSMAASSALTLA
M. leprae:  SFYSDWYSPACGKAGCQTYKWETFLTSELPEYLQSNKQIKPTGSAAVGLSMAGLSALTLA
CONSENSUS:  SFY DWY PA  K      TYKWETFLT ELP   LQ N   KPTGS  VGLSMA    AL LA M. vaccae:  TWHPEQFIYAGSMSGFLNPSEGWWPFLINISMGDAGGFKADDMWGKTEGIPTAVGQRNDP
M. bovis:   IYHPQQFVYAGAMSGLLDPSQAMGPTLIGLAMGDAGGYKASDMWGPKEDPAW...QRNDP
M. tb:      IYHPQQFVYAGAMSGLLDPSQAMGPTLIGLAMGDAGGYKASDMWGPKEDPAW...QRNDP
M. leprae:  IYHPDQFIYVGSMSGLLDPSNAMGPSLIGLAMGDAGGYKAADMWGPSTDPAW...KRNDP
CONSENSUS:    HP QF Y G MSG L PS    P LI  MGDAGG KA DMWG          RNDP M. vaccae:  MLNIPTLVANNTRIWVYCGNGQPTELGGGDLPATFLEGLTIRT.NETFRDNYIAAGGHNG
m. bovis:   LLNVGKLIANNTRVWVYCGNGKPSDLGGNNLPAKFLEGF.VRTSNIKFQDAYNAGGGHNG
M. tb:      LLNVGKLIANNTRVWVYCGNGKPSDLGGNNLPAKFLEGF.VRTSNIKFQDAYNAGGRHNG
M. leprae:  TVNVGTLIANNTRIWMYCGNGKPTELGGNNLPAKLLEGL.VRTSNIKFQDGYNAGGGHNA
CONSENSUS:      N   L ANNTR W YCGNG P  LGG  LPA  LEG   RT N  F D Y A G HN M. vaccae:  VFNFPANGTHNWAYWGRELQAMKPDLQAHLL*
M. bovis:   VFDFPDSGTHSWEYWGAQLNAMKPDLQRALGATPNTGPAPQGA*
M. tb:      VFDFPDSGTHSWEYWGAQLNAMKPDLQRHWVPRPTPGP.PQGA*
M. leprae:  VFNFPDSGTHSWEYWGEQLNDMKPDLQQYLGAT..PGA*
CONSENSUS:  VF FP  GTH W YWG   L  MKPDLQ
```

*Fig. 3*

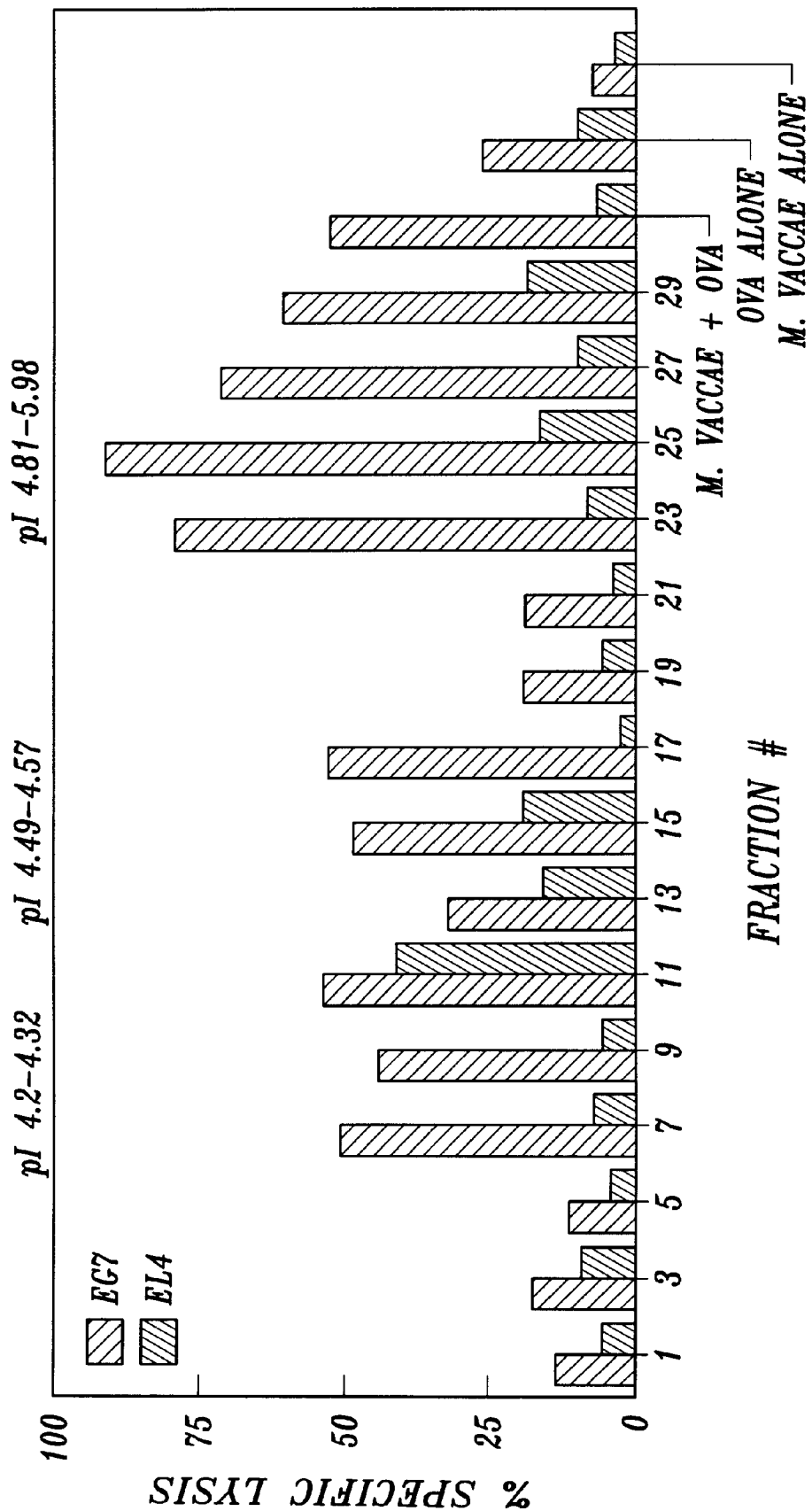

MYCOBACTERIUM VACCAE ANTIGENS

CROSS-REFERENCE TO RELATED APPLICATIONS

This application is a continuation-in-part of U.S. patent application Ser. No. 08/705,347, filed Aug. 29, 1996.

TECHNICAL FIELD

The present invention relates generally to the detection, treatment and prevention of infectious diseases. In particular, the invention is related to compounds and methods for the treatment of mycobacterial infections including *Mycobacterium tuberculosis* and *Mycobacterium avium*. The invention is further related to compounds that function as non-specific immune response amplifiers, and the use of such non-specific immune response amplifiers as adjuvants in vaccination or immunotherapy against infectious disease, and in certain treatments for immune disorders and cancer.

BACKGROUND OF THE INVENTION

Tuberculosis is a chronic, infectious disease, that is caused by infection with *Mycobacterium tuberculosis* (*M. tuberculosis*). It is a major disease in developing countries, as well as an increasing problem in developed areas of the world, with about 8 million new cases and 3 million deaths each year. Although the infection may be asymptomatic for a considerable period of time, the disease is most commonly manifested as a chronic inflammation of the lungs, resulting in fever and respiratory symptoms. If left untreated, significant morbidity and death may result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behaviour is difficult to monitor. Some patients do not complete the course of treatment, which can lead to ineffective treatment and the development of drug resistant mycobacteria.

Inhibiting the spread of tuberculosis requires effective vaccination and accurate, early diagnosis of the disease. Currently, vaccination with live bacteria is the most efficient method for inducing protective immunity. The most common mycobacterium employed for this purpose is Bacillus Calmette-Guerin (BCG), an avirulent strain of *Mycobacterium bovis*. However, the safety and efficacy of BCG is a source of controversy and some countries, such as the United States, do not vaccinate the general public. Diagnosis of *M. tuberculosis* infection is commonly achieved using a skin test, which involves intradermal exposure to tuberculin PPD (protein-purified derivative). Antigen-specific T cell responses result in measurable induration at the injection site by 48–72 hours after injection, thereby indicating exposure to mycobacterial antigens. Sensitivity and specificity have, however, been a problem with this test, and individuals vaccinated with BCG cannot be distinguished from infected individuals.

A less well-known mycobacterium that has been used for immunotherapy for tuberculosis, and also leprosy, is *Mycobacterium vaccae*, which is non-pathogenic in humans. However, there is less information on the efficacy of *M. vaccae* compared with BCG, and it has not been used widely to vaccinate the general public. *M. bovis* BCG and *M. vaccae* are believed to contain antigenic compounds that are recognised by the immune system of individuals exposed to infection with *M. tuberculosis*.

There thus remains a need in the art for effective compounds and methods for preventing, treating and detecting tuberculosis.

SUMMARY OF THE INVENTION

Briefly stated, the present invention provides compounds and methods for the prevention, treatment and diagnosis of mycobacterial infection, together with adjuvants for use in vaccines or immunotherapy of infectious diseases and cancers.

In a first aspect, polypeptides derived from *Mycobacterium vaccae* are provided comprising an immunogenic portion of an antigen, or a variant of such an antigen. In one embodiment, the antigen includes an amino acid sequence selected from the group consisting of sequences recited in SEQ ID NOS: 56–59, 63–65, 101, 103, 105, and variants thereof.

DNA sequences encoding the inventive polypeptides, expression vectors comprising these DNA sequences, and host cells transformed or transfected with such expression vectors are also provided.

In another aspect, the present invention provides fusion proteins comprising a first and a second inventive polypeptide or, alternatively, an inventive polypeptide and a known *M. tuberculosis* antigen.

Within other aspects, the present invention provides pharmaceutical compositions that comprise at least one of the inventive polypeptides, or a DNA molecule encoding such a polypeptide, and a physiologically acceptable carrier. The invention also provides vaccines comprising at least one of the above polypeptides and a non-specific immune response amplifier, together with vaccines comprising at least one DNA sequence encoding such polypeptides and a non-specific immune response amplifier.

In yet another aspect, methods are provided for inducing protective immunity in a patient, comprising administering to a patient an effective amount of one or more of the above polypeptides together with an immune response amplifier.

In further aspects of this invention, methods and diagnostic kits are provided for detecting tuberculosis in a patient. In a first embodiment, the method comprises contacting dermal cells of a patient with one or more of the above polypeptides and detecting an immune response on the patient's skin. In a second embodiment, the method comprises contacting a biological sample with at least one of the above polypeptides; and detecting in the sample the presence of antibodies that bind to the polypeptide or polypeptides, thereby detecting *M. tuberculosis* infection in the biological sample. Suitable biological samples include whole blood, sputum, serum, plasma, saliva, cerebrospinal fluid and urine.

Diagnostic kits comprising one or more of the above polypeptides in combination with an apparatus sufficient to contact the polypeptide with the dermal cells of a patient are provided. The present invention also provides diagnostic kits comprising one or more of the inventive polypeptides in combination with a detection reagent.

In yet another aspect, the present invention provides antibodies, both polyclonal and monoclonal, that bind to the polypeptides described above, as well as methods for their use in the detection of *M. tuberculosis* infection.

The present invention also provides methods for enhancing a non-specific immune response to an antigen. In one embodiment, such methods comprise administering *M. vaccae* culture filtrate or delipidated *M. vaccae* cells. In a second embodiment, such methods comprise administering a polypeptide, the polypeptide comprising an immunogenic portion of an antigen, or a variant thereof, wherein said antigen includes a sequence provided in SEQ ID NO: 78.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 3 is a comparison of the Antigen 85A protein sequence obtained from M. vaccae with those from M. bovis, M. tuberculosis and M. leprae (SEQ ID Nos. 43, 34, 32, 30, respectively).

FIG. 4C(ii) illustrates the non-specific immune amplifying effects of delipidated M. vaccae from which glycolipids had been removed and the proteins extracted with SDS. FIG. 4C(iii) illustrates that the adjuvant effect of the preparation of FIG. 4C(ii) is destroyed by treatment with the proteolytic enzyme pronase.

FIG. 7 illustrates the non-specific immune amplifying effects of different pI fractions of SDS-extracted M. vaccae proteins.

DETAILED DESCRIPTION OF THE INVENTION

Figure 1A:
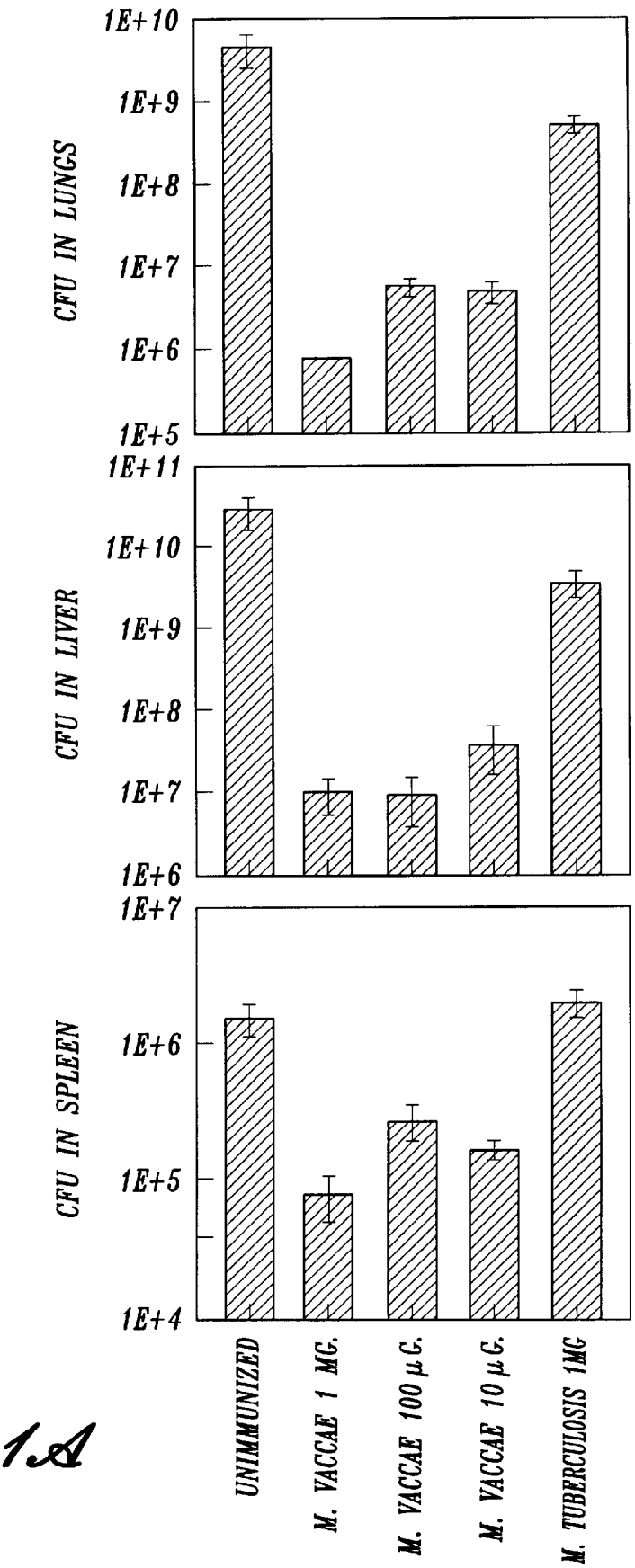
FIGS. 1A and 1B illustrate the protective effects of immunizing mice with autoclaved M. vaccae or unfractionated M. vaccae culture filtrates, respectively, prior to infection with live M. tuberculosis H37Rv.

As noted above, the present invention is generally directed to compositions and methods for preventing, treating and diagnosing mycobacterial infections, including M. tuberculosis and M. avium infections.

Considerable research efforts have been directed towards elucidating the mechanism of immune response to mycobacterial infection, in particular M. tuberculosis infection. While macrophages have been shown to act as the principal effectors of M. tuberculosis immunity, T cells are the predominant inducers of such immunity. The essential role of T cells in protection against M. tuberculosis infection is illustrated by the frequent occurrence of M. tuberculosis in AIDS patients, due to the depletion of CD4 T cells associated with human immunodeficiency virus (HIV) infection. Mycobacterium-reactive CD4 T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit M. tuberculosis infection. Furthermore, it is known that IFN-γ stimulates human macrophages to make 1,25-dihydroxy-vitamin D3. Similarly, IL-12 has been shown to play a role in stimulating resistance to M. tuberculosis infection. Another property of CD4$^+$ T cells and macrophages is their ability to activate CD8$^+$ cytotoxic T cells which are capable of killing pathogen-infected cells. CD8$^+$ T cells have been shown to kill macrophages and other cells that harbour M. tuberculosis. For a review of the immunology of M. tuberculosis infection see Chan and Kaufmann in Tuberculosis: Pathogenesis, Protection and Control, Bloom (ed.), ASM Press, Washington, DC, 1994.

The compositions of the present invention include polypeptides that comprise at least one immunogenic portion of a soluble M. vaccae antigen, or a variant thereof. Such polypeptides stimulate T cell proliferation, and/or, interferon gamma secretion from T cells of individuals exposed to M. tuberculosis. A "soluble M. vaccae antigen" is a protein of M. vaccae origin that is present in M. vaccae culture filtrate. As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native M. vaccae antigen or may be heterologous, and such sequences may (but need not) be immunogenic.

"Immunogenic," as used herein, refers to the ability to elicit an immune response in a patient, such as a human, or in a biological sample. In particular, immunogenic antigens are capable of stimulating cell proliferation, interleukin-12 production or interferon-γ production in biological samples comprising one or more cells selected from the group of T cells, NK cells, B cells and macrophages, where the cells are derived from an M. tuberculosis-immune individual. Polypeptides comprising at least an immunogenic portion of one or more M. vaccae antigens may generally be used to detect tuberculosis or to induce protective immunity against tuberculosis in a patient.

The compositions and methods of this invention also encompass variants of the above polypeptides. As used herein, the term "variant" covers any sequence which has at least about a 99% probability of being the same as the inventive sequence. The probability for DNA sequences is measured by FASTA (version 2.0u4, February 1996; Pearson W. R. et al., Proc. Natl. Acad. Sci., 85:2444–2448, 1988), the probability for translated DNA sequences is measured by TBLASTX and that for protein sequences is measured by BLASTP (Altschul, S. F. et al. J. Mol. Biol., 215:403–410, 1990). The term "variants" thus encompasses sequences wherein the probability of finding a match by chance (smallest sum probability), is less than about 1% as measured by any of the above tests.

A polypeptide of the present invention may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In general, *M. vaccae* antigens, and DNA sequences encoding such antigens, may be prepared using any of a variety of procedures. For example, soluble antigens may be isolated from *M. vaccae* culture filtrate as described below. Antigens may also be produced recombinantly by inserting a DNA sequence that encodes the antigen into an expression vector and expressing the antigen in an appropriate host. Any of a variety of expression vectors known to those of ordinary skill in the art may be employed. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. The DNA sequences expressed in this manner may encode naturally occurring antigens, portions of naturally occurring antigens, or other variants thereof.

DNA sequences encoding *M. vaccae* antigens may be obtained by screening an appropriate *M. vaccae* cDNA or genomic DNA library for DNA sequences that hybridize to degenerate oligonucleotides derived from partial amino acid sequences of isolated soluble antigens. Suitable degenerate oligonucleotides may be designed and synthesized. and the screen may be performed as described, for example in Maniatis et al., *Molecular Cloning. A Laboratory Manual*, Cold Spring Harbor Laboratories, Cold Spring Harbor, N.Y., 1989. As described below, polymerase chain reaction (PCR) may be employed to isolate a nucleic acid probe from a cDNA or genomic DNA library. The library screen may then be performed using the isolated probe.

DNA molecules encoding *M. vaccae* antigens may also be isolated by screening an appropriate *M. vaccae* expression library with anti-sera (e.g., rabbit or monkey) raised specifically against *M. vaccae* antigens.

Regardless of the method of preparation, the antigens described herein have the ability to induce an immunogenic response. More specifically, the antigens have the ability to induce cell proliferation and/or cytokine production (for example, interferon-γ and/or interleukin-12 production) in T cells, NK cells, B cells or macrophages derived from an *M. tuberculosis*-immune individual. An *M. tuberculosis*-immune individual is one who is considered to be resistant to the development of tuberculosis by virtue of having mounted an effective T cell response to *M. tuberculosis*. Such individuals may be identified based on a strongly positive (i.e., greater than about 10 mm diameter induration) intradermal skin test response to tuberculosis proteins (PPD), and an absence of any symptoms of tuberculosis infection.

The selection of cell type for use in evaluating an immunogenic response to an antigen will depend on the desired response. For example, interleukin-12 production is most readily evaluated using preparations containing B cells or macrophages. T cells, NK cells, B cells and macrophages derived from *M. tuberculosis*-immune individuals may be prepared using methods well known in the art. For example, a preparation of peripheral blood mononuclear cells (PBMCs) may be employed without further separation of component cells. PBMCs may be prepared, for example, using density centrifugation through Ficoll™ (Winthrop Laboratories, NY). T cells for use in the assays described herein may be purified directly from PBMCs. Alternatively, an enriched T cell line reactive against mycobacterial proteins, or T cell clones reactive to individual mycobacterial proteins, may be employed. Such T cell clones may be generated by, for example, culturing PBMCs from *M. tuberculosis*-immune individuals with mycobacterial proteins for a period of 2–4 weeks. This allows expansion of only the mycobacterial protein-specific T cells, resulting in a line composed solely of such cells. These cells may then be cloned and tested with individual proteins, using methods well known in the art, to more accurately define individual T cell specificity. Assays for cell proliferation or cytokine production in T cells, NK cells, B cells or macrophages may be performed, for example, using the procedures described below.

In general, immunogenic antigens are those antigens that stimulate proliferation or cytokine production (i.e., interferon-γ and/or interleukin-12 production) in T cells, NK cells, B cells or macrophages derived from at least about 25% of *M. tuberculosis*-immune individuals. Among these immunogenic antigens, polypeptides having superior therapeutic properties may be distinguished based on the magnitude of the responses in the above assays and based on the percentage of individuals for which a response is observed. In addition, antigens having superior therapeutic properties will not stimulate cell proliferation or cytokine production in vitro in cells derived from more than about 25% of individuals that are not *M. tuberculosis*-immune, thereby eliminating responses that are not specifically due to *M. tuberculosis*-responsive cells. Thus, those antigens that induce a response in a high percentage of T cell, NK cell, B cell or macrophage preparations from *M. tuberculosis*-immune individuals (with a low incidence of responses in cell preparations from other individuals) have superior therapeutic properties.

Antigens with superior therapeutic properties may also be identified based on their ability to diminish the severity of *M. tuberculosis* infection, or other mycobacterial infection, in experimental animals, when administered as a vaccine. Suitable vaccine preparations for use in experimental animals are described in detail below.

Antigens having superior diagnostic properties may generally be identified based on the ability to elicit a response in an intradermal skin test performed on an individual with active tuberculosis, but not in a test performed on an individual who is not infected with *M. tuberculosis*. Skin tests may generally be performed as described below, with a response of at least about 5 mm induration considered positive.

Immunogenic portions of the antigens described herein may be prepared and identified using well known techniques, such as those summarized in Paul, *Fundamental Immunology*, 3d ed., Raven Press, 1993, pp. 243–247. Such techniques include screening polypeptide portions of the native antigen for immunogenic properties. The representative proliferation and cytokine production assays described herein may be employed in these screens. An immunogenic portion of a polypeptide is a portion that, within such representative assays, generates an immune response (e.g., cell proliferation, interferon-γ production or interleukin-12 production) that is substantially similar to that generated by the full length antigen. In other words, an immunogenic portion of an antigen may generate at least about 20%, preferably about 65%, and most preferably about 100%, of the proliferation induced by the full length antigen in the model proliferation assay described herein. An immunogenic portion may also, or alternatively, stimulate the production of at least about 20%, preferably about 65% and most preferably about 100%, of the interferon-γ and/or interleukin-12 induced by the full length antigen in the model assay described herein.

Portions and other variants of *M. vaccae* antigens may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems, Inc. (Foster City, Calif.), and may be operated according to the manufacturer's instructions. Variants of a native antigen may be prepared using standard mutagenesis techniques, such as oligonucleotide-directed site-specific mutagenesis. Sections of the DNA sequence may also be removed using standard techniques to permit preparation of truncated polypeptides.

In general, regardless of the method of preparation, the polypeptides disclosed herein are prepared in substantially pure form. Preferably, the polypeptides are at least about 80% pure, more preferably at least about 90% pure and most preferably at least about 99% pure. In certain preferred embodiments, described in detail below, the substantially pure polypeptides are incorporated into pharmaceutical compositions or vaccines for use in one or more of the methods disclosed herein.

The present invention also provides fusion proteins comprising a first and a second inventive polypeptide or, alternatively, a polypeptide of the present invention and a known *M. tuberculosis* antigen, such as the 38 kD antigen described in Andersen and Hansen, *Infect. Immun.* 57:2481–2488, 1989, together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. Peptide linker sequences are not required when the first and second polypeptides have non-essential N-terminal amino acid regions that can be used to separate the functional domains and prevent steric interference.

The ligated DNA sequences encoding the fusion proteins are cloned into suitable expression systems using techniques known to those of ordinary skill in the art.

In another aspect, the present invention provides methods for using one or more of the inventive polypeptides or fusion proteins (or DNA molecules encoding such polypeptides or fusion proteins) to induce protective immunity against tuberculosis in a patient. As used herein, a "patient" refers to any warm-blooded animal, preferably a human. A patient may be afflicted with a disease, or may be free of detectable disease or infection. In other words, protective immunity may be induced to prevent or treat tuberculosis.

In this aspect, the polypeptide, fusion protein or DNA molecule is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response amplifier, such as an adjuvant or a liposome, into which the polypeptide is incorporated. Such pharmaceutical compositions and vaccines may also contain other mycobacterial antigens, either, as discussed above, incorporated into a fusion protein or present within a separate polypeptide.

Alternatively, a vaccine of the present invention may contain DNA encoding one or more polypeptides as described above, such that the polypeptide is generated in situ. In such vaccines, the DNA may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminator signal). Bacterial delivery systems involve the administration of a bacterium (such as Bacillus-Calmette-Guerin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic, or defective, replication competent virus. Techniques for incorporating DNA into such expression systems are well known in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

A DNA vaccine as described above may be administered simultaneously with or sequentially to either a polypeptide of the present invention or a known mycobacterial antigen, such as the 38 kD antigen described above. For example, administration of DNA encoding a polypeptide of the present invention, may be followed by administration of an antigen in order to enhance the protective immune effect of the vaccine.

Routes and frequency of administration, as well as dosage, will vary from individual to individual and may parallel those currently being used in immunization using BCG. In general, the pharmaceutical compositions and vaccines may be administered by injection (e.g., intradermal, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in a patient sufficient to protect the patient from mycobacterial infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 µg. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to non-specifically enhance the immune response. Most adjuvants contain a substance designed to protect the antigen from rapid catabolism, such as aluminum hydroxide or mineral oil, and a non-specific stimulator of immune responses, such as lipid A, *Bordetella pertussis, M. tuberculosis*, or, as discussed below, *M. vaccae*. Suitable adjuvants are commercially available as, for example, Freund's Incomplete Adjuvant and Freund's Complete Adjuvant (Difco Laboratories, Detroit, Mich.), and Merck Adjuvant 65 (Merck and Company, Inc., Rahway, N.J.). Other suitable adjuvants include alum, biodegradable microspheres, monophosphoryl lipid A and Quil A.

In another aspect, this invention provides methods for using one or more of the polypeptides described above to diagnose tuberculosis using a skin test. As used herein, a "skin test" is any assay performed directly on a patient in which a delayed-type hypersensitivity (DTH) reaction (such as swelling, reddening or dermatitis) is measured following intradermal injection of one or more polypeptides as described above. Preferably, the reaction is measured at least 48 hours after injection, more preferably 48–72 hours.

The DTH reaction is a cell-mediated immune response, which is greater in patients that have been exposed previously to the test antigen (i.e., the immunogenic portion of the polypeptide employed, or a variant thereof). The response may be measured visually, using a ruler. In general, a response that is greater than about 0.5 cm in diameter, preferably greater than about 1.0 cm in diameter, is a positive response, indicative of tuberculosis infection.

For use in a skin test, the polypeptides of the present invention are preferably formulated, as pharmaceutical compositions containing a polypeptide and a physiologically acceptable carrier, as described above. Such compositions typically contain one or more of the above polypeptides in an amount ranging from about 1 µg to about 100 µg, preferably from about 10 µg to about 50 µg in a volume of 0.1 mL. Preferably, the carrier employed in such pharmaceutical compositions is a saline solution with appropriate preservatives, such as phenol and/or Tween 8™.

In a preferred embodiment, a polypeptide employed in a skin test is of sufficient size such that it remains at the site of injection for the duration of the reaction period. In general, a polypeptide that is at least 9 amino acids in length is sufficient. The polypeptide is also preferably broken down by macrophages or dendritic cells within hours of injection to allow presentation to T-cells. Such polypeptides may contain repeats of one or more of the above sequences or other immunogenic or nonimmunogenic sequences.

In another aspect, methods are provided for detecting mycobacterial infection in a biological sample, using one or more of the above polypeptides, either alone or in combination. In embodiments in which multiple polypeptides are employed, polypeptides other than those specifically described herein, such as the 38 kD antigen described above, may be included. As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient or a blood supply. The polypeptide(s) are used in an assay, as described below, to determine the presence or absence of antibodies to the polypeptide(s) in the sample, relative to a predetermined cut-off value. The presence of such antibodies indicates the presence of mycobacterial infection.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with a Mycobacterium. After determining which samples test positive (as described below) with each polypeptide, combinations of two or more polypeptides may be formulated that are capable of detecting infection in most, or all, of the samples tested. For example, approximately 25–30% of sera from tuberculosis-infected individuals are negative for antibodies to any single protein, such as the 38 kD antigen mentioned above. Complementary polypeptides may, therefore, be used in combination with the 38 kD antigen to improve sensitivity of a diagnostic test.

A variety of assay formats employing one or more polypeptides to detect antibodies in a sample are well known in the art. See, e.g., Harlow and Lane, *Antibodies: A Laboratory Manual*, Cold Spring Harbor Laboratory, 1988. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labelled with a reporter group (e.g., in a semi-competitive assay). Alternatively, a competitive assay may be utilized, in which an antibody that binds to the polypeptide is labelled with a reporter group and allowed to bind to the immobilized antigen after incubation of the antigen with the sample. The extent to which components of the sample inhibit the binding of the labelled antibody to the polypeptide is indicative of the reactivity of the sample with the immobilized polypeptide.

The solid support may be any solid material to which the antigen may be attached. Suitable materials are well known in the art. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques well known in the art. In the context of the present invention, the term "bound" refers to both noncovalent association, such as adsorption, and covalent attachment, which may be a direct linkage between the antigen and functional groups on the support or a linkage by way of a cross-linking agent. Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 $\mu$g, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12-A13).

In certain embodiments, the assay is an enzyme-linked immunosorbent assay (ELISA). This assay may be performed by first contacting a polypeptide antigen that has been immobilized on a solid support, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin or Tween20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time, or incubation time, is that period of time that is sufficient to detect the presence of antibody within a *M. tuberculosis*-infected sample. Preferably, the contact time is sufficient to achieve a level of binding that is at least 95% of that achieved at equilibrium between bound and unbound antibody. The time necessary to achieve equilibrium may be readily determined by assaying the level of binding that occurs over a period of time. At room temperature, an incubation time of about 30 minutes is generally sufficient.

Unbound sample may be removed by washing the solid support with an appropriate buffer, such as PBS containing 0.1% Tween20™. Detection reagent may then be added to the solid support. An appropriate detection reagent is any compound that binds to the immobilized antibody-polypeptide complex and that can be detected by any of a variety of means known in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known in the art. Common binding agents may also be purchased conjugated to a variety of reporter groups from many commercial sources (e.g., Zymed Laboratories, San Francisco, Calif., and Pierce, Rockford, Ill.).

The detection reagent is incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dycs, luminescent groups and fluorescent groups. Biotin may be detected using avidin, coupled to a different reporter group (commonly a radioactive or fluorescent group or an enzyme). Enzyme reporter groups may be detected by the addition of substrate (generally for a specific period of time), followed by spectroscopic or other analysis of the reaction products.

To determine the presence or absence of anti-mycobacterial antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, pp. 106–107. In general, signals higher than the predetermined cut-off value are considered to be positive for mycobacterial infection.

The assay may also be performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane.

The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-mycobacterial antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 μg, and more preferably from about 50 ng to about 500 ng. Such tests can typically be performed with a very small amount (e.g., one drop) of patient serum or blood.

Numerous other assay protocols exist that are suitable for use with the polypeptides of the present invention. The above descriptions are intended to be exemplary only.

The present invention also provides antibodies to the inventive polypeptides. Antibodies may be prepared by any of a variety of techniques known to those of ordinary skill in the art. See, e.g, Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells may then be immortalized by fusion with a myeloma cell fusion partner, preferably one that is syngeneic with the immunized animal, using one of a variety of techniques well known in the art.

Monoclonal antibodies may be isolated from the supernatants of the resulting hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood.

Antibodies may be used in diagnostic tests to detect the presence of mycobacterial antigens using assays similar to those detailed above and other techniques well known to those of skill in the art, thereby providing a method for detecting mycobacterial infection, such as *M. tuberculosis* infection, in a patient.

Diagnostic reagents of the present invention may also comprise DNA sequences encoding one or more of the above polypeptides, or one or more portions thereof. For example, primers comprising at least 10 contiguous oligonucleotides of the subject DNA sequences may be used in polymerase chain reaction (PCR) based tests. Similarly, probes comprising at least 18 contiguous oligonucleotides of the subject DNA sequences may be used for hybridizing to specific sequences. Techniques for both PCR based tests and hybridization tests are well known in the art. Primers or probes may thus be used to detect *M. tuberculosis* and other mycobacterial infections in biological samples, preferably sputum, blood, serum, saliva, cerebrospinal fluid or urine. DNA probes or primers comprising oligonucleotide sequences described above may be used alone, in combination with each other, or with previously identified sequences, such as the 38 kD antigen discussed above.

As discussed above, effective vaccines contain at least two different components. The first is a polypeptide comprising an antigen, which is processed by macrophages and other antigen-presenting cells and displayed for $CD4^+$ T cells or for $CD8^+$ T cells. This antigen forms the "specific" target of an immune response. The second component of a vaccine is a non-specific immune response amplifier, such as an adjuvant or a liposome, into which the antigen is incorporated. An adjuvant amplifies immune responses to a structurally unrelated compound or polypeptide. Several adjuvants are prepared from microbes such as *Bordetella pertussis*, *M. tuberculosis* and *M. bovis* BCG. Adjuvants may also contain components designed to protect polypeptide antigens from degradation, such as aluminum hydroxide or mineral oil.

While the antigenic component of a vaccine contains polypeptides that direct the immune attack against a specific pathogen, such as *M. tuberculosis*, the adjuvant is often capable of broad use in many different vaccine formulations. Certain pathogens, such as *M. tuberculosis*, as well as certain cancers, are effectively contained by an immune attack directed by T cells, $CD4^+$ T cells or $CD8^+$ T cells, known as cell-mediated immunity. Other pathogens, such as poliovirus, also require antibodies produced by B cells for containment. These different classes of immune attack (T cell or B cell) are controlled by different subpopulations of $CD4^+$ T cells, commonly referred to as Th1 and Th2 cells. A desirable property of an adjuvant is the ability to selectively amplify the function of either Th1 or Th2 populations of $CD4^+$ T cells.

As shown below in Example 6, *M. vaccae* and a modified (delipidated) form of autoclaved *M. vaccae* have been found to have adjuvant properties. Furthermore, it has been found that *M. vaccae* produces compounds which amplify the immune response to *M. vaccae* antigens, as well as to antigens from other sources. The present invention thus provides methods for enhancing immune responses to an antigen comprising administering killed *M. vaccae* cells, *M. vaccae* culture filtrate or delipidated *M. vaccae* cells. As detailed below, further studies have demonstrated that this non-specific immune amplifying effect is due, at least in part, to an *M. vaccae* polypeptide having homology to eat shock protein 65 (GroEL), previously identified in *M. tuberculosis*.

The following examples are offered by way of illustration and not by way of imitation.

EXAMPLE 1

Effect of Immunization of Mice with *M. vaccae* on Tuberculosis

This example illustrates the effect of immunization with *M. vaccae* or *M. vaccae* culture filtrate in mice prior to challenge with live *M. tuberculosis*.

*M. vaccae* (ATCC Number 15483) was cultured in sterile Medium 90 (yeast extract, 2.5 g/l; tryptone, 5 g/l; glucose, 1 g/l) at 37° C. The cells were harvested by centrifugation, and transferred into sterile Middlebrook 7H9 medium (Difco Laboratories, Detroit, Mich., USA) with glucose at 37° C. for one day. The medium was then centrifuged to pellet the bacteria, and the culture filtrate removed. The bacterial pellet was resuspended in phosphate buffered saline at a concentration of 10 mg/ml, equivalent to $10^{10}$ *M. vaccae* organisms per ml. The cell suspension was then autoclaved for 15 min at 120° C. The culture filtrate was passaged through a 0.45 μM filter into sterile bottles.

As shown in FIG. 1A, when mice were immunized with 1 mg, 100 μg or 10 μg of *M. vaccae* and infected three weeks later with $5\times10^5$ colony forming units (CFU) of live *M. tuberculosis* H37Rv, significant protection from infection was seen. In this example, spleen, liver and lung tissue was harvested from mice three weeks after infection, and live bacilli determined (expressed as CFU). The reduction in bacilli numbers, when compared to tissue from non-immunized control mice, exceeded 2 logs in liver and lung tissue, and 1 log in spleen tissue. Immunization of mice with heat-killed *M. tuberculosis* H37Rv had no significant protective effects on mice subsequently infected with live *M. tuberculosis* H37Rv.

Figure 1B:
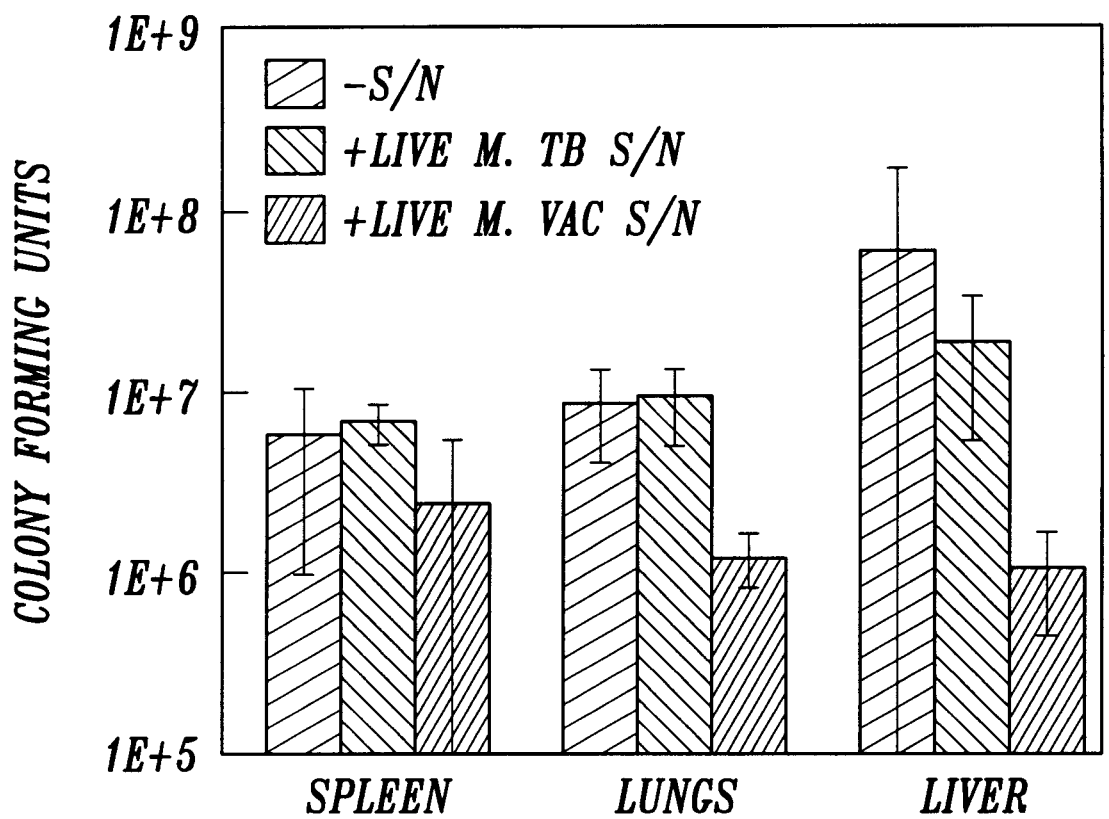

FIG. 1B shows that when mice were immunized with 100 μg of *M. vaccae* culture filtrate, and infected three weeks later with $5\times10^5$ CFU of *M. tuberculosis* H37Rv, significant protection was also seen. When spleen, liver and lung tissue was harvested from mice three weeks after infection, and live bacilli numbers (CFU) determined, a 1–2 log reduction in numbers, as compared to non-immunized control mice, was observed.

EXAMPLE 2

Purification and Characterization of Polypeptides From *M. vaccae* Culture Filtrate This example illustrates the preparation of *M. vaccae* soluble proteins from culture filtrate. Unless otherwise noted, all percentages in the following example are weight per volume.

*M. vaccae* (ATCC Number 15483) was cultured in sterile Medium 90 at 37° C. The cells were harvested by centrifugation, and transferred into sterile Middlebrook 7H9 medium with glucose at 37° C. for one day. The medium was then centrifuged (leaving the bulk of the cells) and filtered through a 0.45μ filter into sterile bottles.

The culture filtrate was concentrated by lyophilization, and redissolved in MilliQ water. A small amount of insoluble material was removed by filtration through a 0.45μ membrane. The culture filtrate was desalted by membrane filtration in a 400 ml Amicon stirred cell which contained a 3,000 kilodalton molecular weight cut-off (MWCO) membrane. The pressure was maintained at 50 psi using nitrogen gas. The culture filtrate was repeatedly concentrated by membrane filtration and diluted with water until the conductivity of the sample was less than 1.0 mS. This procedure reduced the 20 l volume to approximately 50 ml. Protein concentrations were determined by the Bradford protein assay (Bio-Rad, Hercules, Calif., USA).

The desalted culture filtrate was fractionated by ion exchange chromatography on a column of Q-Sepharose (Pharmacia Biotech, Uppsala, Sweden) (16×100 mm) equilibrated with 10 mM Tris HCl buffer pH 8.0. Polypeptides were eluted with a linear gradient of NaCl from 0 to 1.0 M in the above buffer system. The column eluent was monitored at a wavelength of 280 nm.

The pool of polypeptides eluting from the ion exchange column was concentrated in a 400 ml Amicon stirred cell which contained a 3,000 MWCO membrane. The pressure was maintained at 50 psi using nitrogen gas. The polypeptides were repeatedly concentrated by membrane filtration and diluted with 1% glycine until the conductivity of the sample was less than 0.1 mS.

The purified polypeptides were then fractionated by preparative isoelectric focusing in a Rotofor device (Bio-Rad, Hercules, Calif., USA). The pH gradient was established with a mixture of Ampholytes (Pharmacia Biotech) comprising 1.6% pH 3.5–5.0 Ampholytes and 0.4% pH 5.0–7.0 Ampholytes. Acetic acid (0.5 M) was used as the anolyte, and 0.5 M ethanolamine as the catholyte. Isoelectric focusing was carried out at 12W constant power for 6 hours, following the manufacturer's instructions. Twenty fractions were obtained.

Fractions from isoelectric focusing were combined, and the polypeptides were purified on a Vydac C4 column (Separations Group, Hesperia, Calif., USA) 300 Angstrom pore size, 5 micron particle size (10×250 mm). The polypeptides were eluted from the column with a linear gradient of acetonitrile (0–80% v/v) in 0.05% (v/v) trifluoroacetic acid (TFA). The flow-rate was 2.0 ml/min and the HPLC eluent was monitored at 220 nm. Fractions containing polypeptides were collected to maximize the purity of the individual samples.

Relatively abundant polypeptide fractions were rechromatographed on a Vydac C4 column (Separations Group) 300 Angstrom pore size, 5 micron particle size (4.6×250 mm). The polypeptides were eluted from the column with a linear gradient from 20–60% (v/v) of acetonitrile in 0.05% (v/v) TFA at a flow-rate of 1.0 ml/min. The column eluent was monitored at 220 nm. Fractions containing the eluted polypeptides were collected to maximise the purity of the individual samples. Approximately 20 polypeptide samples were obtained and they were analysed for purity on a polyacrylamide gel according to the procedure of Laemmli (Laemmli, U. K., *Nature* 277:680–685, 1970).

The polypeptide fractions which were shown to contain significant contamination were further purified using a Mono Q column (Pharmacia Biotech) 10 micron particle size (5×50 mm) or a Vydac Diphenyl column (Separations Group) 300 Angstrom pore size, 5 micron particle size (4.6×250 mm). From a Mono Q column, polypeptides were eluted with a linear gradient from 0–0.5 M NaCl in 10 mM Tris HCl pH 8.0. From a Vydac Diphenyl column, polypeptides were eluted with a linear gradient of acetonitrile (20–60% v/v) in 0. 1% TFA. The flow-rate was 1.0 ml/min and the column eluent was monitored at 220 nm for both columns. The polypeptide peak fractions were collected and analysed for purity on a 15% polyacrylamide gel as described above.

For sequencing, the polypeptides were individually dried onto Biobrene™ (Perkin Elmer/Applied BioSystems Division, Foster City, Calif.)-treated glass fiber filters. The filters with polypeptide were loaded onto a Perkin Elmer/Applied BioSystems Procise 492 protein sequencer and the polypeptides were sequenced from the amino terminal end using traditional Edman chemistry. The amino acid sequence was determined for each polypeptide by comparing the retention time of the PTH amino acid derivative to the appropriate PTH derivative standards.

Internal sequences were also determined on some antigens by digesting the antigen with the endoprotease Lys-C, or by chemically cleaving the antigen with cyanogen bromide. Peptides resulting from either of these procedures were separated by reversed-phase HPLC on a Vydac C8 column using a mobile phase of 0.05% (v/v) trifluoroacetic acid with a gradient of acetonitrile containing 0.05% (v/v) TFA (1%/min). The eluent was monitored at 214 nm. Major internal peptides were identified by their UV absorbance, and their N-terminal sequences were determined as described above.

Using the procedures described above, six soluble M. vaccae antigens, designated GVc-1, GVc-2, GVc-7, GVc-13, GVc-20 and GVc-22, were isolated. Determined Nterminal and internal sequences for GVc-1 are shown in SEQ ID NOS: , 2 and 3, respectively; the N-terminal sequence for GVc-2 is shown in SEQ ID NO: 4; internal sequences for GVc-7 are shown in SEQ ID NOS: 5–8; internal sequences for GVc-13 are shown in SEQ ID NOS: 9–11; internal sequence for GVc-20 is shown in SEQ ID NO: 12; and N-terminal and internal sequences for GVc-22 are shown in SEQ ID NO:56–59, respectively. Each of the internal peptide sequences provided herein begins with an amino acid residue which is assumed to exist in this position in the polypeptide, based on the known cleavage specificity of cyanogen bromide (Met) or Lys-C (Lys).

Three additional polypeptides, designated GVc-16, GVc-18 and GVc-21, were isolated employing a preparative sodium dodecyl sulfate-polyacrylamide gel electrophoresis (SDS-PAGE) purification step in addition to the preparative isoelectric focusing procedure described above. Specifically, fractions comprising mixtures of polypeptides from the preparative isoelectric focusing purification step previously described, were purified by preparative SDS-PAGE on a 15% polyacrylamide gel. The samples were dissolved in reducing sample buffer and applied to the gel. The separated proteins were transferred to a polyvinylidene difluoride (PVDF) membrane by electroblotting in 10 mM 3-(cyclohexylamino)-1-propanesulfonic acid (CAPS) buffer pH 11 containing 10% (v/v) methanol. The transferred protein bands were identified by staining the PVDF membrane with Coomassie blue. Regions of the PVDF membrane containing the most abundant polypeptide species were cut out and directly introduced into the sample cartridge of the Perkin Elmer/Applied BioSystems Procise 492 protein sequencer. Protein sequences were determined as described above. The N-terminal sequences for GVc-16, GVc-18 and GVc-21 are provided in SEQ ID NOS: 13, 14 and 15, respectively.

Additional antigens, designated GVc-12, GVc-14, GVc-15, GVc-17 and GVc-19, were isolated employing a preparative SDS-PAGE purification step in addition to the chromatographic procedures described above. Specifically, fractions comprising a mixture of antigens from the Vydac C4 HPLC purification step previously described were fractionated by preparative SDS-PAGE on a polyacrylamide gel. The samples were dissolved in non-reducing sample buffer and applied to the gel. The separated proteins were transferred to a PVDF membrane by electroblotting in 10 mM CAPS buffer, pH 11 containing 10% (v/v) methanol. The transferred protein bands were identified by staining the PVDF membrane with Coomassie blue. Regions of the PVDF membrane containing the most abundant polypeptide species were cut out and directly introduced into the sample cartridge of the Perkin Elmer/Applied BioSystems Procise 492 protein sequencer. Protein sequences were determined as described above. The determined N-terminal sequences for GVc-12, GVc-14, GVc-15, GVc-17 and GVc-19 are provided in SEQ ID NOS: 16–20, respectively.

All of the above amino acid sequences were compared to known amino acid sequences in the SwissProt data base (version R32) using the GeneAssist system. No significant homologies to the amino acid sequences GVc-2 to GVc-22 were obtained. The amino acid sequence for GVc-1 was found to bear some similarity to sequences previously identified from M. bovis and M. tuberculosis. In particular, GVc-1 was found to have some homology with M. tuberculosis MPT83, a cell surface protein, as well as MPT70. These proteins form part of a protein family (Harboe et al., Scand. J. Immunol. 42:46–51, 1995).

Amplifications primers AD86 and AD 112 (SEQ ID NO: 60 and 61, respectively) were designed from the amino acid sequence of GVc-1 (SEQ ID NO: 1) and the M. tuberculosis MPT70 gene sequence. Using these primers, a 310 bp fragment was amplified from M. vaccae genomic DNA and cloned into EcoRV-digested vector pBluescript (Stratagene) containing added dTTP residues. The sequence of the cloned insert is provided in SEQ ID NO: 62.

The purified polypeptides were screened for the ability to induce T-cell proliferation and IFN-γ in peripheral blood cells from immune human donors. These donors were known to be PPD (purified protein derivative from M. tuberculosis) skin test positive and their T cells were shown to proliferate in response to PPD. Donor PBMCs and crude soluble proteins from M. vaccae culture filtrate were cultured in medium comprising RPMI 1640 supplemented with 10% (v/v) autologous serum, penicillin (60 µg/ml), streptomycin (100 µg/ml), and glutamine (2 mM).

After 3 days, 50 µl of medium was removed from each well for the determination of IFN-γ levels, as described below. The plates were cultured for a further 4 days and then pulsed with 1 µCi/well of tritiated thymidine for a further 18 hours, harvested and tritium uptake determined using a scintillation counter. Fractions that stimulated proliferation in both replicates two-fold greater than the proliferation observed in cells cultured in medium alone were considered positive.

IFN-γ was measured using an enzyme-linked immunosorbent assay (ELISA). ELISA plates were coated with a mouse monoclonal antibody directed to human IFN-γ (Endogen, Wobural, Mass.) 1 µg/ml phosphate-buffered saline (PBS) for 4 hours at 4° C. Wells were blocked with PBS containing 0.2% Tween 20 for 1 hour at room temperature. The plates were then washed four times in PBS/0.2% Tween 20, and samples diluted 1:2 in culture medium in the ELISA plates were incubated overnight at room temperature. The plates were again washed, and a biotinylated polyclonal rabbit anti-human IFN-γ serum (Endogen), diluted to 1 µg/ml in PBS, was added to each well. The plates were then incubated for 1 hour at room temperature, washed, and horseradish peroxidasecoupled avidin A (Vector Laboratories, Burlingame, Calif.) was added at a 1:4,000 dilution in PBS. After a further 1 hour incubation at room temperature, the plates were washed and orthophenylenediamine (OPD) substrate added. The reaction was stopped after 10 min with 10% (v/v) HCl. The optical density (OD) was determined at 490 nm. Fractions that resulted in both replicates giving an OD two-fold greater than the mean OD from cells cultured in medium alone were considered positive.

Examples of polypeptides containing sequences that stimulate peripheral blood mononuclear cells (PBMC) T cells to proliferate and produce IFN-γ are shown in Table 1, wherein (−) indicates a lack of activity, (+/−) indicates polypeptides having a result less than twice higher than background activity of control media, (+) indicates polypeptides having activity two to four times above background, and (++) indicates polypeptides having activity greater than four times above background.

TABLE 1

| Antigen | Proliferation | IFN-g |
|---------|---------------|-------|
| GVc-1   | ++            | +/−   |
| GVc-2   | +             | ++    |
| GVc-7   | +/−           | −     |
| GVc-13  | +             | ++    |
| GVc-14  | ++            | +     |
| GVc-15  | +             | +     |
| GVc-20  | +             | +     |

EXAMPLE 3

Purification and Characterisation of Polypeptides From *M. vaccae* Culture Filtrate Be 2-Dimensional Polyacrylamide Gel Electrophoresis

*M. vaccae* soluble proteins were isolated from culture filtrate using 2-dimensional polyacrylamide gel electrophoresis as described below. Unless otherwise noted, all percentages in the following example are weight per volume.

*M. vaccae* (ATCC Number 15483) was cultured in sterile Medium 90 at 37° C. *M. tuberculosis* strain H37Rv (ATCC number 27294) was cultured in sterile Middlebrook 7H9 medium with Tween 80 and oleic acid/albumin/dextrose/catalase additive (Difco Laboratories, Detroit, Mich.). The cells were harvested by centrifugation, and transferred into sterile Middlebrook 7H9 medium with glucose at 37° C. for one day. The medium was then centrifuged (leaving the bulk of the cells) and filtered through a $0.45\mu$ filter into sterile bottles. The culture filtrate was concentrated by lyophilisation, and redissolved in MilliQ water. A small amount of insoluble material was removed by filtration through a $0.45\mu$ membrane filter.

The culture filtrate was desalted by membrane filtration in a 400 ml Amicon stirred cell which contained a 3,000 MWCO membrane. The pressure was maintained at 60 psi using nitrogen gas. The culture filtrate was repeatedly concentrated by membrane filtration and diluted with water until the conductivity of the sample was less than 1.0 mS. This procedure reduced the 20 L volume to approximately 50 mL. Protein concentrations were determined by the Bradford protein assay (Bio-Rad, Hercules, Calif., USA).

The desalted culture filtrate was fractionated by ion exchange chromatography on a column of Q-Sepharose (Pharmacia Biotech) (16×100 mm) equilibrated with 10 mM TrisHCL buffer pH 8.0. Polypeptides were eluted with a linear gradient of NaCl from 0 to 1.0 M in the above buffer system. The column eluent was monitored at a wavelength of 280 nm.

Figure 2A:
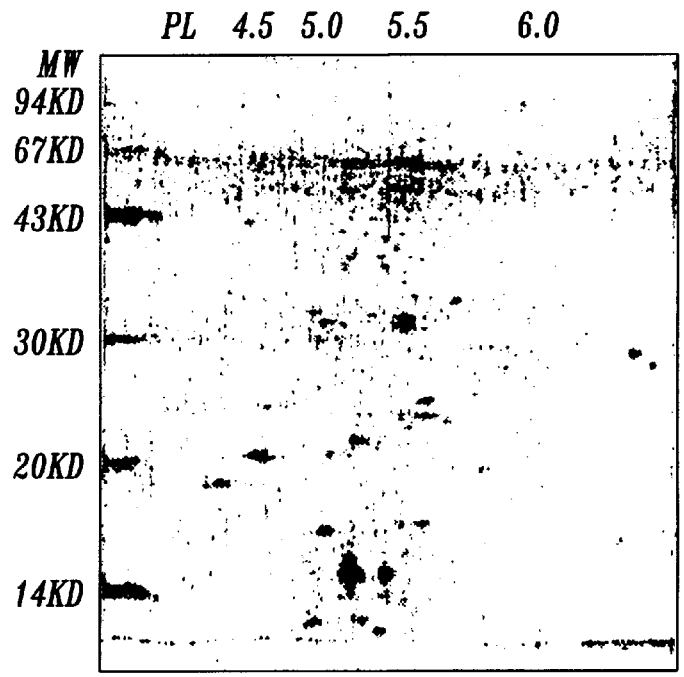
FIGS. 2A and B show components of M. vaccae and M. tuberculosis culture filtrates, respectively, as analysed by 2-dimensional polyacrylamide gel electrophoresis.
Figure 2B:
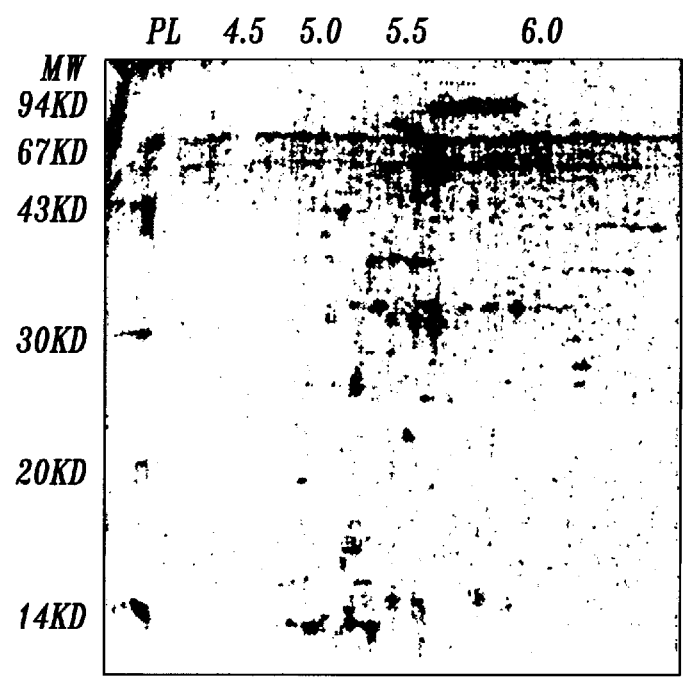

The pool of polypeptides eluting from the ion exchange column were fractionated by preparative 2D gel electrophoresis. Samples containing 200–500 ug of polypeptide were made 8M in urea and applied to polyacrylamide isoelectric focusing rod gels (diameter 2 mm, length 150 mm, pH 5–7). After the isoelectric focusing step, the first dimension gels were equilibrated with reducing buffer and applied to second dimension gels (16% polyacrylamide). FIGS. 2A and 2B are the 2-D gel patterns observed with *M. vaccae* culture filtrate and *M. tuberculosis* H37Rv culture filtrate, respectively. Polypeptides from the second dimension separation were transferred to PVDF membranes by electroblotting in 10 mM CAPS buffer pH 11 containing 10% (v/v) methanol. The PVDF membranes were stained for protein with Coomassie blue. Regions of PVDF containing polypeptides of interest were cut out and directly introduced into the sample cartridge of the Perkin Elmer/Applied BioSystems Procise 492 protein sequencer. The polypeptides were sequenced from the amino terminal end using traditional Edman chemistry. The amino acid sequence was determined for each polypeptide by comparing the retention time of the PTH amino acid derivative to the appropriate PTH derivative standards. Using these procedures, eleven polypeptides, designated GVs-1, GVs-3, GVs-4, GVs-5, GVs-6, GVs-8, GVs-9, GVs-10, GVs-11, GV34 and GV-35 were isolated. The determined N-terminal sequences for these polypeptides are shown in SEQ ID NOS: 21–29, 63 and 64, respectively. In further studies, using the purification procedure described above, more protein was purified to extend the amino acid sequence previously obtained for GVs-9. The extended amino acid sequence for GVs-9 is provided in SEQ ID NO:65.

All of these amino acid sequences were compared to known amino acid sequences in the SwissProt data base (version R32) using the GeneAssist system. No significant homologies were obtained, with the exceptions of GVs-3, GVs-4, GVs-5 and GVs-9. GVs-9 was found to bear some homology to two previously identified *M. tuberculosis* proteins, namely *M. tuberculosis* cutinase precursor and an *M. tuberculosis* hypothetical 22.6 kD protein. GVs-3, GVs-4 and GVs-5 were found to bear some similarity to the antigen 85A and 85B proteins from *M. leprae* (SEQ ID NOS: 30 and 31, respectively), *M. tuberculosis* (SEQ ID NOS: 32 and 33, respectively) and *M. bovis* (SEQ ID NOS: 34 and 35, respectively), and the antigen 85C proteins from *M. leprae* (SEQ ID NO: 36) and *M. tuberculosis* (SEQ ID NO: 37). A comparison of the inventive antigen 85A protein from *M. vaccae* with those from *M. tuberculosis*, *M. bovis* and *M. leprae*, is presented in FIG. 3.

EXAMPLE 4

DNA Cloning Strategy for the *M. vaccae* Antigen 85 Series

Probes for antigens 85A, 85B, and 85C (SEQ ID NOS: 38 and 39) were prepared by the polymerase chain reaction (PCR) using degenerate oligonucleotides designed to regions of antigen 85 genomic sequence that are conserved between family members in a given mycobacterial species, and between mycobacterial species. These oligonucleotides were used under reduced stringency conditions to amplify target sequences from *M. vaccae* genomic DNA. An appropriately-sized 0.5 kb band was identified, purified, and cloned into T-tailed p Bluescript II SK (Stratagene, La Jolla, Calif.). Twenty-four individual colonies were screened at random for the presence of the antigen 85 PCR product, then sequenced using the Perkin Elmer/Applied Biosystems Model 377 automated sequencer and the M13-based primers, T3 and T7. Homology searches of the GenBank databases showed that twenty-three clones contained insert with significant homology to published antigen 85 genes from *M. tuberculosis* and *M. bovis*. Approximately half were most homologous to antigen 85C gene sequences, with the remainder being more similar to antigen 85B sequences. In addition, these two putative *M. vaccae* antigen 85 genomic sequences were 80% homologous to one another. Because of this high similarity, the antigen 85C PCR fragment was chosen to screen *M. vaccae* genomic libraries at low stringency for all three antigen 85 genes.

An M. vaccae genomic library was created in λ ZapExpress (Stratagene, La Jolla, Calif.) by cloning BamHI partially-digested M. vaccae genomic DNA into similarly-digested λ vector, with $3.4 \times 10^5$ independent plaque-forming units resulting. For screening purposes, twenty-seven thousand plaques from this non-amplified library were plated at low density onto eight 100 cm² plates. For each plate, duplicate plaque lifts were taken onto Hybond-N⁺ nylon membrane (Amersham International, United Kingdom), and hybridised under reducedstringency conditions (55° C.) to the radiolabelled antigen 85C PCR product. Autoradiography demonstrated that seventy-nine plaques consistently hybridised to the antigen 85C probe under these conditions. Thirteen positively-hybridising plaques were selected at random for further analysis and removed from the library plates, with each positive clone being used to generate secondary screening plates containing about two hundred plaques. Duplicate lifts of each plate were taken using Hybond-N⁺ nylon membrane, and hybridised under the conditions used in primary screening. Multiple positively-hybridising plaques were identified on each of the thirteen plates screened. Two well-isolated positive phage from each secondary plate were picked for further analysis. Using in vitro excision, twenty-six plaques were converted into phagemid, and restriction-mapped. It was possible to group clones into four classes on the basis of this mapping. Sequence data from the 5' and 3' ends of inserts from several representatives of each group was obtained using the Applied Biosystems Model 377 automated sequencer and the T 3 and T7 primers. Sequence homologies were determined using FASTA analysis of the GenBank databases with the GeneAssist software package. Two of these sets of clones were found to be homologous to M. bovis and M. tuberculosis antigen 85A genes each containing either the 5' or 3' ends of the M. vaccae gene (this gene was cleaved during library construction as it contains an internal BamHI site). The remaining clones were found to contain sequences homologous to antigens 85B and 85C from a number of mycobacterial species. To determine the remaining nucleotide sequence for each gene, appropriate subclones were constructed and sequenced. Overlapping sequences were aligned using the DNA Strider software. The determined DNA sequences for M. vaccae antigens 85A, 85B and 85C are shown in SEQ ID NOS: 40–42, respectively, with the predicted amino acid sequences being shown in SEQ ID NOS: 43–45, respectively.

The M. vaccae antigens GVc-3 and GVc-5 were expressed and purified as follows. Amplification primers were designed from the insert sequences of GVc-3 and GVc-5 (SEQ ID NO: 40 and 42, respectively) using sequence data downstream from the putative leader sequence and the 3' end of the clone. The sequences of the primers for GVc-3 are provided in SEQ ID NO: 66 and 67, and the sequences of the primers for GVc-5 are provided in SEQ ID NO: 68 and 69. A AhoI restriction site was added to the primers for GVc-3, and EcoRI and BamHI restriction sites were added to the primers for GVc-5 for cloning convenience. Following amplification from genomic M. vaccae DNA, fragments were cloned into the appropriate site of pProEX HT prokaryotic expression vector (Gibco BRL, Life Technologies, Gaithersburg, MD) and submitted for sequencing to confirm the correct reading frame and orientation. Expression and purification of the recombinant protein was performed according to the manufacturer's protocol.

Expression of a fragment of the M. vaccae antigen GVc-4 (antigen 85B homolog) was performed as follows. The primers AD58 and AD59, described above, were used to amplify a 485 bp fragment from M. vaccae genomic DNA. This fragment was gel-purified using standard techniques and cloned into EcoRV-digested pBluescript containing added dTTP residues. The base sequences of inserts from five clones were determined and found to be identical to each other. These inserts had highest homology to Ag85B from M. tuberculosis. The insert from one of the clones was subcloned into the EcoRI/XhoI sites of pProEX HT prokaryotic expression vector (Gibco BRL), expressed and purified according to the manufacturer's protocol. This clone was renamed GVc-4P because only a part of the gene was expressed. The amino acid and DNA sequences for the partial clone GVc-4P are provided in SEQ ID NO: 70 and 106, respectively.

The ability of purified recombinant GVc-3, GVc-4P and GVc-5 to stimulate proliferation of T cells and interferon-γ production in human PBL was assayed as described above in Example 2. The results of this assay are shown in Table 2, wherein (−) indicates a lack of activity, (+/−) indicates polypeptides having a result less than twice higher than background activity of control media, (+) indicates polypeptides having activity two to four times above background, (++) indicates polypeptides having activity greater than four times above background, and ND indicates not determined.

TABLE 2

| | Donor G97005 | | Donor G97006 | | Donor G97007 | | Donor G97008 | | Donor G97009 | | Donor G97010 | |
|---|---|---|---|---|---|---|---|---|---|---|---|---|
| | Prolif | IFN-g | Prolif | IFN-g | Prolif | IFN-g | Prolif | IFN-g | Prolif | IFN-g | Prolif | IFN-g |
| GVc-3 | ++ | + | ND | ND | ++ | ++ | ++ | ++ | ++ | +/− | + | ++ |
| GVc-4P | + | +/− | ND | ND | + | ++ | ++ | ++ | +/− | +/− | +/− | ++ |
| GVC-5 | ++ | ++ | ++ | ++ | ++ | ++ | + | ++ | ++ | + | + | ++ |

EXAMPLE 5

DNA Cloning Strategy for M. vaccae Antigens

An 84 bp probe for the M. vaccae antigen GVc-7 was amplified using degenerate oligonucleotides designed to the determined amino acid sequence of GVc-7 (SEQ ID NOS: 5–8). This probe was used to screen a M. vaccae genomic DNA library as described in Example 4. The determined nucleotide sequence for GVc-7 is shown in SEQ ID NO: 46 and predicted amino acid sequence in SEQ ID NO: 47. Comparison of these sequences with those in the databank revealed homology to a hypothetical 15.8 kDa membrane protein of M. tuberculosis.

The sequence of SEQ ID NO: 46 was used to design amplification primers (provided in SEQ ID NO: 71 and 72) for expression cloning of the GVc-7 gene using sequence data downstream from the putative leader sequence. A XhoI restriction site was added to the primers for cloning convenience. Following amplification from genomic *M. vaccae* DNA, fragments were cloned into the AhoI-site of pProEX HT prokaryotic expression vector (Gibco BRL) and submitted for sequencing to confirm the correct reading frame and orientation. Expression and purification of the fusion protein was performed according to the manufacturer's protocol.

The ability of purified recombinant GVc-7 to stimulate proliferation of T-cells and stimulation of interferon-γ production in human PBL was assayed as described previously in Example 2. The results are shown in Table 3, wherein (−) indicates a lack of activity, (+/−) indicates polypeptides having a result less than twice higher than background activity of control media, (+) indicates polypeptides having activity two to four times above background, and (++) indicates polypeptides having activity greater than four times above background.

TABLE 3

| Donor | Proliferation | Interferon-γ |
|---|---|---|
| G97005 | ++ | +/− |
| G97008 | ++ | + |
| G97009 | + | +/− |
| G97010 | +/− | ++ |

A redundant oligonucleotide probe was designed to the GVs-8 peptide sequence shown in SEQ ID NO: 6 and used to screen an *M. vaccae* genomic DNA library as described above. Positive plaques were isolated.

Four different genomic clones were identified, hereinafter referred to as GVs-8A, GVs-8B and GVs-8C and GVs-8D. The determined DNA sequences for the clones GVs-8A, GVs-8B, GVs-8C and GVs-8D are shown in SEQ ID NOS: 48–51, respectively, with the corresponding amino acid sequences being shown in SEQ ID NOS: 52–55, respectively. The clone GVs-8A contains regions showing some similarity to known prokaryotic valyl-tRNA synthetases; GVs-8B shows some similarity to *M. smegmatis* aspartate semialdehyde dehydrogenase; and GVs-8C shows some similarity to the *H. influenza* folylpolyglutamate synthase gene. GVs-8D contains an open reading frame which shows some similarity to sequences previously identified in *M. tuberculosis* and *M. leprae*, but whose function has not been identified.

In subsequent studies, the *M. vaccae* genomic DNA library constructed in the BamH1-site of lambda ZAP Express vector (Stratagene) was screened with a second redundant oligonucleotide (referred to as MPG15; SEQ ID NO:73) designed from the GVs-8 sequence provided in SlQ ID NO:6. Screening of the library was performed in the presence of tetramethylammonium chloride (TMAC), so that nucleotide base pairs would melt at a standard temperature independent of sequence (i.e. A–T pairs and G–C pairs melt at the same temperature). Hybridisation stringency therefore depended only on the length and degeneracy of the oligonucleotide used as probe (Wood et al. *Proc. Natl. Acad. Sci. USA*, 82:1585–1588,1985). Filters were prepared using standard methods of transfer and pre-hybridised overnight at a temperature ~15° C. below the appropriate TMAC wash temperature. Hybridisation was performed overnight in freshly prepared hybridisation solution containing 100 pmol probe.

Hybridisation Solution for Oligonucleotides Stock:

| 1 M Na Cl | 5 M |
|---|---|
| 0.1 M Tris pH 8 | 1 M |
| 5X Denhardt's 100X | |
| 0.05% NaPPi 5% | |
| 0.1% SDS 10% | |
| 0.1 mg/ml yeast tRNA | 10 mg/ml |
| 125 units/ml heparin | |

The filters were washed at a temperature calculated to allow approximately 4% mismatching in TMAC wash buffer. More specifically, the wash protocol included the following washing steps: 2×15 min in 6× SSC, 0.05% NaPPi at room temp; 1×15 min in TMAC wash (see below) at room temperature; 2×15 min in TMAC wash at the calculated stringent temperature; and 1×15 min in 6× SSC, 0.05% NaPPi at room temp.

TMAC wash buffer

3 M Tetramethylammonium chloride (TMAC)

50 mM Tris pH 8.0

0.2 mM EDTA

Positive plaques were picked and stored in 1 ml SM buffer with 20 μl chloroform. Screening was repeated until plaques were pure following the procedure described above.

The pBK-CMV phagemid containing the desired insert was excised from the lambda ZAP Express vector in the presence of ExAssist helper phage following the manufacturer's protocol. A phagemid containing an 8 kb insert (GVs-8D) was characterised by restriction mapping and sub-cloning. An open reading frame was identified at the 3' end of the insert and the antigen encoded by this open reading frame was named GV-33. Base sequence corresponding to GVs-8 was not found in the insert, and it was assumed that GV-33 was obtained as a non-specific product of the TMAC screening. By further sub-cloning and base sequencing, the 3' end of the gene was determined. The determined partial DNA sequence for GV-33 is provided in SEQ ID NO:74 with the corresponding predicted amino acid sequence being provided in SEQ ID NO:75. Sequence data from the 3' end of the clone showed homology to a previously identified 40.6 kDa outer membrane protein of *M. tuberculosis*.

The partial GV-33 gene was amplified from *M. vaccae* genomic DNA with primers based on the determined nucleotide sequence. This DNA fragment was cloned into EcoRv-digested pBluescript (Stratagene) with additional dTTP residues, and then transferred to pProEX HT expression vector (Gibco BRL) using EcoRI and HindIII-subcloning. Recombinant protein was purified following the manufacturer's protocol.

The ability of purified recombinant antigen to stimulate proliferation of T-cells and stimulation of interferon-γ production in human PBL was assayed as described previously in Example 2. The results are shown in Table 4, wherein (−) indicates a lack of activity, (+/−) indicates polypeptides having a result less than twice higher than background activity of control media, (+) indicates polypeptides having activity two to four times above background, and (++) indicates polypeptides having activity greater than four times above background.

TABLE 4

| Donor  | Proliferation | Interferon-γ |
|--------|---------------|--------------|
| G97005 | ++            | +            |
| G97006 | ++            | ++           |
| G97007 | −             | +/−          |
| G97008 | +/−           | −            |
| G97009 | +/−           | −            |
| G97010 | +/−           | ++           |

EXAMPLE 6

Detection of Nonspecific Immune Amplifier from Whole M. vaccae and the Culture Filtrate of M. vaccae This example illustrates the preparation of whole M. vaccae and M. vaccae culture filtrate and its non-specific immune amplifying or 'adjuvant' property.

M. vaccae bacteria was cultured, pelleted and autoclaved as described in Example 1. Culture filtrates of live M. vaccae refer to the supernatant from 24 hour cultures of M. vaccae in 7H9 medium with glucose. A delipidated form of M. vaccae was prepared by sonicating autoclaved M. vaccae for four bursts of 30 seconds on ice using the Virsonic sonicator (Virtis, Disa, USA). The material was then centrifuged (9000 rpm, 20 minutes, JA10 rotor, brake=5). The resulting pellet was suspended in 100 ml of chloroform/methanol (2:1), incubated at room temperature for 1 hour; recentrifuged, and the chloroform/methanol extraction repeated. The pellet was obtained by centrifugation, dried in vacuo, weighed and resuspended in PBS at 50 mg (dry weight) per ml as delipidated M. vaccae.

Glycolipids were removed from the delipidated M. vaccae preparation by refluxing in 50% v/v ethanol for 2 hours. The insoluble material was collected by centrifugation (10,000 rpm, JA20 rotor, 15 mins, brake=5). The extraction with 50% v/v ethanol under reflux was repeated twice more. The insoluble material was collected by centrifugation and washed in PBS. Proteins were extracted by resuspending the pellet in 2% SDS in PBS at 56° C. for 2 hours. The insoluble material was collected by centrifugation and the extraction with 2% SDS/PBS at 56° C. was repeated twice more. The pooled SDS extracts were cooled to 4° C., and precipitated SDS was removed by centrifugation (10,000 rpm, JA20 rotor, 15 mins, brake=5). Proteins were precipitated from the supernatant by adding an equal volume of acetone and incubating at −20° C. for 2 hours. The precipitated proteins were collected by centrifugation, washed in 50% v/v acetone, dried in vacuo, and redissolved in PBS.

M. vaccae culture supernatant (S/N), killed M. vaccae and delipidated M. vaccae were tested for adjuvant activity in the generation of cytotoxic T cell immune response to ovalbumin, a structurally unrelated protein, in the mouse. This anti-ovalbumin-specific cytotoxic response was detected as follows. C57BL/6 mice (2 per group) were immunized by the intraperitoneal injection of 100 μg of ovalbumin with the following test adjuvants: autoclaved M. vaccae; delipidated M. vaccae; delipidated M. vaccae with glycolipids also extracted and proteins extracted with SDS; the SDS protein extract treated with pronase (an enzyme which degrades protein); whole M. vaccae culture filtrate; and heat-killed M. tuberculosis or heat-killed M. bovis BCG, M. phlei or M. smegmatus or M. vaccae culture filtrate. After 10 days, spleen cells were stimulated in vitro for a further 6 days with E.G7 cells which are EL4 cells (a C57BL/6-derived T cell lymphoma) transfected with the ovalbumin gene and thus express ovalbumin. The spleen cells were then assayed for their ability to kill non-specifically EL4 target cells or to kill specifically the E.G7 ovalbumin expressing cells. Killing activity was detected by the release of $^{51}$ Chromium with which the EL4 and E.G7 cells have been labelled (100 μCi per 2×10$^6$), prior to the killing assay. Killing or cytolytic activity is expressed as % specific lysis using the formula:

$$\frac{\text{cpm in test cultures} - \text{cpm in control cultures}}{\text{total cpm} - \text{cpm in control cultures}} \times 100\%$$

It is generally known that ovalbumin-specific cytotoxic cells are generated only in mice immunized with ovalbumin with an adjuvant but not in mice immunized with ovalbumin alone.

The diagrams that make up FIG. 4 show the effect of various M. vaccae derived adjuvant preparations on the generation of cytotoxic T cells to ovalbumin in C57BL/6 mice. As shown in FIG. 4A, cytotoxic cells were generated in mice immunized with (i) 10 μg, (ii) 100 μg or (iii) 1 mg of autoclaved M. vaccae or (iv) 75 μg of M. vaccae culture filtrate. FIG. 4B shows that cytotoxic cells were generated in mice immunized with (i) 1 mg whole autoclaved M. vaccae or (ii) 1 mg delipidated M. vaccae. As shown in FIG. 4C(i), cytotoxic cells were generated in mice immunized with 1 mg whole autoclaved M. vaccae; FIG. 4C(ii) shows the active material in 100 μg delipidated M. vaccae which then had glycolipids removed and the proteins extracted with SDS. FIG. 4C(iii) shows that active material in the adjuvant preparation of FIG. 4C(ii) was destroyed by treatment with the proteolytic enzyme pronase. By way of comparison, 100 μg of the SDS-extracted proteins had significantly stronger immune-enhancing ability (FIG. 4C(ii)) than did 1 mg whole autoclaved M. vaccae (FIG. 4C(i)).

Figure 4A:
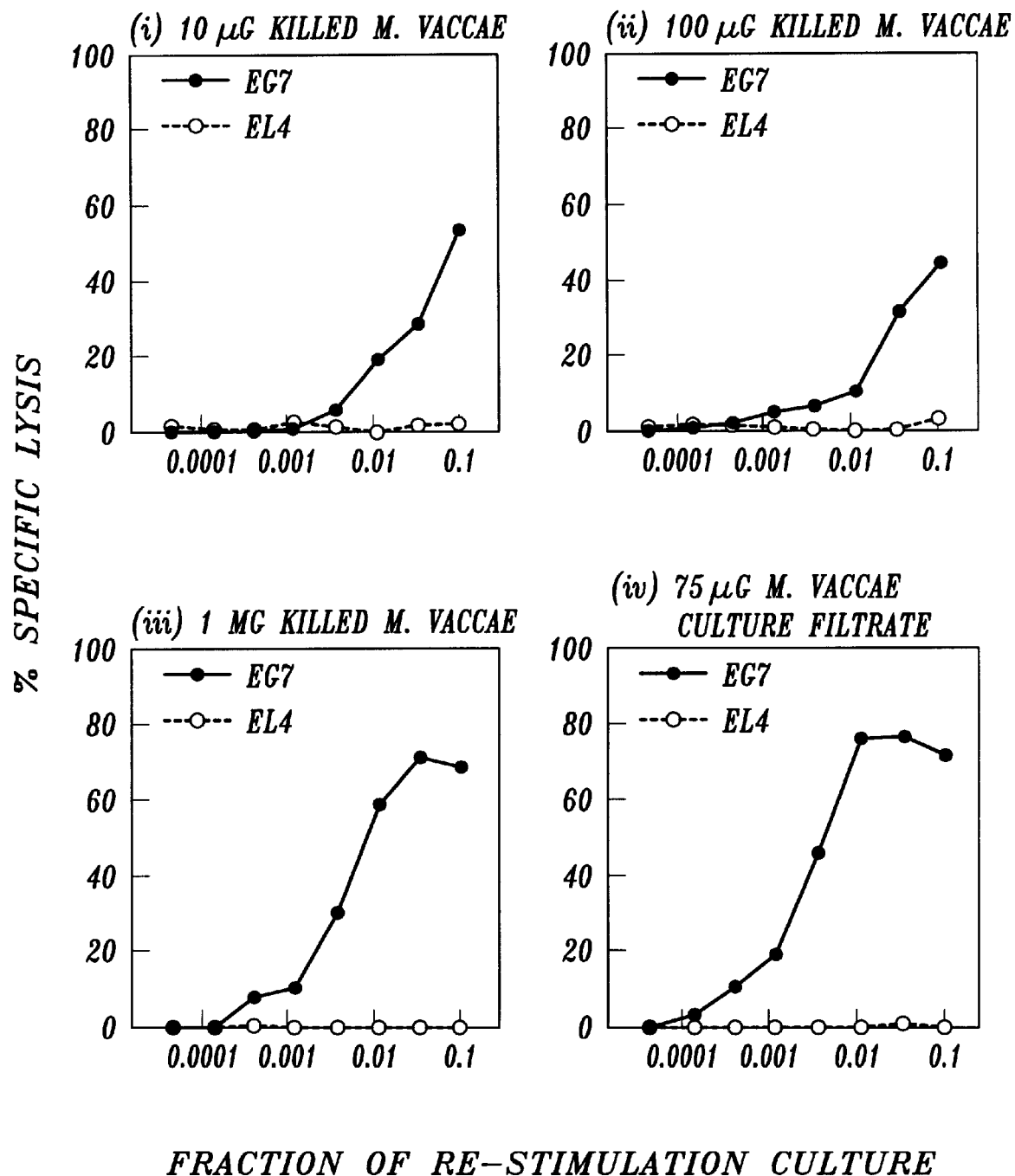
FIG. 4A(i)–(iv) illustrate the non-specific immune amplifying effects of 10 µg, 100 µg and 1 mg autoclaved M. vaccae and 75µg unfractionated culture filtrates of M. vaccae, respectively.
Figure 4B:
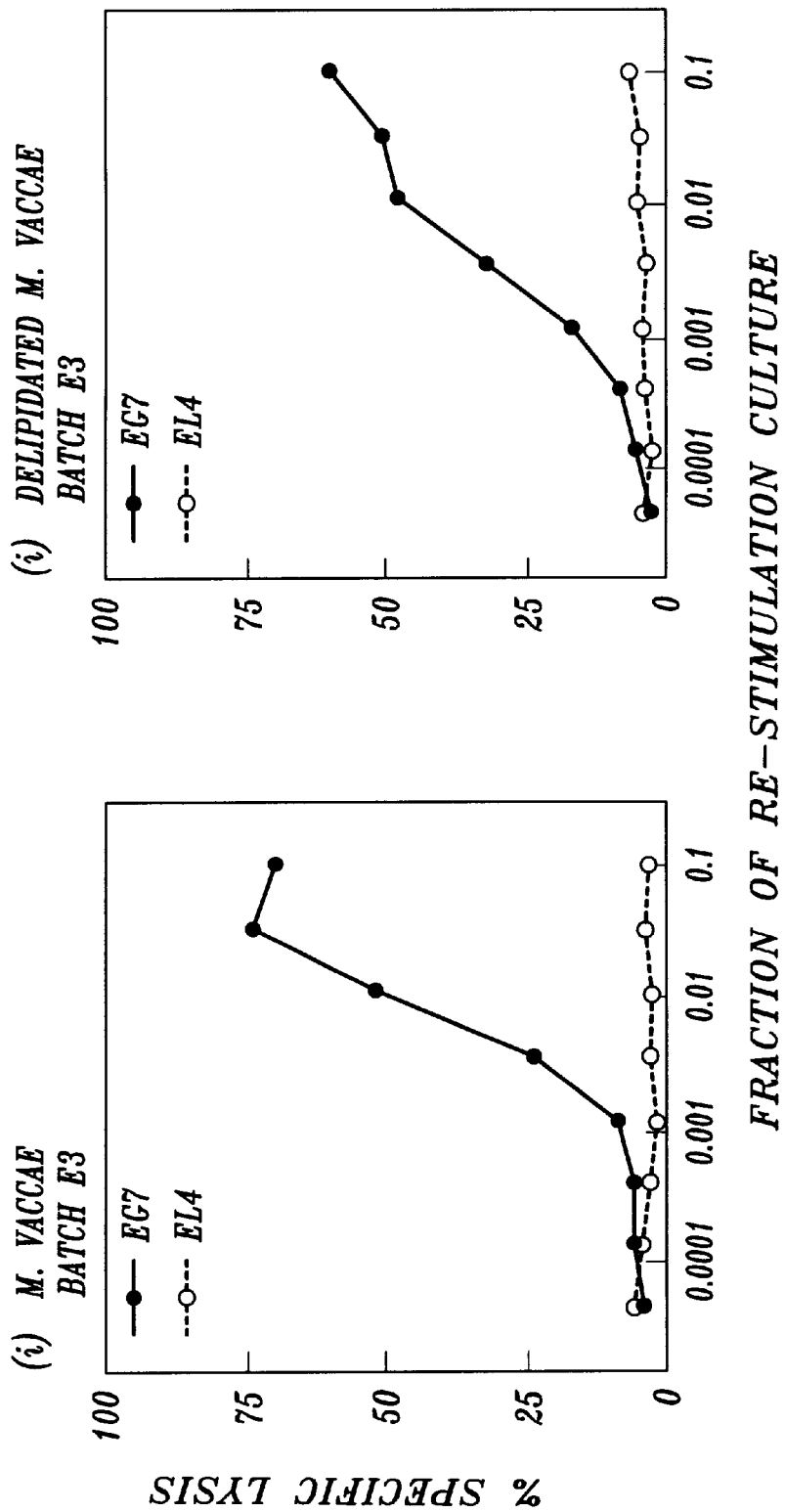
FIG. 4B illustrate the non-specific immune amplifying effects of autoclaved M. vaccae and delipidated M. vaccae, respectively.
Figure 4C:
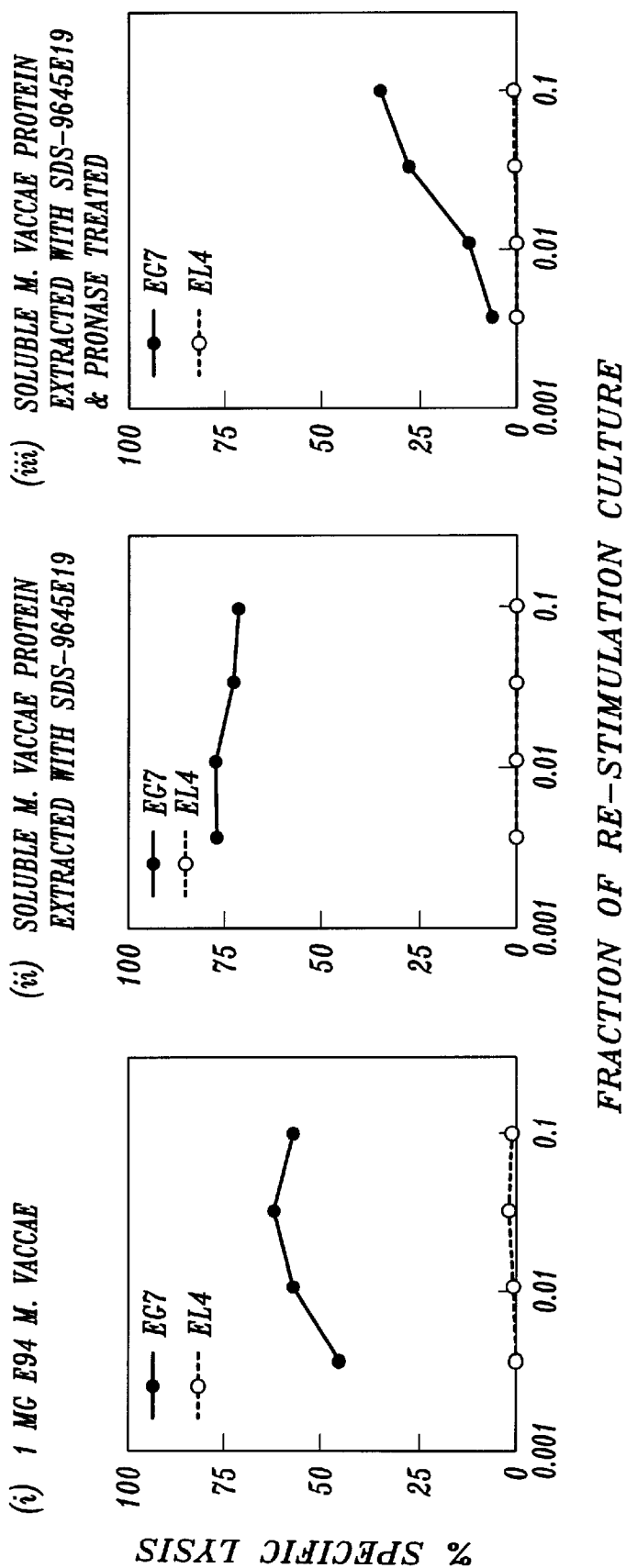
FIG. 4C(i) illustrates the non-specific immune amplifying effects of whole autoclaved M. vaccae.
Figure 4D:
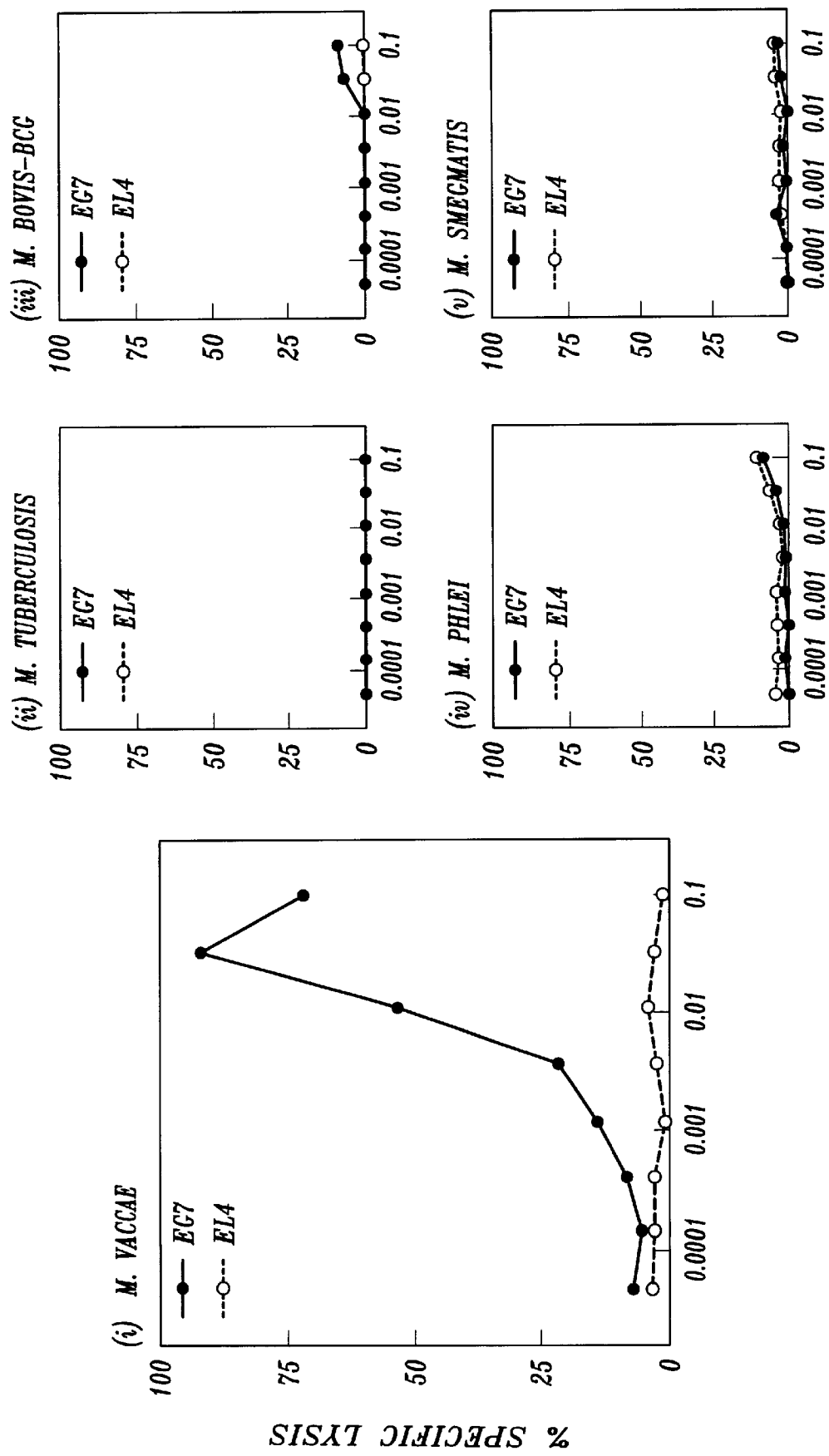
FIG. 4D illustrates the nonspecific immune amplifying effects of heat-killed M. vaccae (FIG. 4D(i)), M. tuberculosis (FIG. 4D(ii)), M. bovis BCG (FIG. 4D(iii)), M. phlei (FIG. 4D(iv)) and M. smegmatis (FIG. 4D(v)).

Mice immunized with 1 mg heat-killed M. vaccae (FIG. 4D(i)) generated cytotoxic cells to ovalbumin, but mice immunized separately with 1 mg heat-killed M. tuberculosis (FIG. 4D(ii)), 1 mg M. bovis BCG (FIG. 4D(iii)), 1 mg M. phlei (FIG. 4D(iv)), or 1 mg M. smegmatis (FIG. 4D(v)) failed to generate cytotoxic cells.

Figure 5:
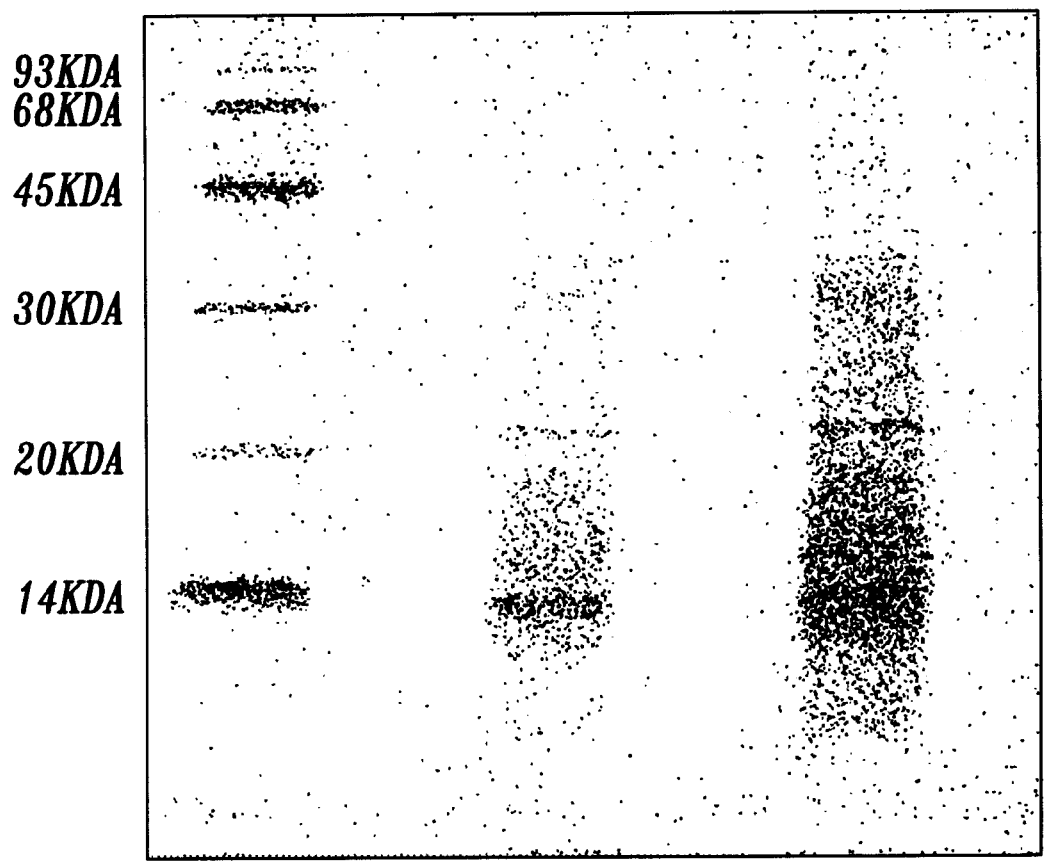
FIG. 5 shows the results of polyacrylamide gel electrophoresis analysis of SDS-extracted proteins derived from delipidated and deglycolipidated M. vaccae.

The SDS-extracted proteins derived from delipidated and deglycolipidated M. vaccae were analysed by polyacrylamide gel electrophoresis. As shown in FIG. 5, three major bands were observed after staining with silver.

Figure 6:
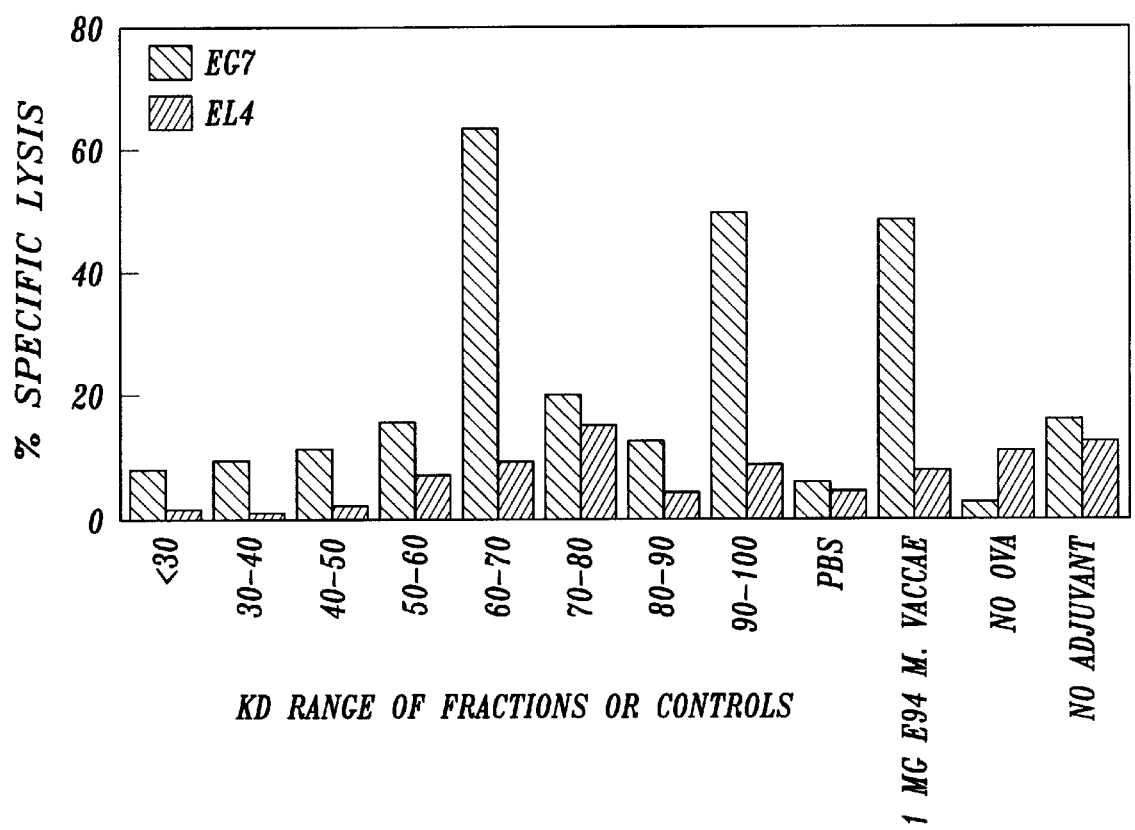
FIG. 6 illustrates the non-specific immune amplifying effects of different molecular weight fractions of SDS-extracted M. vaccae proteins.

In subsequent studies, more of the SDS-extracted proteins described above were prepared by preparative SDS-PAGE on a BioRad Prep Cell (Hercules, Calif.). Fractions corresponding to molecular weight ranges were precipitated by trichloroacetic acid to remove SDS before assaying for adjuvant activity in the anti-ovalbumin-specific cytotoxic response assay in C57BL/6 mice as described above. As seen in FIG. 6, the adjuvant activity was highest in the 60–70 kDa fraction. The most abundant protein in this size range was purified by SDS-PAGE blotted on to a polyvinylidene difluoride (PVDF) membrane and then sequenced. The sequence of the first ten amino acid residues is provided in SEQ ID NO:76. Comparison of this sequence with those in the gene bank as described above, revealed homology to the heat shock protein 65 (GroEL) gene from M. tuberculosis, indicating that this protein is an M. vaccae member of the GroEL family.

An expression library of M. vaccae genomic DNA in BamH 1-lambda ZAP Express (Stratagene) was screened using sera from cynomolgus monkeys immunised with *M. vaccae* secreted proteins prepared as described above. Positive plaques were identified using a colorimetric system. These plaques were re-screened until plaques were pure following standard procedures. pBK-CMV phagemid 2-1 containing an insert was excised from the lambda ZAP Express (Stratagene) vector in the presence of ExAssist helper phage following the manufacturer's protocol. The base sequence of the 5' end of the insert of this clone, hereinafter referred to as GV-27, was determined using Sanger sequencing with fluorescent primers on Perkin Elmer/Applied Biosystems Dvision automatic sequencer. The determined nucleotide sequence of the partial *M. vaccae* GroEL-homologue clone GV-27 is provided in SEQ ID NO:77 and the predicted amino acid sequence in SEQ ID NO:78. This clone was found to have homology to *M. tuberculosis* GroEL.

A partial sequence of the 65 kDa heat shock protein of *M. vaccae* has been published by Kapur et al. (*Arch. Pathol. Lab. Med.* 119:131–138, 1995). However, this sequence did not overlap with the GV-27 sequence provided herein. The nucleotide sequence of the Kapur et al. fragment is shown in SEQ ID NO:79 and the predicted amino acid sequence in SEQ ID NO:80.

The *M. vaccae* culture filtrate described above was also fractionated by isoelectric focusing and the fractions assayed for adjuvant activity in the anti-ovalbumin-specific cytotoxic response assay in C57BL/6 mice as described above. As shown in FIG. 7, peak adjuvant activities were demonstrated in fractions corresponding to pI of 4.2–4.32 (fraction nos. 7–9), 4.49–4.57 (fraction nos. 13–17) and 4.81–5.98 (fraction nos. 23–27).

EXAMPLE 7

Autoclaved *M. vaccae* Generates Cytotoxic CD8 T Cells Against *M. tuberculosis* Infected Macrophages This example illustrates the ability of killed *M. vaccae* to stimulate cytotoxic CD8 T cells which preferentially kill macrophages that have been infected with *M. tuberculosis*.

Mice were immunized by the intraperitoneal injection of 500 μg of killed *M. vaccae* which was prepared as described in Example 1. Two weeks after immunization, the spleen cells of immunized mice were passed through a CD8 T cell enrichment column (R&D Systems, St. Paul, Minn., USA). The spleen cells recovered from the column have been shown to be enriched up to 90% CD8 T cells. These T cells, as well as CD8 T cells from spleens of non-immunized mice, were tested for their ability to kill uninfected macrophages or macrophages which have been infected with *M. tuberculosis*.

Macrophages were obtained from the peritoneal cavity of mice five days after they have been given 1 ml of 3% thioglycolate intraperitoneally. The macrophages were infected overnight with *M. tuberculosis* at the ratio of 2 mycobacteria per macrophage. All macrophage preparations were labelled with $^{51}$ Chromium at 2 μci per $10^4$ macrophages. The macrophages were then cultured with CD8 T cells overnight (16 hours) at killer to target ratios of 30:1. Specific killing was detected by the release of $^{51}$ Chromium and expressed as % specific lysis, calculated as in Example 5.

The production of IFN-γ and its release into medium after 3 days of co-culture of CD8 T cells with macrophages was measured using an enzyme-linked immunosorbent assay (ELISA). ELISA plates were coated with a rat monoclonal antibody directed to mouse IFN-γ (Pharmigen, San Diego, Calif., USA) in PBS for 4 hours at 4° C. Wells were blocked with PBS containing 0.2% Tween 20 for 1 hour at room temperature. The plates were then washed four times in PBS containing 0.2% Tween 20, and samples diluted 1:2 in culture medium in the ELISA plates were incubated overnight at room temperature. The plates were again washed, and a biotinylated monoclonal rat anti-mouse IFN-γ antibody (Pharmigen), diluted to 1 μg/ml in PBS, was added to each well. The plates were then incubated for 1 hour at room temperature, washed, and horseradish peroxidase-coupled avidin D (Sigma A-3151) was added at a 1:4,000 dilution in PBS. After a further 1 hour incubation at room temperature, the plates were washed and OPD substrate added. The reaction was stopped after 10 min with 10% (v/v) HCl. The optical density was determined at 490 nm. Fractions that resulted in both replicates giving an OD two-fold greater than the mean OD from cells cultured in medium alone were considered positive.

As shown in Table 5, CD8 T cells from spleens of mice immunized with *M. vaccae* were cytotoxic for macrophages infected with *M. tuberculosis* and did not lyse uninfected macrophages. The CD8 T cells from non-immunized mice did not lyse macrophages. CD8 T cells from naive or non-immunized mice do produce IFN-γ when cocultured with infected macrophages. The amount of IFN-γ produced in coculture was greater with CD8 T cells derived from *M. vaccae* immunized mice.

TABLE 5

EFFECT WITH *M. TUBERCULOSIS* INFECTED MACROPHAGES

| CD8 T cells | % Specific Lysis | | IFN-g (ng/ml) | |
|---|---|---|---|---|
| | uninfected | infected | uninfected | infected |
| Control | 0 | 0 | 0.7 | 24.6 |
| *M. vaccae* Immunized | 0 | 95 | 2.2 | 43.8 |

EXAMPLE 8

DNA Cloning Strategy for the *M. vaccae* Antigens GV-23, GV-24, GV-25 and GV-26

*M. vaccae* (ATCC Number 15483) was grown in sterile Medium 90 at 37° C. for 4 days and harvested by centrifugation. Cells were resuspended in 1 ml Trizol (Gibco BRL, Life Technologies, Gaithersburg, Md.) and RNA extracted according to the standard manufacturer's protocol. *M. tuberculosis* strain H37Rv (ATCC Number 27294) was grown in sterile Middlebrooke 7H9 medium with Tween 8™ and oleic acid/albumin/dextrose/catalase additive (Difco Laboratories, Detroit, Mich.) at 37° C. and harvested under appropriate laboratory safety conditions. Cells were resuspended in 1 ml Trizol (Gibco BRL) and RNA extracted according to the manufacturer's standard protocol.

Total *M. tuberculosis* and *M. vaccae* RNA was depleted of 16S and 23S ribosomal RNA (rRNA) by hybridisation of the total RNA fraction to oligonucleotides AD10 and AD11 (SEQ ID NO: 81 and 82) complementary to *M. tuberculosis* rRNA. These oligonucleotides were designed from mycobacterial 16S rRNA sequences published by Bottger (*FEMS Microbiol. Lett.* 65:171–176, 1989) and from sequences deposited in the databanks. Depletion was done by hybridisation of total RNA to oligonucleotides AD10 and AD11 immobilised on nylon membranes (Hybond N, Amersham International, United Kingdom). Hybridisation was repeated until rRNA bands were not visible on ethidium bromide-stained agarose gels. An oligonucleotide, AD12 (SEQ ID NO: 83), consisting of 20 dATP-residues, was ligated to the 3' ends of the enriched mRNA fraction using RNA ligase. First strand cDNA synthesis was performed following standard protocols, using oligonucleotide AD7 (SEQ ID NO:84) containing a poly(dT) sequence.

The *M. tuberculosis* and *M. vaccae* cDNA was used as template for single-sided-specific PCR (3S-PCR). For this protocol, a degenerate oligonucleotide AD1 (SEQ ID NO:85) was designed based on conserved leader sequences and membrane protein sequences. After 30 cycles of amplification using primer AD1 as 5'-primer and AD7 as 3'-primer, products were separated on a urea/polyacrylamide gel. DNA bands unique to *M. vaccae* were excised and re-amplified using primers AD1 and AD7. After gel purification, bands were cloned into pGEM-T (Promega) and the base sequence determined.

Searches with the determined nucleotide and predicted amino acid sequences of band 12B21 (SEQ ID NOS: 86 and 87, respectively) showed homology to the pota gene of *E. coli* encoding the ATP-binding protein of the spermidine/putrescine ABC transporter complex published by Furuchi et al. (*Jnl. Biol. Chem.* 266: 20928–20933, 1991). The spermidine/putrescine transporter complex of *E. coli* consists of four genes and is a member of the ABC transporter family. The ABC (ATP-binding Cassette) transporters typically consist of four genes: an ATP-binding gene, a periplasmic, or substrate binding, gene and two transmembrane genes. The transmembrane genes encode proteins each characteristically having six membrane-spanning regions. Homologues (by similarity) of this ABC transporter have been identified in the genomes of *Haemophilus influenza* (Fleischmann et al. *Science* 269:496–512, 1995) and *Mycoplasma genitalium* (Fraser, et al. *Science*, 270:397–403, 1995).

An *M. vaccae* genomic DNA library constructed in BamH1-digested lambda ZAP Express (Stratagene) was probed with the radiolabelled 238 bp band 12B21 following standard protocols. A plaque was purified to purity by repetitive screening and a phagemid containing a 4.5 kb insert was identified by Southern blotting and hybridisation. The nucleotide sequence of the full-length *M. vaccae* homologue of pota (ATP-binding protein) was identified by subcloning of the 4.5 kb fragment and base sequencing. The gene consisted of 1449 bp including an untranslated 5' region of 320 bp containing putative −10 and −35 promoter elements. The nucleotide and predicted amino acid sequences of the *M. vaccae* pota homologue are provided in SEQ ID NOS:88 and 89, respectively.

The nucleotide sequence of the *M. vaccae* pota gene was used to design primers EV24 and EV25 (SEQ ID NO: 90 and 91) for expression cloning. The amplified DNA fragment was cloned into pProEX HT prokaryotic expression system (Gibco BRL) and expression in an appropriate *E. coli* host was induced by addition of 0.6 mM isopropylthio-β-galactoside (IPTG). The recombinant protein was named GV-23 and purified from inclusion bodies according to the manufacturer's protocol.

A 322 bp Sal1-BamH1 subclone at the 3'-end of the 4.5 kb insert described above showed homology to the potd gene, (periplasmic protein), of the spermidine/putrescine ABC transporter complex of *E. col*. The nucleotide sequence of this subclone is shown in SEQ ID NO:92. To identify the gene, the radiolabelled insert of this subclone was used to probe an *M. vaccae* genomic DNA library constructed in the Sal1-site of lambda Zap Express (Stratagene) following standard protocols. A clone was identified of which 1342 bp showed homology with the potd gene of *E. coli*. The potd homologue of *M. vaccae* was identified by sub-cloning and base sequencing. The determined nucleotide and predicted amino acid sequences are shown in SEQ ID NO: 93 and 94.

For expression cloning, primers EV26 and EV27 (SEQ ID NOS:95–96) were designed from the determined *M. vaccae* potd homologue. The amplified fragment was cloned into pProEX HT Prokaryotic expression system (Gibco BRL). Expression in an appropriate *E. coli* host was induced by addition of 0.6 mM IPTG and the recombinant protein named GV24. The recombinant antigen was purified from inclusion bodies according to the protocol of the supplier.

The ability of purified recombinant protein GV-23 and GV-24 to stimulate proliferation of T cells and interferon-production in human PBL was determined as described in Example 2. The results of these assays are provided in Table 6, wherein (−) indicates a lack of activity, (+/−) indicates polypeptides having a result less than twice higher than background activity of control media, (+) indicates polypeptides having activity two to four times above background, (++) indicates polypeptides having activity greater than four times above background, and (ND) indicates not determined.

TABLE 6

| | Donor G97005 | | Donor G97006 | | Donor G97007 | | Donor G97008 | | Donor G97009 | | Donor G97010 | |
|---|---|---|---|---|---|---|---|---|---|---|---|---|
| | Prolif | IFN-g | Prolif | IFN-g | Prolif | IFN-g | Prolif | IFN-g | Prolif | IFN-g | Prolif | IFN-g |
| GV-23 | ++ | ++ | ++ | ++ | + | + | ++ | ++ | + | − | + | ++ |
| GV-24 | ++ | + | ++ | + | ND | ND | + | +/− | + | +/− | +/− | ++ |

Base sequence adjacent to the *M. vaccae* potd gene-homologue was found to show homology to the potb gene of the spermidine/putrescine ABC transporter complex of *E. coli*, which is one of two transmembrane proteins in the ABC transporter complex. The *M. vaccae* potb homologue (referred to as GV-25) was identified through further subcloning and base sequencing. The determined nucleotide and predicted amino acid sequences for GV-25 are shown in SEQ ID NOS:97 and 98, respectively.

Further subcloning and base sequence analysis of the adjacent 509 bp failed to reveal significant homology to PotC, the second transmembrane protein of *E. coli*, and suggests that a second transmembrane protein is absent in the *M. vaccae* homologue of the ABC transporter. An open reading frame with homology to *M. tuberculosis* acetylCoA acetyl transferase, however, was identified starting 530 bp downstream of the transmembrane protein and the translated protein was named GV-26. The determined partial nucleotide sequence and predicted amino acid sequence for GV-26 are shown in SEQ ID NO:99 and 100.

EXAMPLE 9

Purification and Characterisation of Polypeptides from *M. vaccae* Culture Filtrate by Preparative Isoelectric Focusing and Preparative Polyacrylamide Gel Electrophoresis

*M. vaccae* soluble proteins were isolated from culture filtrate using preparative isoelectric focusing and preparative polyacrylamide gel electrophoresis as described below. Unless otherwise noted, all percentages in the following example are weight per volume.

*M. vaccae* (ATCC Number 15483) was cultured in 250 1 sterile Medium 90 which had been fractionated by ultrafiltration to remove all proteins of greater than 10 kDa molecular weight. The medium was centrifuged to remove the bacteria, and sterilised by filtration through a 0.45 m filter. The sterile filtrate was concentrated by ultrafiltration over a 10 kDa molecular weight cut-off membrane.

Proteins were isolated from the concentrated culture filtrate by precipitation with 10% trichloroacetic acid. The precipitated proteins were re-dissolved in 100 mM Tris.HCl pH 8.0. and re-precipitated by the addition of an equal volume of acetone. The acetone precipitate was dissolved in water, and proteins were re-precipitated by the addition of an equal volume of chloroform:methanol 2:1 (v/v). The chloroform:methanol precipitate was dissolved in water, and the solution was freeze-dried.

The freeze-dried protein was dissolved in iso-electric focusing buffer, containing 8 M deionised urea, 2% Triton X-100, 10 mM dithiothreitol and 2% ampholytes (pH 2.5–5.0). The sample was fractionated by preparative iso-electric focusing on a horizontal bed of Ultrodex gel at 8 watts constant power for 16 hours. Proteins were eluted from the gel bed fractions with water and concentrated by precipitation with 10% trichloroacetic acid.

Pools of fractions containing proteins of interest were identified by analytical polyacrylamide gel electrophoresis and fractionated by preparative polyacrylamide gel electrophoresis. Samples were fractionated on 12.5% SDS-PAGE gels, and electroblotted onto nitrocellulose membranes. Proteins were located on the membranes by staining with Ponceau Red, destained with water and eluted from the membranes with 40% acetonitrile/0.1 M ammonium bicarbonate pH 8.9 and then concentrated by lyophilisation.

Eluted proteins were assayed for their ability to induce proliferation and interferon-γ secretion from the peripheral blood lymphocytes of immune donors as detailed in Example 2. Proteins inducing a strong response in these assays were selected for further study.

Selected proteins were further purified by reversed-phase chromatography on a Vydac Protein C4 column, using a trifluoroacetic acid-acetonitrile system. Purified proteins were prepared for protein sequence determination by SDS-polyacrylamide gel electrophoresis, and electroblotted onto PVDF membranes. Protein sequences were determined as in Example 3. The proteins were named GV-40, GV-41, GV-42, GV-43 and GV-44. The determined N-terminal sequences for these polypeptides are shown in SEQ ID NOS: 101–105, respectively.

All of these amino acid sequences were compared to known amino acid sequences in the EMBL data base using TFASTA. No significant homologies were obtained with GV-40, GV42 and GV-44. GV-41 had similarity to a putative ribosome recycling factor from *M. tuberculosis*, a protein responsible for the release of ribosomes from mRNA at the termination of protein biosynthesis. GV-43 showed homology (by similarity) to a previously identified unknown *M. tuberculosis* and *M. leprae* protein.

Although the present invention has been described in some detail by way of illustration and example for purposes of clarity of understanding, changes and modifications can be carried out without departing from the scope of the invention which is intended to be limited only by the scope of the appended claims.

---

We claim:

1. An isolated and purified *Mycobacterium vaccae* polypeptide comprising a sequence selected from the group consisting of: SEQ ID NOS: 56–59, 63–65, 101, 103 and 105.

2. A pharmaceutical composition comprising at least one isolated polypeptide according to claim 1, and a physiologically acceptable carrier.

3. A vaccine comprising at least one isolated polypeptide according to claim 1, and a non-specific immune response amplifier.

4. A vaccine according to claim 3 wherein the non-specific immune response amplifier is an adjuvant.

5. A vaccine according to claim 3 wherein the non-specific immune response amplifier comprises delipidated *M. vaccae* cells.

6. A vaccine according to claim 3 wherein the non-specific immune response amplifier comprises culture filtrate from *M. vaccae*.

* * * * *

UNITED STATES PATENT AND TRADEMARK OFFICE
CERTIFICATE OF CORRECTION

PATENT NO. : 6,001,361
DATED : December 14, 1999
INVENTOR(S) : Paul Tan, Jun Hiyama, Elizabeth Visser, Margot skinner, Lida Scott, and Ross Prestidge Page 1 of 1

It is certified that error appears in the above-identified patent and that said Letters Patent is hereby corrected as shown below:

Column 5,
Line 28, replace "synthesized. and the" with -- synthesized, and the --

Column 14,
Line 56, replace "to eat" with -- to heat --

Column 17,
Line 3, replace "Vydac C8" with -- Vydac C18 --
Line 14, replace "ID NOS: ,2 and 3," with -- ID NOS: 1, 2 and 3, --
Line 20, replace "SEQ ID NO:" with -- SEQ ID NOS:"

Column 19,
Line 19, replace "Filtrate Be" with -- Filtrate By --

Column 21,
Line 34, replace " genes each" with -- genes, each --

Column 22,
Line 2, replace "A AhoI" with -- X AhoI --

Column 23,
Line 7, replace "AhoI" with -- XhoI --
Line 54, replace "SIQ" with -- SEQ --

Column 24,
Line 47, replace "outcr membrane" with -- outer membrane --

Signed and Sealed this

Twenty-fifth Day of September, 2001

*Attest:*

*Nicholas P. Godici*

NICHOLAS P. GODICI
*Attesting Officer*   *Acting Director of the United States Patent and Trademark Office*

SEQUENCE LISTING (1) GENERAL INFORMATION:

(iii) NUMBER OF SEQUENCES: 106

(2) INFORMATION FOR SEQ ID NO:1:

(i) SEQUENCE CHARACTERISTICS:
      (A) LENGTH: 25 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

Ala Pro Val Gly Pro Gly Xaa Ala Ala Tyr Val Gln Gln Val Pro Asp
1               5                   10                  15

Gly Pro Gly Ser Val Gln Gly Met Ala
            20                  25

(2) INFORMATION FOR SEQ ID NO:2:

```
    (i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

Met Xaa Asp Gln Leu Lys Val Asn Asp Asp
1               5                   10

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Met Xaa Pro Val Pro Val Ala Thr Ala Ala Tyr
1               5                   10

(2) INFORMATION FOR SEQ ID NO:4:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Thr Pro Ala Pro Ala Pro Pro Tyr Val Asp His Val Glu Gln Ala
1               5                   10                  15

Lys Phe Gly Asp Leu
            20

(2) INFORMATION FOR SEQ ID NO:5:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Gln Ala Phe Asn Ala Asp Ala Tyr Ala Phe Ala Lys Arg Glu Lys
1               5                   10                  15

Val Ser Leu Ala Pro Gly Val Pro Xaa Val Phe Glu Thr
            20                  25

(2) INFORMATION FOR SEQ ID NO:6:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:
```

Met Ala Asp Pro Asn Xaa Ala Ile Leu Gln Val Ser Lys Thr Thr Arg
1               5                   10                  15

Gly Gly Gln Ala Ala
            20

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Met Pro Ile Leu Gln Val Ser Gln Thr Gly Arg
1               5                   10

(2) INFORMATION FOR SEQ ID NO:8:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Met Xaa Asp Pro Ile Xaa Leu Gln Leu Gln Val Ser Ser Thr
1               5                   10

(2) INFORMATION FOR SEQ ID NO:9:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Lys Ala Thr Tyr Val Gln Gly Gly Leu Gly Arg Ile Glu Ala Arg Val
1               5                   10                  15

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Lys Xaa Gly Leu Ala Asp Leu Ala Pro
1               5

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (ix) FEATURE:
            (A) NAME/KEY: Other
            (B) LOCATION: 12...12
            (D) OTHER INFORMATION: Residue can be either Glu or Ile (xi) SEQUENCE DESCRIPTION: SEQ ID NO:11:

Lys Xaa Tyr Ala Leu Ala Leu Met Ser Ala Val Xaa Ala Ala
1               5                   10

(2) INFORMATION FOR SEQ ID NO:12:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:12:

Lys Asn Pro Gln Val Ser Asp Glu Leu Xaa Thr
1               5                   10

(2) INFORMATION FOR SEQ ID NO:13:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:13:

Ala Pro Ala Pro Ala Ala Pro Ala Xaa Gly Asp Pro Ala Ala Val Val
1               5                   10                  15

Ala Ala Asn Ser Thr
            20

(2) INFORMATION FOR SEQ ID NO:14:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:14:

Glu Ala Glu Val Xaa Tyr Leu Gly Gln Pro Gly Glu Leu Val Asn
1               5                   10                  15

(2) INFORMATION FOR SEQ ID NO:15:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: protein (ix) FEATURE:
            (A) NAME/KEY: Other
            (B) LOCATION: 2...2
            (D) OTHER INFORMATION: Residue can be either Gly or Ala (A) NAME/KEY: Other
            (B) LOCATION: 15...15

-continued (D) OTHER INFORMATION: Residue can be either Pro or Ala (xi) SEQUENCE DESCRIPTION: SEQ ID NO:15:

Ala Xaa Val Val Pro Pro Xaa Gly Pro Pro Ala Pro Gly Ala Xaa
 1               5                  10                  15

(2) INFORMATION FOR SEQ ID NO:16:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

Ala Pro Ala Pro Asp Leu Gln Gly Pro Leu Val Ser Thr Leu Ser
 1               5                  10                  15

(2) INFORMATION FOR SEQ ID NO:17:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

Ala Thr Pro Asp Trp Ser Gly Arg Tyr Thr Val Val Thr Phe Ala Ser
 1               5                  10                  15

Asp Lys Leu Gly Thr Ser Val Ala Ala
                20                  25

(2) INFORMATION FOR SEQ ID NO:18:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 15...15
        (D) OTHER INFORMATION: Residue can be either Ala or Arg (A) NAME/KEY: Other
        (B) LOCATION: 23...23
        (D) OTHER INFORMATION: Residue can be either Val or Leu (xi) SEQUENCE DESCRIPTION: SEQ ID NO:18:

Ala Pro Pro Tyr Asp Asp Arg Gly Tyr Val Asp Ser Thr Ala Xaa Xaa
 1               5                  10                  15

Ala Ser Pro Pro Thr Leu Xaa Val Val
                20                  25

(2) INFORMATION FOR SEQ ID NO:19:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein

```
        (xi) SEQUENCE DESCRIPTION: SEQ ID NO:19:

Glu Pro Glu Gly Val Ala Pro Pro
1               5

(2) INFORMATION FOR SEQ ID NO:20:

(i) SEQUENCE CHARACTERISTICS:
         (A) LENGTH: 25 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:20:

Glu Pro Ala Gly Ile Pro Ala Gly Phe Pro Asp Val Ser Ala Tyr Ala
1               5                   10                  15

Ala Val Asp Pro Xaa Xaa Tyr Val Val
            20                  25

(2) INFORMATION FOR SEQ ID NO:21:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:21:

Ala Pro Val Gly Pro Gly Xaa Ala Ala Tyr Val Gln Gln Val Pro
1               5                   10                  15

(2) INFORMATION FOR SEQ ID NO:22:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:22:

Phe Ser Arg Pro Gly Leu Pro Val Glu Tyr Leu Asp Val Phe Ser
1               5                   10                  15

(2) INFORMATION FOR SEQ ID NO:23:

(i) SEQUENCE CHARACTERISTICS:
         (A) LENGTH: 19 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:23:

Phe Ser Arg Pro Gly Leu Pro Val Glu Tyr Leu Met Val Pro Ser Pro
1               5                   10                  15

Ser Met Gly (2) INFORMATION FOR SEQ ID NO:24:

(i) SEQUENCE CHARACTERISTICS:
         (A) LENGTH: 15 amino acids
```

```
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

Phe Ser Arg Pro Gly Leu Pro Val Glu Tyr Leu Met Val Pro Ser
1               5                   10                  15

(2) INFORMATION FOR SEQ ID NO:25:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:25:

Xaa Xaa Thr Gly Leu His Arg Leu Arg Met Met Val Pro Asn
1               5                   10

(2) INFORMATION FOR SEQ ID NO:26:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 16...16
        (D) OTHER INFORMATION: Residue can be either Ser or Val (A) NAME/KEY: Other
        (B) LOCATION: 17...17
        (D) OTHER INFORMATION: Residue can be either Gln or Val (xi) SEQUENCE DESCRIPTION: SEQ ID NO:26:

Val Pro Ala Asp Pro Val Gly Ala Ala Ala Gln Ala Glu Pro Ala Xaa
1               5                   10                  15

Xaa Arg Ile Asp
        20

(2) INFORMATION FOR SEQ ID NO:27:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 4...4
        (D) OTHER INFORMATION: Residue can be either Tyr or Pro (A) NAME/KEY: Other
        (B) LOCATION: 8...8
        (D) OTHER INFORMATION: Residue can be either Val or Gly (A) NAME/KEY: Other
        (B) LOCATION: 9...9
        (D) OTHER INFORMATION: Residue can be either Ile or Tyr (xi) SEQUENCE DESCRIPTION: SEQ ID NO:27:
```

```
Asp Pro Xaa Xaa Asp Ile Glu Xaa Xaa Phe Ala Arg Gly Thr
  1               5                  10
```

(2) INFORMATION FOR SEQ ID NO:28:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

```
Ala Pro Ser Leu Ser Val Ser Asp Tyr Ala Arg Asp Ala Gly Phe
  1               5                  10                  15
```

(2) INFORMATION FOR SEQ ID NO:29:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 2...2
        (D) OTHER INFORMATION: Residue can be either Leu or Pro (xi) SEQUENCE DESCRIPTION: SEQ ID NO:29:

```
Xaa Xaa Leu Ala Xaa Ala Xaa Leu Gly Xaa Thr Val Asp Ala Asp Gln
  1               5                  10                  15
```

(2) INFORMATION FOR SEQ ID NO:30:

(i) SEQUENCE CHARACTERISTICS:
        (A) LENGTH: 330 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:30:

```
Met Lys Phe Val Asp Arg Phe Arg Gly Ala Val Ala Gly Met Leu Arg
  1               5                  10                  15

Arg Leu Val Val Glu Ala Met Gly Val Ala Leu Leu Ser Ala Leu Ile
                 20                  25                  30

Gly Val Val Gly Ser Ala Pro Ala Glu Ala Phe Ser Arg Pro Gly Leu
             35                  40                  45

Pro Val Glu Tyr Leu Gln Val Pro Ser Pro Ser Met Gly Arg Asp Ile
         50                  55                  60

Lys Val Gln Phe Gln Asn Gly Gly Ala Asn Ser Pro Ala Leu Tyr Leu
 65                  70                  75                  80

Leu Asp Gly Leu Arg Ala Gln Asp Asp Phe Ser Gly Trp Asp Ile Asn
                 85                  90                  95

Thr Thr Ala Phe Glu Trp Tyr Tyr Gln Ser Gly Ile Ser Val Val Met
            100                 105                 110

Pro Val Gly Gly Gln Ser Ser Phe Tyr Ser Asp Trp Tyr Ser Pro Ala
            115                 120                 125

Cys Gly Lys Ala Gly Cys Gln Thr Tyr Lys Trp Glu Thr Phe Leu Thr
            130                 135                 140
```

```
Ser Glu Leu Pro Glu Tyr Leu Gln Ser Asn Lys Gln Ile Lys Pro Thr
145                 150                 155                 160

Gly Ser Ala Ala Val Gly Leu Ser Met Ala Gly Leu Ser Ala Leu Thr
                165                 170                 175

Leu Ala Ile Tyr His Pro Asp Gln Phe Ile Tyr Val Gly Ser Met Ser
            180                 185                 190

Gly Leu Leu Asp Pro Ser Asn Ala Met Gly Pro Ser Leu Ile Gly Leu
        195                 200                 205

Ala Met Gly Asp Ala Gly Gly Tyr Lys Ala Ala Asp Met Trp Gly Pro
210                 215                 220

Ser Thr Asp Pro Ala Trp Lys Arg Asn Asp Pro Thr Val Asn Val Gly
225                 230                 235                 240

Thr Leu Ile Ala Asn Asn Thr Arg Ile Trp Met Tyr Cys Gly Asn Gly
                245                 250                 255

Lys Pro Thr Glu Leu Gly Asn Asn Leu Pro Ala Lys Leu Leu Glu
            260                 265                 270

Gly Leu Val Arg Thr Ser Asn Ile Lys Phe Gln Asp Gly Tyr Asn Ala
        275                 280                 285

Gly Gly Gly His Asn Ala Val Phe Asn Phe Pro Asp Ser Gly Thr His
290                 295                 300

Ser Trp Glu Tyr Trp Gly Glu Gln Leu Asn Asp Met Lys Pro Asp Leu
305                 310                 315                 320

Gln Gln Tyr Leu Gly Ala Thr Pro Gly Ala
                325                 330

(2) INFORMATION FOR SEQ ID NO:31:

(i) SEQUENCE CHARACTERISTICS:
        (A) LENGTH: 327 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

Met Ile Asp Val Ser Gly Lys Ile Arg Ala Trp Gly Arg Trp Leu Leu
1               5                   10                  15

Val Gly Ala Ala Ala Thr Leu Pro Ser Leu Ile Ser Leu Ala Gly Gly
                20                  25                  30

Ala Ala Thr Ala Ser Ala Phe Ser Arg Pro Gly Leu Pro Val Glu Tyr
            35                  40                  45

Leu Gln Val Pro Ser Glu Ala Met Gly Arg Thr Ile Lys Val Gln Phe
50                  55                  60

Gln Asn Gly Gly Asn Gly Ser Pro Ala Val Tyr Leu Leu Asp Gly Leu
65                  70                  75                  80

Arg Ala Gln Asp Asp Tyr Asn Gly Trp Asp Ile Asn Thr Ser Ala Phe
                85                  90                  95

Glu Trp Tyr Tyr Gln Ser Gly Leu Ser Val Val Met Pro Val Gly Gly
            100                 105                 110

Gln Ser Ser Phe Tyr Ser Asp Trp Tyr Ser Pro Ala Cys Gly Lys Ala
        115                 120                 125

Gly Cys Thr Thr Tyr Lys Trp Glu Thr Phe Leu Thr Ser Glu Leu Pro
130                 135                 140

Lys Trp Leu Ser Ala Asn Arg Ser Val Lys Ser Thr Gly Ser Ala Val
145                 150                 155                 160
```

```
Val Gly Leu Ser Met Ala Gly Ser Ser Ala Leu Ile Leu Ala Ala Tyr
            165                 170                 175

His Pro Asp Gln Phe Ile Tyr Ala Gly Ser Leu Ser Ala Leu Met Asp
            180                 185                 190

Ser Ser Gln Gly Ile Glu Pro Gln Leu Ile Gly Leu Ala Met Gly Asp
            195                 200                 205

Ala Gly Gly Tyr Lys Ala Ala Asp Met Trp Gly Pro Pro Asn Asp Pro
            210                 215                 220

Ala Trp Gln Arg Asn Asp Pro Ile Leu Gln Ala Gly Lys Leu Val Ala
225                 230                 235                 240

Asn Asn Thr His Leu Trp Val Tyr Cys Gly Asn Gly Thr Pro Ser Glu
                245                 250                 255

Leu Gly Gly Thr Asn Val Pro Ala Glu Phe Leu Glu Asn Phe Val His
                260                 265                 270

Gly Ser Asn Leu Lys Phe Gln Asp Ala Tyr Asn Gly Ala Gly Gly His
                275                 280                 285

Asn Ala Val Phe Asn Leu Asn Ala Asp Gly Thr His Ser Trp Glu Tyr
290                 295                 300

Trp Gly Ala Gln Leu Asn Ala Met Lys Pro Asp Leu Gln Asn Thr Leu
305                 310                 315                 320

Met Ala Val Pro Arg Ser Gly
                325
```

(2) INFORMATION FOR SEQ ID NO:32:

(i) SEQUENCE CHARACTERISTICS:
        (A) LENGTH: 338 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

```
Met Gln Leu Val Asp Arg Val Arg Gly Ala Val Thr Gly Met Ser Arg
1                   5                   10                  15

Arg Leu Val Val Gly Ala Val Gly Ala Ala Leu Val Ser Gly Leu Val
                20                  25                  30

Gly Ala Val Gly Gly Thr Ala Thr Ala Gly Ala Phe Ser Arg Pro Gly
                35                  40                  45

Leu Pro Val Glu Tyr Leu Gln Val Pro Ser Pro Ser Met Gly Arg Asp
            50                  55                  60

Ile Lys Val Gln Phe Gln Ser Gly Gly Ala Asn Ser Pro Ala Leu Tyr
65                  70                  75                  80

Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
            100                 105                 110

Met Pro Val Gly Gly Gln Ser Ser Phe Tyr Ser Asp Trp Tyr Gln Pro
            115                 120                 125

Ala Cys Gly Lys Ala Gly Cys Gln Thr Tyr Lys Trp Glu Thr Phe Leu
            130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
```

-continued

```
                 180                 185                 190
Ser Gly Leu Leu Asp Pro Ser Gln Ala Met Gly Pro Thr Leu Ile Gly
                 195                 200                 205

Leu Ala Met Gly Asp Ala Gly Gly Tyr Lys Ala Ser Asp Met Trp Gly
        210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Asn Asn Leu Pro Ala Lys Phe Leu
        260                 265                 270

Glu Gly Phe Val Arg Thr Ser Asn Ile Lys Phe Gln Asp Ala Tyr Asn
                275                 280                 285

Ala Gly Gly His Asn Gly Val Phe Asp Phe Pro Asp Ser Gly Thr
        290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                325                 330                 335

Gly Ala
```

(2) INFORMATION FOR SEQ ID NO:33:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

```
Met Thr Asp Val Ser Arg Lys Ile Arg Ala Trp Gly Arg Arg Leu Met
 1               5                  10                  15

Ile Gly Thr Ala Ala Val Val Leu Pro Gly Leu Val Gly Leu Ala
                20                  25                  30

Gly Gly Ala Ala Thr Ala Gly Ala Phe Ser Arg Pro Gly Leu Pro Val
        35                  40                  45

Glu Tyr Leu Gln Val Pro Ser Pro Ser Met Gly Arg Asp Ile Lys Val
 50                  55                  60

Gln Phe Gln Ser Gly Gly Asn Asn Ser Pro Ala Val Tyr Leu Leu Asp
 65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
            100                 105                 110

Gly Gly Gln Ser Ser Phe Tyr Ser Asp Trp Tyr Ser Pro Ala Cys Gly
        115                 120                 125

Lys Ala Gly Cys Gln Thr Tyr Lys Trp Glu Thr Phe Leu Thr Ser Glu
130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ser Ala Met Ile Leu Ala
                165                 170                 175

Ala Tyr His Pro Gln Gln Phe Ile Tyr Ala Gly Ser Leu Ser Ala Leu
            180                 185                 190
```

-continued

```
Leu Asp Pro Ser Gln Gly Met Gly Pro Ser Leu Ile Gly Leu Ala Met
        195                 200                 205

Gly Asp Ala Gly Gly Tyr Lys Ala Ala Asp Met Trp Gly Pro Ser Ser
210                 215                 220

Asp Pro Ala Trp Glu Arg Asn Asp Pro Thr Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
        260                 265                 270

Val Arg Ser Ser Asn Leu Lys Phe Gln Asp Ala Tyr Asn Ala Ala Gly
        275                 280                 285

Gly His Asn Ala Val Phe Asn Phe Pro Pro Asn Gly Thr His Ser Trp
        290                 295                 300

Glu Tyr Trp Gly Ala Gln Leu Asn Ala Met Lys Gly Asp Leu Gln Ser
305                 310                 315                 320

Ser Leu Gly Ala Gly
                325
```

(2) INFORMATION FOR SEQ ID NO:34:

(i) SEQUENCE CHARACTERISTICS:
        (A) LENGTH: 338 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:34:

```
Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
                20                  25                  30

Gly Ala Val Gly Gly Thr Ala Thr Ala Gly Ala Phe Ser Arg Pro Gly
            35                  40                  45

Leu Pro Val Glu Tyr Leu Gln Val Pro Ser Pro Ser Met Gly Arg Asp
        50                  55                  60

Ile Lys Val Gln Phe Gln Ser Gly Gly Ala Asn Ser Pro Ala Leu Tyr
65                  70                  75                  80

Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
            100                 105                 110

Met Pro Val Gly Gly Gln Ser Ser Phe Tyr Ser Asp Trp Tyr Gln Pro
        115                 120                 125

Ala Cys Gly Lys Ala Gly Cys Gln Thr Tyr Lys Trp Glu Thr Phe Leu
130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
        195                 200                 205

Leu Ala Met Gly Asp Ala Gly Gly Tyr Lys Ala Ser Asp Met Trp Gly
```

```
            210                 215                 220
Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
                260                 265                 270

Glu Gly Phe Val Arg Thr Ser Asn Ile Lys Phe Gln Asp Ala Tyr Asn
                275                 280                 285

Ala Gly Gly His Asn Gly Val Phe Asp Phe Pro Asp Ser Gly Thr
290                 295                 300

His Ser Trp Glu Tyr Trp Gly Ala Gln Leu Asn Ala Met Lys Pro Asp
305                 310                 315                 320

Leu Gln Arg Ala Leu Gly Ala Thr Pro Asn Thr Gly Pro Ala Pro Gln
                325                 330                 335

Gly Ala
```

(2) INFORMATION FOR SEQ ID NO:35:

(i) SEQUENCE CHARACTERISTICS:
        (A) LENGTH: 323 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

```
Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
                20                  25                  30

Gly Gly Ala Ala Thr Ala Gly Ala Phe Ser Arg Pro Gly Leu Pro Val
                35                  40                  45

Glu Tyr Leu Gln Val Pro Ser Pro Ser Met Gly Arg Asp Ile Lys Val
50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
                100                 105                 110

Gly Gly Gln Ser Ser Phe Tyr Ser Asp Trp Tyr Ser Pro Ala Cys Gly
                115                 120                 125

Lys Ala Gly Cys Gln Thr Tyr Lys Trp Glu Thr Leu Leu Thr Ser Glu
130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ala Met Ile Leu Ala
                165                 170                 175

Ala Tyr His Pro Gln Gln Phe Ile Tyr Ala Gly Ser Leu Ser Ala Leu
                180                 185                 190

Leu Asp Pro Ser Gln Gly Met Gly Leu Ile Gly Leu Ala Met Gly Asp
                195                 200                 205

Ala Gly Gly Tyr Lys Ala Ala Asp Met Trp Gly Pro Ser Ser Asp Pro
210                 215                 220
```

-continued

```
Ala Trp Glu Arg Asn Asp Pro Thr Gln Gln Ile Pro Lys Leu Val Ala
225                 230                 235                 240

Asn Asn Thr Arg Leu Trp Val Tyr Cys Gly Asn Gly Thr Pro Asn Glu
                245                 250                 255

Leu Gly Gly Ala Asn Ile Pro Ala Glu Phe Leu Glu Asn Phe Val Arg
            260                 265                 270

Ser Ser Asn Leu Lys Phe Gln Asp Ala Tyr Lys Pro Ala Gly Gly His
        275                 280                 285

Asn Ala Val Phe Asn Phe Pro Pro Asn Gly Thr His Ser Trp Glu Tyr
290                 295                 300

Trp Gly Ala Gln Leu Asn Ala Met Lys Gly Asp Leu Gln Ser Ser Leu
305                 310                 315                 320

Gly Ala Gly
```

(2) INFORMATION FOR SEQ ID NO:36:

(i) SEQUENCE CHARACTERISTICS:
        (A) LENGTH: 333 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:36:

```
Met Lys Phe Leu Gln Gln Met Arg Lys Leu Phe Gly Leu Ala Ala Lys
1               5                   10                  15

Phe Pro Ala Arg Leu Thr Ile Ala Val Ile Gly Thr Ala Leu Leu Ala
                20                  25                  30

Gly Leu Val Gly Val Val Gly Asp Thr Ala Ile Ala Val Ala Phe Ser
            35                  40                  45

Lys Pro Gly Leu Pro Val Glu Tyr Leu Gln Val Pro Ser Pro Ser Met
        50                  55                  60

Gly His Asp Ile Lys Ile Gln Phe Gln Gly Gly Gln His Ala Val
65                  70                  75                  80

Tyr Leu Leu Asp Gly Leu Arg Ala Gln Glu Asp Tyr Asn Gly Trp Asp
                85                  90                  95

Ile Asn Thr Pro Ala Phe Glu Glu Tyr Tyr His Ser Gly Leu Ser Val
            100                 105                 110

Ile Met Pro Val Gly Gly Gln Ser Ser Phe Tyr Ser Asn Trp Tyr Gln
        115                 120                 125

Pro Ser Gln Gly Asn Gly Gln His Tyr Thr Tyr Lys Trp Glu Thr Phe
    130                 135                 140

Leu Thr Gln Glu Met Pro Ser Trp Leu Gln Ala Asn Lys Asn Val Leu
145                 150                 155                 160

Pro Thr Gly Asn Ala Ala Val Gly Leu Ser Met Ser Gly Ser Ser Ala
                165                 170                 175

Leu Ile Leu Ala Ser Tyr Tyr Pro Gln Gln Phe Pro Tyr Ala Ala Ser
            180                 185                 190

Leu Ser Gly Phe Leu Asn Pro Ser Glu Gly Trp Trp Pro Thr Met Ile
        195                 200                 205

Gly Leu Ala Met Asn Asp Ser Gly Gly Tyr Asn Ala Asn Ser Met Trp
    210                 215                 220

Gly Pro Ser Thr Asp Pro Ala Trp Lys Arg Asn Asp Pro Met Val Gln
225                 230                 235                 240

Ile Pro Arg Leu Val Ala Asn Asn Thr Arg Ile Trp Val Tyr Cys Gly
                245                 250                 255
```

```
Asn Gly Ala Pro Asn Glu Leu Gly Gly Asp Asn Ile Pro Ala Lys Phe
            260                 265                 270

Leu Glu Ser Leu Thr Leu Ser Thr Asn Glu Ile Phe Gln Asn Thr Tyr
        275                 280                 285

Ala Ala Ser Gly Gly Arg Asn Gly Val Phe Asn Phe Pro Pro Asn Gly
        290                 295                 300

Thr His Ser Trp Pro Tyr Trp Asn Gln Gln Leu Val Ala Met Lys Pro
305                 310                 315                 320

Asp Ile Gln Gln Ile Leu Asn Gly Ser Asn Asn Asn Ala
                325                 330
```

(2) INFORMATION FOR SEQ ID NO:37:

(i) SEQUENCE CHARACTERISTICS:
        (A) LENGTH: 340 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

```
Met Thr Phe Phe Glu Gln Val Arg Arg Leu Arg Ser Ala Ala Thr Thr
  1                 5                  10                  15

Leu Pro Arg Arg Val Ala Ile Ala Ala Met Gly Ala Val Leu Val Tyr
             20                  25                  30

Gly Leu Val Gly Thr Phe Gly Gly Pro Ala Thr Ala Gly Ala Phe Ser
             35                  40                  45

Arg Pro Gly Leu Pro Val Glu Tyr Leu Gln Val Pro Ser Ala Ser Met
 50                  55                  60

Gly Arg Asp Ile Lys Val Gln Phe Gln Gly Gly Pro His Ala Val
 65                  70                  75                  80

Tyr Leu Leu Asp Gly Leu Arg Ala Gln Asp Asp Tyr Asn Gly Trp Asp
                 85                  90                  95

Ile Asn Thr Pro Ala Phe Glu Glu Tyr Tyr Gln Ser Gly Leu Ser Val
            100                 105                 110

Ile Met Pro Val Gly Gly Gln Ser Ser Phe Tyr Thr Asp Trp Tyr Gln
            115                 120                 125

Pro Ser Gln Ser Asn Gly Gln Asn Tyr Thr Tyr Lys Trp Glu Thr Phe
        130                 135                 140

Leu Thr Arg Glu Met Pro Ala Trp Leu Gln Ala Asn Lys Gly Val Ser
145                 150                 155                 160

Pro Thr Gly Asn Ala Ala Val Gly Leu Ser Met Ser Gly Gly Ser Ala
                165                 170                 175

Leu Ile Leu Ala Ala Tyr Tyr Pro Gln Gln Phe Pro Tyr Ala Ala Ser
            180                 185                 190

Leu Ser Gly Phe Leu Asn Pro Ser Glu Gly Trp Trp Pro Thr Leu Ile
        195                 200                 205

Gly Leu Ala Met Asn Asp Ser Gly Gly Tyr Asn Ala Asn Ser Met Trp
        210                 215                 220

Gly Pro Ser Ser Asp Pro Ala Trp Lys Arg Asn Asp Pro Met Val Gln
225                 230                 235                 240

Ile Pro Arg Leu Val Ala Asn Asn Thr Arg Ile Trp Val Tyr Cys Gly
                245                 250                 255

Asn Gly Thr Pro Ser Asp Leu Gly Gly Asp Asn Ile Pro Ala Lys Phe
            260                 265                 270
```

```
Leu Glu Gly Leu Thr Leu Arg Thr Asn Gln Thr Phe Arg Asp Thr Tyr
        275                 280                 285

Ala Ala Asp Gly Gly Arg Asn Gly Val Phe Asn Phe Pro Pro Asn Gly
        290                 295                 300

Thr His Ser Trp Pro Tyr Trp Asn Glu Gln Leu Val Ala Met Lys Ala
305                 310                 315                 320

Asp Ile Gln His Val Leu Asn Gly Ala Thr Pro Pro Ala Ala Pro Ala
                325                 330                 335

Ala Pro Ala Ala
        340

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:38:

AGCGGCTGGG ACATCAACAC                                              20

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:39:

CAGACGCGGG TGTTGTTGGC                                              20

(2) INFORMATION FOR SEQ ID NO:40:

(i) SEQUENCE CHARACTERISTICS:
        (A) LENGTH: 1211 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:40:

GGTACCGGAA GCTGGAGGAT TGACGGTATG AGACTTCTTG ACAGGATTCG TGGGCCTTGG    60

GCACGCCGTT TCGGCGTCGT GGCTGTCGCG ACAGCGATGA TGCCTGCTTT GGTGGGCCTG   120

GCTGGAGGGT CGGCGACCGC CGGAGCATTC TCCCGGCCAG GTCTGCCGGT GGAGTACCTG   180

ATGGTGCCTT CGCCGTCGAT GGGGCGCGAC ATCAAGATCC AGTTCCAGAG CGGTGGCGAG   240

AACTCGCCGG CTCTCTACCT GCTCGACGGC CTGCGTGCGC AGGAGGACTT CAACGGCTGG   300

GACATCAACA CTCAGGCTTT CGAGTGGTTC CTCGACAGCG GCATCTCCGT GGTGATGCCG   360

GTCGGTGGCC AGTCCAGCTT CTACACCGAC TGGTACGCCC CGCCCGTAA CAAGGGCCCG    420

ACCGTGACCT ACAAGTGGGA GACCTTCCTG ACCCAGGAGC TCCCGGGCTG GCTGCAGGCC   480

AACCGCGCGG TCAAGCCGAC CGGCAGCGGC CCTGTCGGTC TGTCGATGGC GGGTTCGGCC   540

GCGCTGAACC TGGCGACCTG GCACCCGGAG CAGTTCATCT ACGCGGGCTC GATGTCCGGC   600

TTCCTGAACC CCTCCGAGGG CTGGTGGCCG TTCCTGATCA ACATCTCGAT GGGTGACGCC   660
```

```
GGCGGCTTCA AGGCCGACGA CATGTGGGGC AAGACCGAGG GGATCCCAAC AGCGGTTGGA        720

CAGCGCAACG ATCCGATGCT GAACATCCCG ACCCTGGTCG CCAACAACAC CCGTATCTGG        780

GTCTACTGCG GTAACGGCCA GCCCACCGAG CTCGGCGGCG GCGACCTGCC CGCCACGTTC        840

CTCGAAGGTC TGACCATCCG CACCAACGAG ACCTTCCGCG ACAACTACAT CGCCGCGGGT        900

GGCCACAACG GTGTGTTCAA CTTCCCGGCC AACGGCACGC ACAACTGGGC GTACTGGGGT        960

CGCGAGCTGC AGGCGATGAA GCCTGACCTG CAGGCGCACC TTCTCTGACG GTTGCACGAA       1020

ACGAAGCCCC CGGCCGATTG CGGCCGAGGG TTTCGTCGTC CGGGGCTACT GTGGCCGACA       1080

TAACCGAAAT CAACGCGATG GTGGCTCATC AGGAACGCCG AGGGGTCAT TGCGCTACGA        1140

CACGAGGTGG GCGAGCAATC CTTCCTGCCC GACGGAGAGG TCAACATCCA CGTCGAGTAC       1200

TCCAGCGTGA A                                                           1211

(2) INFORMATION FOR SEQ ID NO:41:

(i) SEQUENCE CHARACTERISTICS:
        (A) LENGTH: 485 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:41:

AGCGGCTGGG ACATCAACAC CGCCGCCTTC GAGTGGTACG TCGACTCGGG TCTCGCGGTG         60

ATCATGCCCG TCGGCGGGCA GTCCAGCTTC TACAGCGACT GGTACAGCCC GGCCTGCGGT        120

AAGGCCGGCT GCCAGACCTA CAAGTGGGAG ACGTTCCTGA CCCAGGAGCT GCCGGCCTAC        180

CTCGCCGCCA ACAAGGGGGT CGACCCGAAC CGCAACGCGG CCGTCGGTCT GTCCATGGCC        240

GGTTCGGCGG CGCTGACGCT GGCGATCTAC CACCCGCAGC AGTTCCAGTA CGCCGGGTCG        300

CTGTCGGGCT ACCTGAACCC GTCCGAGGGG TGGTGGCCGA TGCTGATCAA CATCTCGATG        360

GGTGACGCGG GCGGCTACAA GGCCAACGAC ATGTGGGGTC CACCGAAGGA CCCGAGCAGC        420

GCCTGGAAGC GCAACGACCC GATGGTCAAC ATCGGCAAGC TGGTGGCCAA CAACACCCCC        480

CTCTC                                                                   485

(2) INFORMATION FOR SEQ ID NO:42:

(i) SEQUENCE CHARACTERISTICS:
        (A) LENGTH: 1052 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:42:

GTTGATGAGA AAGGTGGGTT GTTTGCCGTT ATGAAGTTCA CAGAGAAGTG GCGGGGCTCC         60

GCAAAGGCGG CGATGCACCG GGTGGGCGTT GCCGATATGG CCGCCGTTGC GCTGCCCGGA        120

CTGATCGGCT TCGCCGGGGG TTCGGCAACG GCCGGGGCAT TCTCCCGGCC CGGTCTTCCT        180

GTCGAGTACC TCGACGTGTT CTCGCCGTCA ATGGGCCGCG ACATCCGGGT CCAGTTCCAG        240

GGTGGCGGTA CTCATGCGGT CTACCTGCTC GACGGTCTGC GTGCCCAGGA CGACTACAAC        300

GGCTGGGACA TCAACACCCC TGCGTTCGAG TGGTTCTACG AGTCCGGCTT GTCGACGATC        360

ATGCCGGTCG GCGGACAGTC CAGCTTCTAC AGCGACTGGT ACCAGCCGTC TCGGGGCAAC        420

GGGCAGAACT ACACCTACAA GTGGGAGACG TTCCTGACCC AGGAGCTGCC GACGTGGCTG        480
```

```
GAGGCCAACC GCGGAGTGTC GCGCACCGGC AACGCGTTCG TCGGCCTGTC GATGGCGGGC    540

AGCGCGGCGC TGACCTACGC GATCCATCAC CCGCAGCAGT TCATCTACGC CTCGTCGCTG    600

TCAGGCTTCC TGAACCCGTC CGAGGGCTGG TGGCCGATGC TGATCGGGCT GGCGATGAAC    660

GACGCAGGCG GCTTCAACGC CGAGAGCATG TGGGGCCCGT CCTCGGACCC GGCGTGGAAG    720

CGCAACGACC CGATGGTCAA CATCAACCAG CTGGTGGCCA ACAACACCCG GATCTGGATC    780

TACTGCGGCA CCGGCACCCC GTCGGAGCTG GACACCGGGA CCCCGGGCCA GAACCTGATG    840

GCCGCGCAGT TCCTCGAAGG ATTCACGTTG CGGACCAACA TCGCCTTCCG TGACAACTAC    900

ATCGCAGCCG GCGGCACCAA CGGTGTCTTC AACTTCCCGG CCTCGGGCAC CCACAGCTGG    960

GGGTACTGGG GCAGCAGCT GCAGCAGATG AAGCCCGACA TCCAGCGGGT TCTGGGAGCT   1020

CAGGCCACCG CCTAGCCACC CACCCCACAC CC                                1052
```

(2) INFORMATION FOR SEQ ID NO:43:

(i) SEQUENCE CHARACTERISTICS:
        (A) LENGTH: 326 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:43:

```
Met Arg Leu Leu Asp Arg Ile Arg Gly Pro Trp Ala Arg Arg Phe Gly
 1               5                  10                  15

Val Val Ala Val Ala Thr Ala Met Met Pro Ala Leu Val Gly Leu Ala
                20                  25                  30

Gly Gly Ser Ala Thr Ala Gly Ala Phe Ser Arg Pro Gly Leu Pro Val
            35                  40                  45

Glu Tyr Leu Met Val Pro Ser Pro Ser Met Gly Arg Asp Ile Lys Ile
50                  55                  60

Gln Phe Gln Ser Gly Gly Glu Asn Ser Pro Ala Leu Tyr Leu Leu Asp
65                  70                  75                  80

Gly Leu Arg Ala Gln Glu Asp Phe Asn Gly Trp Asp Ile Asn Thr Gln
                85                  90                  95

Ala Phe Glu Trp Phe Leu Asp Ser Gly Ile Ser Val Val Met Pro Val
            100                 105                 110

Gly Gly Gln Ser Ser Phe Tyr Thr Asp Trp Tyr Ala Pro Ala Arg Asn
        115                 120                 125

Lys Gly Pro Thr Val Thr Tyr Lys Trp Glu Thr Phe Leu Thr Gln Glu
130                 135                 140

Leu Pro Gly Trp Leu Gln Ala Asn Arg Ala Val Lys Pro Thr Gly Ser
145                 150                 155                 160

Gly Pro Val Gly Leu Ser Met Ala Gly Ser Ala Ala Leu Asn Leu Ala
                165                 170                 175

Thr Trp His Pro Glu Gln Phe Ile Tyr Ala Gly Ser Met Ser Gly Phe
            180                 185                 190

Leu Asn Pro Ser Glu Gly Trp Trp Pro Phe Leu Ile Asn Ile Ser Met
        195                 200                 205

Gly Asp Ala Gly Gly Phe Lys Ala Asp Asp Met Trp Gly Lys Thr Glu
    210                 215                 220

Gly Ile Pro Thr Ala Val Gly Gln Arg Asn Asp Pro Met Leu Asn Ile
225                 230                 235                 240

Pro Thr Leu Val Ala Asn Asn Thr Arg Ile Trp Val Tyr Cys Gly Asn
                245                 250                 255
```

```
Gly Gln Pro Thr Glu Leu Gly Gly Asp Leu Pro Ala Thr Phe Leu
        260                 265                 270

Glu Gly Leu Thr Ile Arg Thr Asn Glu Thr Phe Arg Asp Asn Tyr Ile
        275                 280                 285

Ala Ala Gly Gly His Asn Gly Val Phe Asn Phe Pro Ala Asn Gly Thr
        290                 295                 300

His Asn Trp Ala Tyr Trp Gly Arg Glu Leu Gln Ala Met Lys Pro Asp
305                 310                 315                 320

Leu Gln Ala His Leu Leu
                325

(2) INFORMATION FOR SEQ ID NO:44:

(i) SEQUENCE CHARACTERISTICS:
        (A) LENGTH: 161 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:44:

Ser Gly Trp Asp Ile Asn Thr Ala Ala Phe Glu Trp Tyr Val Asp Ser
1               5                   10                  15

Gly Leu Ala Val Ile Met Pro Val Gly Gly Gln Ser Ser Phe Tyr Ser
            20                  25                  30

Asp Trp Tyr Ser Pro Ala Cys Gly Lys Ala Gly Cys Gln Thr Tyr Lys
        35                  40                  45

Trp Glu Thr Phe Leu Thr Gln Glu Leu Pro Ala Tyr Leu Ala Ala Asn
    50                  55                  60

Lys Gly Val Asp Pro Asn Arg Asn Ala Ala Val Gly Leu Ser Met Ala
65                  70                  75                  80

Gly Ser Ala Ala Leu Thr Leu Ala Ile Tyr His Pro Gln Gln Phe Gln
                85                  90                  95

Tyr Ala Gly Ser Leu Ser Gly Tyr Leu Asn Pro Ser Glu Gly Trp Trp
            100                 105                 110

Pro Met Leu Ile Asn Ile Ser Met Gly Asp Ala Gly Gly Tyr Lys Ala
        115                 120                 125

Asn Asp Met Trp Gly Pro Pro Lys Asp Pro Ser Ser Ala Trp Lys Arg
    130                 135                 140

Asn Asp Pro Met Val Asn Ile Gly Lys Leu Val Ala Asn Asn Thr Pro
145                 150                 155                 160

Leu (2) INFORMATION FOR SEQ ID NO:45:

(i) SEQUENCE CHARACTERISTICS:
        (A) LENGTH: 334 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:45:

Met Lys Phe Thr Glu Lys Trp Arg Gly Ser Ala Lys Ala Ala Met His
1               5                   10                  15

Arg Val Gly Val Ala Asp Met Ala Ala Val Ala Leu Pro Gly Leu Ile
            20                  25                  30
```

-continued

```
Gly Phe Ala Gly Gly Ser Ala Thr Ala Gly Ala Phe Ser Arg Pro Gly
         35                  40                  45

Leu Pro Val Glu Tyr Leu Asp Val Phe Ser Pro Ser Met Gly Arg Asp
 50                  55                  60

Ile Arg Val Gln Phe Gln Gly Gly Thr His Ala Val Tyr Leu Leu
 65                  70                  75                  80

Asp Gly Leu Arg Ala Gln Asp Tyr Asn Gly Trp Asp Ile Asn Thr
                 85                  90                  95

Pro Ala Phe Glu Trp Phe Tyr Glu Ser Gly Leu Ser Thr Ile Met Pro
                100                 105                 110

Val Gly Gly Gln Ser Ser Phe Tyr Ser Asp Trp Tyr Gln Pro Ser Arg
                115                 120                 125

Gly Asn Gly Gln Asn Tyr Thr Tyr Lys Trp Glu Thr Phe Leu Thr Gln
130                 135                 140

Glu Leu Pro Thr Trp Leu Glu Ala Asn Arg Gly Val Ser Arg Thr Gly
145                 150                 155                 160

Asn Ala Phe Val Gly Leu Ser Met Ala Gly Ser Ala Ala Leu Thr Tyr
                165                 170                 175

Ala Ile His His Pro Gln Gln Phe Ile Tyr Ala Ser Ser Leu Ser Gly
                180                 185                 190

Phe Leu Asn Pro Ser Glu Gly Trp Trp Pro Met Leu Ile Gly Leu Ala
                195                 200                 205

Met Asn Asp Ala Gly Gly Phe Asn Ala Glu Ser Met Trp Gly Pro Ser
210                 215                 220

Ser Asp Pro Ala Trp Lys Arg Asn Asp Pro Met Val Asn Ile Asn Gln
225                 230                 235                 240

Leu Val Ala Asn Asn Thr Arg Ile Trp Ile Tyr Cys Gly Thr Gly Thr
                245                 250                 255

Pro Ser Glu Leu Asp Thr Gly Thr Pro Gly Gln Asn Leu Met Ala Ala
                260                 265                 270

Gln Phe Leu Glu Gly Phe Thr Leu Arg Thr Asn Ile Ala Phe Arg Asp
                275                 280                 285

Asn Tyr Ile Ala Ala Gly Gly Thr Asn Gly Val Phe Asn Phe Pro Ala
                290                 295                 300

Ser Gly Thr His Ser Trp Gly Tyr Trp Gly Gln Gln Leu Gln Gln Met
305                 310                 315                 320

Lys Pro Asp Ile Gln Arg Val Leu Gly Ala Gln Ala Thr Ala
                325                 330
```

(2) INFORMATION FOR SEQ ID NO:46:

(i) SEQUENCE CHARACTERISTICS:
        (A) LENGTH: 795 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:46:

```
CTGCCGCGGG TTTGCCATCT CTTGGGTCCT GGGTCGGGAG GCCATGTTCT GGGTAACGAT     60

CCGGTACCGT CCGGCGATGT GACCAACATG CGAACAGCGA CAACGAAGCT AGGAGCGGCG    120

CTCGGCGCAG CAGCATTGGT GGCCGCCACG GGGATGGTCA GCGCGGCGAC GGCGAACGCC    180

CAGGAAGGGC ACCAGGTCCG TTACACGCTC ACCTCGGCCG GCGCTTACGA GTTCGACCTG    240

TTCTATCTGA CGACGCAGCC GCCGAGCATG CAGGCGTTCA ACGCCGACGC GTATGCGTTC    300
```

| | |
|---|---|
| GCCAAGCGGG AGAAGGTCAG CCTCGCCCCG GGTGTGCCGT GGGTCTTCGA ACCACGATG | 360 |
| GCCGACCCGA ACTGGGCGAT CCTTCAGGTC AGCAGCACCA CCCGCGGTGG GCAGGCCGCC | 420 |
| CCGAACGCGC ACTGCGACAT CGCCGTCGAT GGCCAGGAGG TGCTCAGCCA GCACGACGAC | 480 |
| CCCTACAACG TGCGGTGCCA GCTCGGTCAG TGGTGAGTCA CCTCGCCGAG AGTCCGGCCA | 540 |
| GCGCCGGCGG CAGCGGCTCG CGGTGCAGCA CCCCGAGGCG CTGGGTCGCG CGGGTCAGCG | 600 |
| CGACGTAAAG ATCGCTGGCC CCGCGCGGCC CCTCGGCGAG GATCTGCTCC GGGTAGACCA | 660 |
| CCAGCACGGC GTCTAACTCC AGACCCTTGG TCTGCGTGGG TGCCACCGCG CCCGGGACAC | 720 |
| CGGGCGGGCC GATCACCACG CTGGTGCCCT CCCGGTCCGC CTCCGCACGC ACGAAATCGT | 780 |
| CGATGGCACC GGCGA | 795 |

(2) INFORMATION FOR SEQ ID NO:47:

(i) SEQUENCE CHARACTERISTICS:
        (A) LENGTH: 142 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

```
Met Arg Thr Ala Thr Thr Lys Leu Gly Ala Ala Leu Gly Ala Ala Ala
 1               5                  10                  15
Leu Val Ala Ala Thr Gly Met Val Ser Ala Ala Thr Ala Asn Ala Gln
             20                  25                  30
Glu Gly His Gln Val Arg Tyr Thr Leu Thr Ser Ala Gly Ala Tyr Glu
         35                  40                  45
Phe Asp Leu Phe Tyr Leu Thr Thr Gln Pro Pro Ser Met Gln Ala Phe
     50                  55                  60
Asn Ala Asp Ala Tyr Ala Phe Ala Lys Arg Glu Lys Val Ser Leu Ala
 65                  70                  75                  80
Pro Gly Val Pro Trp Val Phe Glu Thr Thr Met Ala Asp Pro Asn Trp
                 85                  90                  95
Ala Ile Leu Gln Val Ser Ser Thr Thr Arg Gly Gly Gln Ala Ala Pro
                100                 105                 110
Asn Ala His Cys Asp Ile Ala Val Asp Gly Gln Glu Val Leu Ser Gln
            115                 120                 125
His Asp Asp Pro Tyr Asn Val Arg Cys Gln Leu Gly Gln Trp
        130                 135                 140
```

(2) INFORMATION FOR SEQ ID NO:48:

(i) SEQUENCE CHARACTERISTICS:
        (A) LENGTH: 300 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:48:

| | |
|---|---|
| GCCAGTGCGC CAACGGTTTT CATCGATGCC GCACACAACC CCGGTGGGCC CTGCGCTTGC | 60 |
| CGAAGGCTGC GCGACGAGTT CGACTTCCGG TATCTCGTCG GCGTCGTCTC GGTGATGGGG | 120 |
| GACAAGGACG TGGACGGGAT CCGCCAGGAC CCGGGCGTGC GGACGGGCG CGGTCTCGCA | 180 |
| CTGTTCGTCT CGGGCGACAA CCTTCGAAAG GGTGCGGCGC TCAACACGAT CCAGATCGCC | 240 |
| GAGCTGCTGG CCGCCCAGTT GTAAGTGTTC CGCCGAAATT GCATTCCACG CCGATAATCG | 300 |

(2) INFORMATION FOR SEQ ID NO:49:

(i) SEQUENCE CHARACTERISTICS:
        (A) LENGTH: 563 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:49:

```
GGATCCTCGG CCGGCTCAAG AGTCCGCGCC GAGGTGGATG TGACGCTGGA CGGCTACGAG    60
TTCAGTCGGG CCTGCGAGGC GCTGTACCAC TTCGCCTGGG ACGAGTTCTG CGACTGGTAT   120
GTCGAGCTTG CCAAAGTGCA ACTGGGTGAA GGTTTCTCGC ACACCACGGC CGTGTTGGCC   180
ACCGTGCTCG ATGTGCTGCT CAAGCTTCTG CACCCGGTCA TGCCGTTCGT CACCGAGGTG   240
CTGTGGAAGG CCCTGACCGG GCGGGCCGGC GCGAGCGAAC GTCTGGGAAA TGTGGAGTCA   300
CTGGTCGTCG CGGACTGGCC CACGCCCACC GGATACGCGC TGGATCAGGC TGCCGCACAA   360
CGGATCGCCG ACACCCAGAA GTTGATCACC GAGGTGCGCC GGTTCCGCAG CGATCAGGGT   420
CTGGCCGACC GCCAGCGGGT GCCTGCCCGG TTGTCCGGCA TCGACACCGC GGGTCTGGAC   480
GCCCATGTCC CGGCGGTGCG CGCGCTGGCC TGGCTTGACC GAGGGTGATG AGGGCTTCAC   540
CGCGTCCGAA TCGGTCGAGG TGC                                          563
```

(2) INFORMATION FOR SEQ ID NO:50:

(i) SEQUENCE CHARACTERISTICS:
        (A) LENGTH: 434 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:50:

```
GGGCCGGGCC CGAGGATGAG CAAGTTCGAA GTCGTCACCG GGATGGCGTT CGCGGCTTTC    60
GCCGACGCGC CCATCGACGT CGCCGTCGTC GAGGTCGGGC TCGGTGGTCG CTGGGACGCG   120
ACGAACGTGG TGAACGCACC GGTCGCGGTC ATCACCCCGA TCGGGGTGGA CCACACCGAC   180
TACCTCGGTG ACACGATCGC CGAGATCGCC GGGGAGAAGG CCGGAAATCA TCACCCGCCA   240
GCCGACGACC TGGTGCCGAC CGACACCGTC GCCGTGCTGG CGCGGCAGGT TCCCGAGGCC   300
ATGGAGGTGC TGCTGGCCCA GGCGGTGCGC TCGGATGCGG CTGTAGCGCG CGAGGATTCG   360
GAGTGCGCGG TGCTGGGCCG TCAGGTCGCC ATCGGCGGCA GCTGCTCCGG TTGCAGGGGC   420
TCGGTGGCGT CTAC                                                    434
```

(2) INFORMATION FOR SEQ ID NO:51:

(i) SEQUENCE CHARACTERISTICS:
        (A) LENGTH: 438 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:51:

```
GGATCCCACT CCCGCGCCGG CGGCGGCCAG CTGGTACGGC CATTCCAGCG TGCTGATCGA    60
GGTCGACGGC TACCGCGTGC TGGCCGACCC GGTGTGGAGC AACAGATGTT CGCCCTCACG   120
```

```
GGCGGTCGGA CCGCAGCGCA TGCACGACGT CCCGGTGCCG CTGGAGGCGC TTCCCGCCGT      180

GGACGCGGTG GTGATCGCCA ACGACCACTA CGACCACCTC GACATCGACA CCATCGTCGC      240

GTTGGCGCAC ACCCAGCGGG CCCCGTTCGT GGTGCCGTTG GGCATCGGCG CACACCTGCG      300

CAAGTGGGGC GTCCCCGAGG CGCGGATCGT CGAGTTGGAC TGGCACGAAG CCCACCGCAT      360

CGACGACCTG ACGCTGGTCT GCACCCCCGC CCGGCACTTC TCCGGCCGGT TGTTCTCCCG      420

CGACTCGACG CTGTGGGC                                                   438

(2) INFORMATION FOR SEQ ID NO:52:

(i) SEQUENCE CHARACTERISTICS:
        (A) LENGTH: 87 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:52:

Ala Ser Ala Pro Thr Val Phe Ile Asp Ala Ala His Asn Pro Gly Gly
1               5                  10                 15

Pro Cys Ala Cys Arg Arg Leu Arg Asp Glu Phe Asp Phe Arg Tyr Leu
            20                  25                  30

Val Gly Val Val Ser Val Met Gly Asp Lys Asp Val Asp Gly Ile Arg
        35                  40                  45

Gln Asp Pro Gly Val Pro Asp Gly Arg Gly Leu Ala Leu Phe Val Ser
50                  55                  60

Gly Asp Asn Leu Arg Lys Gly Ala Ala Leu Asn Thr Ile Gln Ile Ala
65                  70                  75                  80

Glu Leu Leu Ala Ala Gln Leu
            85

(2) INFORMATION FOR SEQ ID NO:53:

(i) SEQUENCE CHARACTERISTICS:
        (A) LENGTH: 175 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:53:

Gly Ser Ser Ala Gly Ser Arg Val Arg Ala Glu Val Asp Val Thr Leu
1               5                  10                 15

Asp Gly Tyr Glu Phe Ser Arg Ala Cys Glu Ala Leu Tyr His Phe Ala
            20                  25                  30

Trp Asp Glu Phe Cys Asp Trp Tyr Val Glu Leu Ala Lys Val Gln Leu
        35                  40                  45

Gly Glu Gly Phe Ser His Thr Thr Ala Val Leu Ala Thr Val Leu Asp
50                  55                  60

Val Leu Leu Lys Leu Leu His Pro Val Met Pro Phe Val Thr Glu Val
65                  70                  75                  80

Leu Trp Lys Ala Leu Thr Gly Arg Ala Gly Ala Ser Glu Arg Leu Gly
            85                  90                  95

Asn Val Glu Ser Leu Val Val Ala Asp Trp Pro Thr Pro Thr Gly Tyr
            100                 105                 110

Ala Leu Asp Gln Ala Ala Ala Gln Arg Ile Ala Asp Thr Gln Lys Leu
            115                 120                 125
```

```
Ile Thr Glu Val Arg Arg Phe Arg Ser Asp Gln Gly Leu Ala Asp Arg
    130                 135                 140

Gln Arg Val Pro Ala Arg Leu Ser Gly Ile Asp Thr Ala Gly Leu Asp
145                 150                 155                 160

Ala His Val Pro Ala Val Arg Ala Leu Ala Trp Leu Asp Arg Gly
                165                 170                 175

(2) INFORMATION FOR SEQ ID NO:54:

(i) SEQUENCE CHARACTERISTICS:
        (A) LENGTH: 144 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:54:

Gly Pro Gly Pro Arg Asn Ser Lys Phe Glu Val Val Thr Gly Met Ala
1               5                   10                  15

Phe Ala Ala Phe Ala Asp Ala Pro Ile Asp Val Ala Val Val Glu Val
                20                  25                  30

Gly Leu Gly Gly Arg Trp Asp Ala Thr Asn Val Val Asn Ala Pro Val
            35                  40                  45

Ala Val Ile Thr Pro Ile Gly Val Asp His Thr Asp Tyr Leu Gly Asp
        50                  55                  60

Thr Ile Ala Glu Ile Ala Gly Glu Lys Ala Gly Asn His His Pro Pro
65                  70                  75                  80

Ala Asp Asp Leu Val Pro Thr Asp Thr Val Ala Val Leu Ala Arg Gln
                85                  90                  95

Val Pro Glu Ala Asn Glu Val Leu Leu Ala Gln Ala Val Arg Ser Asp
                100                 105                 110

Ala Ala Val Ala Arg Glu Asp Ser Glu Cys Ala Val Leu Gly Arg Gln
            115                 120                 125

Val Ala Ile Gly Gly Ser Cys Ser Gly Cys Arg Gly Ser Val Ala Ser
        130                 135                 140

(2) INFORMATION FOR SEQ ID NO:55:

(i) SEQUENCE CHARACTERISTICS:
        (A) LENGTH: 145 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:55:

Asp Pro Thr Pro Ala Pro Ala Ala Ala Ser Trp Tyr Gly His Ser Ser
1               5                   10                  15

Val Leu Ile Glu Val Asp Gly Tyr Arg Val Leu Ala Asp Pro Val Trp
                20                  25                  30

Ser Asn Arg Cys Ser Pro Ser Arg Ala Val Gly Pro Gln Arg Met His
            35                  40                  45

Asp Val Pro Val Pro Leu Glu Ala Leu Pro Ala Val Asp Ala Val Val
        50                  55                  60

Ile Ser Asn Asp His Tyr Asp His Leu Asp Ile Asp Thr Ile Val Ala
65                  70                  75                  80

Leu Ala His Thr Gln Arg Ala Pro Phe Val Val Pro Leu Gly Ile Gly
                85                  90                  95
```

```
Ala His Leu Arg Lys Trp Gly Val Pro Glu Ala Arg Ile Val Glu Leu
            100                 105                 110
Asp Trp His Glu Ala His Arg Ile Asp Asp Leu Thr Leu Val Cys Thr
            115                 120                 125
Pro Ala Arg His Phe Ser Gly Arg Leu Phe Ser Arg Asp Ser Thr Leu
    130                 135                 140
Trp
145

(2) INFORMATION FOR SEQ ID NO:56:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
        (D) OTHER INFORMATION: Residue can be either Gly, Ile, Leu or
            Val (A) NAME/KEY: Other
        (B) LOCATION: 2...2
        (D) OTHER INFORMATION: Residue can be either Ile, Leu, Gly or
            Ala (xi) SEQUENCE DESCRIPTION: SEQ ID NO:56:

Xaa Xaa Ala Pro Xaa Gly Asp Ala Xaa Arg
1               5                   10

(2) INFORMATION FOR SEQ ID NO:57:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 7...7
        (D) OTHER INFORMATION: Residue can be either Ile or Leu (xi) SEQUENCE DESCRIPTION: SEQ ID NO:57:

Pro Glu Ala Glu Ala Asn Xaa Arg
1               5

(2) INFORMATION FOR SEQ ID NO:58:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 4...4
        (D) OTHER INFORMATION: Residue can be either Gln or Gly (A) NAME/KEY: Other
        (B) LOCATION: 5...5
        (D) OTHER INFORMATION: Residue cn be either Gly or Gln
```

(xi) SEQUENCE DESCRIPTION: SEQ ID NO:58:

Thr Ala Asn Xaa Xaa Glu Tyr Tyr Asp Asn Arg
1               5                   10

(2) INFORMATION FOR SEQ ID NO:59:

(i) SEQUENCE CHARACTERISTICS:
            (A) LENGTH: 34 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:59:

Asn Ser Pro Arg Ala Glu Ala Glu Ala Asn Leu Arg Gly Tyr Phe Thr
1               5                   10                  15

Ala Asn Pro Ala Glu Tyr Tyr Asp Leu Arg Gly Ile Leu Ala Pro Ile
                20                  25                  30

Gly Asp (2) INFORMATION FOR SEQ ID NO:60:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:60:

CCGGTGGGCC CGGGCTGCGC                                                   20

(2) INFORMATION FOR SEQ ID NO:61:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:61:

TGGCCGGCCA CCACGTGGTA                                                   20

(2) INFORMATION FOR SEQ ID NO:62:

(i) SEQUENCE CHARACTERISTICS:
            (A) LENGTH: 313 base pairs
            (B) TYPE: nucleic acid
            (C) STRANDEDNESS: single
            (D) TOPOLOGY: linear (ii) MOLECULE TYPE: Genomic DNA (xi) SEQUENCE DESCRIPTION: SEQ ID NO:62:

GCCGGTGGGC CCGGGCTGCG CGGAATACGC GGCAGCCAAT CCCACTGGGC CGGCCTCGGT        60

GCAGGGAATG TCGCAGGACC CGGTCGCGGT GGCGGCCTCG AACAATCCGG AGTTGACAAC       120

GCTGTACGGC TGCACTGTCG GGCCAGCTCA ATCCGCAAGT AAACCTGGTG GACACCCTCA       180

ACAGCGGTCA GTACACGGTG TTCGCACCGA CCAACGCGGC ATTTAGCAAG CTGCCGGCAT       240

CCACGATCGA CGAGCTCAAG ACCAATTCGT CACTGCTGAC CAGCATCCTG ACCTACCACG       300

TGGTGGCCGG CCA                                                         313

(2) INFORMATION FOR SEQ ID NO:63:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:63:

```
Glu Pro Ala Gly Pro Leu Pro Xaa Tyr Asn Glu Arg Leu His Thr Leu
 1               5                  10                  15

Xaa Gln
```

(2) INFORMATION FOR SEQ ID NO:64:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:64:

```
Gly Leu Asp Asn Glu Leu Ser Leu Val Asp Gly Gln Gly Arg Thr Leu
 1               5                  10                  15

Thr Val Gln Gln Xaa Asp Thr Phe Leu
                20                  25
```

(2) INFORMATION FOR SEQ ID NO:65:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:65:

```
Asp Pro Xaa Pro Asp Ile Glu Val Glu Phe Ala Arg Gly Thr Gly Ala
 1               5                  10                  15

Glu Pro Gly Leu Xaa Xaa Val Xaa Asp Ala
                20                  25
```

(2) INFORMATION FOR SEQ ID NO:66:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:66:

ACCGCCCTCG AGTTCTCCCG GCCAGGTCTG CC                                32

(2) INFORMATION FOR SEQ ID NO:67:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:67:

AAGCACGAGC TCAGTCTCTT CCACGCGGAC GT 32

(2) INFORMATION FOR SEQ ID NO:68:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:68:

CATGGATCCA TTCTCCCGGC CCGGTCTTCC 30

(2) INFORMATION FOR SEQ ID NO:69:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:69:

TTTGAATTCT AGGCGGTGGC CTGAGC 26

(2) INFORMATION FOR SEQ ID NO:70:

(i) SEQUENCE CHARACTERISTICS:
        (A) LENGTH: 161 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:70:

```
Ser Gly Trp Asp Ile Asn Thr Ala Ala Phe Glu Trp Tyr Val Asp Ser
 1               5                  10                  15

Gly Leu Ala Val Ile Met Pro Val Gly Gly Gln Ser Ser Phe Tyr Ser
             20                  25                  30

Asp Trp Tyr Ser Pro Ala Cys Gly Lys Ala Gly Cys Gln Thr Tyr Lys
         35                  40                  45

Trp Glu Thr Phe Leu Thr Gln Glu Leu Pro Ala Tyr Leu Ala Ala Asn
     50                  55                  60

Lys Gly Val Asp Pro Asn Arg Asn Ala Val Gly Leu Ser Met Ala
 65                  70                  75                  80

Gly Ser Ala Ala Leu Thr Leu Ala Ile Tyr His Pro Gln Gln Phe Gln
                 85                  90                  95

Tyr Ala Gly Ser Leu Ser Gly Tyr Leu Asn Pro Ser Glu Gly Trp Trp
            100                 105                 110

Pro Met Leu Ile Asn Ile Ser Met Gly Asp Ala Gly Gly Tyr Lys Ala
        115                 120                 125

Asn Asp Met Trp Gly Arg Thr Glu Asp Pro Ser Ser Ala Trp Lys Arg
    130                 135                 140

Asn Asp Pro Met Val Asn Ile Gly Lys Leu Val Ala Asn Asn Thr Pro
145                 150                 155                 160
```

Leu (2) INFORMATION FOR SEQ ID NO:71:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:71:

```
GAGAGACTCG AGAACGCCCA GGAAGGGCAC CAG                              33
```

(2) INFORMATION FOR SEQ ID NO:72:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:72:

```
GAGAGACTCG AGTGACTCAC CACTGACCGA GC                               32
```

(2) INFORMATION FOR SEQ ID NO:73:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:73:

```
GGNGCNGCNC ARGCNGARCC                                             20
```

(2) INFORMATION FOR SEQ ID NO:74:

(i) SEQUENCE CHARACTERISTICS:
        (A) LENGTH: 825 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:74:

```
TTGGATCCCA CTCCCGCGCC GGCGGCGGCC AGCTGGTACG GCCATTCCAG CGTGCTGATC    60

GAGGTCGACG GCTACCGCGT GCTGGCCGAC CCGGTGTGGA GCAACAGATG TTCGCCCTCA   120

CGGGCGGTCG GACCGCAGCG CATGCACGAC GTCCCGGTGC CGCTGGAGGC GCTTCCCGCC   180

GTGGACGCGG TGGTGATCAG CCACGACCAC TACGACCACC TCGACATCGA CACCATCGTC   240

GCGTTGGCGC ACACCCAGCG GGCCCCGTTC GTGGTGCCGT TGGGCATCGG CGCACACCTG   300

CGCAAGTGGG GCGTCCCCGA GGCGCGGATC GTCGAGTTGG ACTGGCACGA AGCCCACCGC   360

ATAGACGACC TGACGCTGGT CTGCACCCCC GCCCGGCACT TCTCCGGACG GTTGTTCTCC   420

CGCGACTCGA CGCTGTGGGC GTCGTGGGTG GTCACCGGCT CGTCGCACAA GGCGTTCTTC   480

GGTGGCGACA CCGGATACAC GAAGAGCTTC GCCGAGATCG GCGACGAGTA CGGTCCGTTC   540

GATCTGACCC TGCTGCCGAT CGGGGCCTAC CATCCCGCGT TCGCCGACAT CCACATGAAC   600
```

```
CCCGAGGAGG CGGTGCGCGC CCATCTGGAC CTGACCGAGG TGGACAACAG CCTGATGGTG      660

CCCATCCACT GGGCGACATT CCGCCTCGCC CCGCATCCGT GGTCCGAGCC CGCCGAACGC      720

CTGCTGACCG CTGCCGACGC CGAGCGGGTA CGCCTGACCG TGCCGATTCC CGGTCAGCGG      780

GTGGACCCGG AGTCGACGTT CGACCCGTGG TGGCGGTTCT GAACC                      825
```

(2) INFORMATION FOR SEQ ID NO:75:

(i) SEQUENCE CHARACTERISTICS:
        (A) LENGTH: 273 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:75:

```
Leu Asp Pro Thr Pro Ala Pro Ala Ala Ala Ser Trp Tyr Gly His Ser
 1               5                  10                  15

Ser Val Leu Ile Glu Val Asp Gly Tyr Arg Val Leu Ala Asp Pro Val
             20                  25                  30

Trp Ser Asn Arg Cys Ser Pro Ser Arg Ala Val Gly Pro Gln Arg Met
         35                  40                  45

His Asp Val Pro Val Pro Leu Glu Ala Leu Pro Ala Val Asp Ala Val
     50                  55                  60

Val Ile Ser His Asp His Tyr Asp His Leu Asp Ile Asp Thr Ile Val
65                  70                  75                  80

Ala Leu Ala His Thr Gln Arg Ala Pro Phe Val Val Pro Leu Gly Ile
                 85                  90                  95

Gly Ala His Leu Arg Lys Trp Gly Val Pro Glu Ala Arg Ile Val Glu
             100                 105                 110

Leu Asp Trp His Glu Ala His Arg Ile Asp Asp Leu Thr Leu Val Cys
         115                 120                 125

Thr Pro Ala Arg His Phe Ser Gly Arg Leu Phe Ser Arg Asp Ser Thr
     130                 135                 140

Leu Trp Ala Ser Trp Val Val Thr Gly Ser Ser His Lys Ala Phe Phe
145                 150                 155                 160

Gly Gly Asp Thr Gly Tyr Thr Lys Ser Phe Ala Glu Ile Gly Asp Glu
                 165                 170                 175

Tyr Gly Pro Phe Asp Leu Thr Leu Pro Ile Gly Ala Tyr His Pro
             180                 185                 190

Ala Phe Ala Asp Ile His Met Asn Pro Glu Glu Ala Val Arg Ala His
         195                 200                 205

Leu Asp Leu Thr Glu Val Asp Asn Ser Leu Met Val Pro Ile His Trp
     210                 215                 220

Ala Thr Phe Arg Leu Ala Pro His Pro Trp Ser Glu Pro Ala Glu Arg
225                 230                 235                 240

Leu Leu Thr Ala Ala Asp Ala Glu Arg Val Arg Leu Thr Val Pro Ile
                 245                 250                 255

Pro Gly Gln Arg Val Asp Pro Glu Ser Thr Phe Asp Pro Trp Trp Arg
             260                 265                 270

Phe
```

(2) INFORMATION FOR SEQ ID NO:76:

(i) SEQUENCE CHARACTERISTICS:
        (A) LENGTH: 10 amino acids
        (B) TYPE: amino acid (C) STRANDEDNESS: single
        (D) TOPOLOGY: linear (ii) MOLECULE TYPE: protein (xi) SEQUENCE DESCRIPTION: SEQ ID NO:76:

Ala Lys Thr Ile Ala Tyr Asp Glu Glu Ala
 1               5                  10

(2) INFORMATION FOR SEQ ID NO:77:

(i) SEQUENCE CHARACTERISTICS:
        (A) LENGTH: 337 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:77:

GATCCCTACA TCCTGCTGGT CAGCTCCAAG GTGTCGACCG TCAAGGATCT GCTCCCGCTG        60

CTGGAGAAGG TCATCCAGGC CGGCAAGCCG CTGCTGATCA TCGCCGAGGA CGTCGAGGGC       120

GAGGCCCTGT CCACGCTGGT GGTCAACAAG ATCCGCGGCA CCTTCAAGTC CGTCGCCGTC       180

AAGGCTCCGG GCTTCGGTGA CCGCCGCAAG GCGATGCTGC AGGACATGGC CATCCTCACC       240

GGTGGTCAGG TCGTCAGCGA AGAGTCGGG CTGTCCCTGG AGACCGCCGA CGTCTCGCTG        300

CTGGGCCAGG CCCGCAAGGT CGTCGTCACC AAGGACA                                337

(2) INFORMATION FOR SEQ ID NO:78:

(i) SEQUENCE CHARACTERISTICS:
        (A) LENGTH: 112 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:78:

Asp Pro Tyr Ile Leu Leu Val Ser Ser Lys Val Ser Thr Val Lys Asp
 1               5                  10                  15

Leu Leu Pro Leu Leu Glu Lys Val Ile Gln Ala Gly Lys Pro Leu Leu
                20                  25                  30

Ile Ile Ala Glu Asp Val Glu Gly Glu Ala Leu Ser Thr Leu Val Val
            35                  40                  45

Asn Lys Ile Arg Gly Thr Phe Lys Ser Val Ala Val Lys Ala Pro Gly
 50                  55                  60

Phe Gly Asp Arg Arg Lys Ala Met Leu Gln Asp Met Ala Ile Leu Thr
 65                  70                  75                  80

Gly Gly Gln Val Val Ser Glu Arg Val Gly Leu Ser Leu Glu Thr Ala
                85                  90                  95

Asp Val Ser Leu Leu Gly Gln Ala Arg Lys Val Val Val Thr Lys Asp
                100                 105                 110

(2) INFORMATION FOR SEQ ID NO:79:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:79:

```
CCGTACGAGA AGATCGGCGC TGAGCTGGTC AAAGAGGTCG CCAAGAAGAC CGACGACGTC      60

GCGGGCGACG GCACCACCAC CGCCACCGTG CTCGCTCAGG CTCTGGTTCG CGAAGGCCTG     120

CGCAACGTCG CAGCCGGCGC CAACCCGCTC GGCCTCAAGC GTGGCATCGA GAAGGCTGTC     180

GAGGCTGTCA CCCAGTCGCT GCTGAAGTCG GCCAAGGAGG TCGAGACCAA GGAGCAGATT     240

TCTGCCACCG CGGCGATCTC CGCCGGCGAC ACCCAGATCG GCGAGCTCAT CGCCGAGGCC     300

ATGGACAAGG TCGGCAACGA GGGTGTCATC ACCGTCGAGG AGTCGAACAC CTTCGGCCTG     360
```

(2) INFORMATION FOR SEQ ID NO:80:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:80:

```
Pro Tyr Glu Lys Ile Gly Ala Glu Leu Val Lys Glu Val Ala Lys Lys
 1               5                  10                  15

Thr Asp Val Ala Gly Asp Gly Thr Thr Thr Ala Thr Val Leu Ala
            20                  25                  30

Gln Ala Leu Val Arg Glu Gly Leu Arg Asn Val Ala Ala Gly Ala Asn
         35                  40                  45

Pro Leu Gly Leu Lys Arg Gly Ile Glu Lys Ala Val Glu Ala Val Thr
 50                  55                  60

Gln Ser Leu Leu Lys Ser Ala Lys Glu Val Glu Thr Lys Glu Gln Ile
65                  70                  75                  80

Ser Ala Thr Ala Ala Ile Ser Ala Gly Asp Thr Gln Ile Gly Glu Leu
                85                  90                  95

Ile Ala Glu Ala Met Asp Lys Val Gly Asn Glu Gly Val Ile Thr Val
            100                 105                 110

Glu Glu Ser Asn Thr Phe Gly Leu
        115                 120
```

(2) INFORMATION FOR SEQ ID NO:81:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:81:

```
ACTGACGCTG AGGAGCGAAA GCGTGGGGAG CGAACAGGAT TAG                        43
```

(2) INFORMATION FOR SEQ ID NO:82:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:82:

```
CGACAAGGAA CTTCGCTACC TTAGGACCGT CATAGTTACG GGC                        43
```

(2) INFORMATION FOR SEQ ID NO:83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:83:

```
AAAAAAAAAA AAAAAAAAAA                                                20
```

(2) INFORMATION FOR SEQ ID NO:84:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:84:

```
GGAAGGAAGC GGCCGCTTTT TTTTTTTTTT T                                   31
```

(2) INFORMATION FOR SEQ ID NO:85:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:85:

```
GAGAGAGAGC CCGGGCATGC TSCTSCTSCT S                                   31
```

(2) INFORMATION FOR SEQ ID NO:86:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:86:

```
CTCGATGAAC CGCTCGGAGC GCTCGACCTG AAGCTGCGCC ACGTCATGCA GTTCGAGCTC      60

AAGCGCATCC AGCGGGAGGT CGGGATCACG TTCATCTACG TGACCCACGA CCAGGAAGAG     120

GCGCTCACGA TGAGTGACCG CATCGCGGTG ATGAACGCCG GCAACGTCGA ACAGATCGGC     180

AGCCCGACCG AGATCTACGA CCGTCCCGCG ACGGTGTTCG TCGCCAGCTT CATCGAAT      238
```

(2) INFORMATION FOR SEQ ID NO:87:

(i) SEQUENCE CHARACTERISTICS:
        (A) LENGTH: 79 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:87:

```
Leu Asp Glu Pro Leu Gly Ala Leu Asp Leu Lys Leu Arg His Val Met
  1               5                  10                  15

Gln Phe Glu Leu Lys Arg Ile Gln Arg Glu Val Gly Ile Thr Phe Ile
                 20                  25                  30

Tyr Val Thr His Asp Gln Glu Ala Leu Thr Met Ser Asp Arg Ile
             35                  40                  45

Ala Val Met Asn Ala Gly Asn Val Glu Gln Ile Gly Ser Pro Thr Glu
 50                  55                  60

Ile Tyr Asp Arg Pro Ala Thr Val Phe Val Ala Ser Phe Ile Glu
 65              70                  75
```

(2) INFORMATION FOR SEQ ID NO:88:

(i) SEQUENCE CHARACTERISTICS:
        (A) LENGTH: 1518 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:88:

```
CACTCGCCAT GGGTGTTACA ATACCCCACC AGTTCCTCGA AGTAAACGAA CAGAACCGTG      60
ACATCCAGCT GAGAAAATAT TCACAGCGAC GAAGCCCGGC CGATGCCTGA TGGGGTCCGG     120
CATCAGTACA GCGCGCTTTC CTGCGCGGAT TCTATTGTCG AGTCCGGGGT GTGACGAAGG     180
AATCCATTGT CGAAATGTAA ATTCGTTGCG GAATCACTTG CATAGGTCCG TCAGATCCGC     240
GAAGGTTTAC CCCACAGCCA CGACGGCTGT CCCCGAGGAG GACCTGCCCT GACCGGCACA     300
CACATCACCG CTGCAGAACC TGCAGAACAG ACGGCGGATT CCGCGGCACC GCCCAAGGGC     360
GCGCCGGTGA TCGAGATCGA CCATGTCACG AAGCGCTTCG GCGACTACCT GGCCGTCGCG     420
GACGCAGACT TCTCCATCGC GCCCGGGGAG TTCTTCTCCA TGCTCGGCCC GTCCGGGTGT     480
GGGAAGACGA CCACGTTGCG CATGATCGCG GGATTCGAGA CCCCGACTGA AGGGGCGATC     540
CGCCTCGAAG GCGCCGACGT GTCGAGGACC CCACCCAACA AGCGCAACGT CAACACGGTG     600
TTCCAGCACT ACGCGCTGTT CCCGCACATG ACGGTCTGGG ACAACGTCGC GTACGGCCCG     660
CGCAGCAAGA AACTCGGCAA AGGCGAGGTC CGCAAGCGCG TCGACGAGCT GCTGGAGATC     720
GTCCGGCTGA CCGAATTTGC CGAGCGCAGG CCCGCCCAGC TGTCCGGCGG GCAGCAGCAG     780
CGGGTGGCGT TGGCCCGGGC ACTGGTGAAC TACCCCAGCG CGCTGCTGCT CGATGAACCG     840
CTCGGAGCGC TCGACCTGAA GCTGCGCCAC GTCATGCAGT TCGAGCTCAA GCGCATCCAG     900
CGGGAGGTCG GGATCACGTT CATCTACGTG ACCCACGACC AGGAAGAGGC GCTCACGATG     960
AGTGACCGCA TCGCGGTGAT GAACGCCGGC AACGTCGAAC AGATCGGCAG CCCGACCGAG    1020
ATCTACGACC GTCCCGCGAC GGTGTTCGTC GCCAGCTTCA TCGGACAGGC CAACCTCTGG    1080
GCGGGCCGGT GCACCGGCCG CTCCAACCGC GATTACGTCG AGATCGACGT TCTCGGCTCG    1140
ACGCTGAAGG CACGCCCGGG CGAGACCACG ATCGAGCCCG GCGGGCACGC CACCCTGATG    1200
GTGCGTCCGG AACGCATCCG GGTCACCCCG GGCTCCCAGG ACGCGCCGAC CGGTGACGTC    1260
GCCTGCGTGC GTGCCACCGT CACCGACCTG ACCTTCCAAG GTCCGGTGGT GCGGCTCTCG    1320
CTGGCCGCTC CGGACGACTC GACCGTGATC GCCCACGTCG GCCCCGAGCA GGATCTGCCG    1380
CTGCTGCGCC CCGGCGACGA CGTGTACGTC AGCTGGGCAC CGGAAGCCTC CCTGGTGCTT    1440
CCCGGCGACG ACATCCCCAC CACCGAGGAC CTCGAAGAGA TGCTCGACGA CTCCTGAGTC    1500
ACGCTTCCCG ATTGCCGA                                                  1518
```

(2) INFORMATION FOR SEQ ID NO:89:

(i) SEQUENCE CHARACTERISTICS:
        (A) LENGTH: 376 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:89:

```
Val Ile Glu Ile Asp His Val Thr Lys Arg Phe Gly Asp Tyr Leu Ala
  1               5                  10                  15

Val Ala Asp Ala Asp Phe Ser Ile Ala Pro Gly Glu Phe Phe Ser Met
                 20                  25                  30

Leu Gly Pro Ser Gly Cys Gly Lys Thr Thr Leu Arg Met Ile Ala
             35                  40                  45

Gly Phe Glu Thr Pro Thr Glu Gly Ala Ile Arg Leu Glu Gly Ala Asp
         50                  55                  60

Val Ser Arg Thr Pro Pro Asn Lys Arg Asn Val Asn Thr Val Phe Gln
 65                  70                  75                  80

His Tyr Ala Leu Phe Pro His Met Thr Val Trp Asn Val Ala Tyr
                 85                  90                  95

Gly Pro Arg Ser Lys Lys Leu Gly Lys Gly Val Arg Lys Arg Val
                100                 105                 110

Asp Glu Leu Leu Glu Ile Val Arg Leu Thr Glu Phe Ala Glu Arg Arg
                115                 120                 125

Pro Ala Gln Leu Ser Gly Gly Gln Gln Gln Arg Val Ala Leu Ala Arg
                130                 135                 140

Ala Leu Val Asn Tyr Pro Ser Ala Leu Leu Leu Asp Glu Pro Leu Gly
145                 150                 155                 160

Ala Leu Asp Leu Lys Leu Arg His Val Met Gln Phe Glu Leu Lys Arg
                165                 170                 175

Ile Gln Arg Glu Val Gly Ile Thr Phe Ile Tyr Val Thr His Asp Gln
                180                 185                 190

Glu Glu Ala Leu Thr Met Ser Asp Arg Ile Ala Val Met Asn Ala Gly
                195                 200                 205

Asn Val Glu Gln Ile Gly Ser Pro Thr Glu Ile Tyr Asp Arg Pro Ala
                210                 215                 220

Thr Val Phe Val Ala Ser Phe Ile Gly Gln Ala Asn Leu Trp Ala Gly
225                 230                 235                 240

Arg Cys Thr Gly Arg Ser Asn Arg Asp Tyr Val Glu Ile Asp Val Leu
                245                 250                 255

Gly Ser Thr Leu Lys Ala Arg Pro Gly Glu Thr Thr Ile Glu Pro Gly
                260                 265                 270

Gly His Ala Thr Leu Met Val Arg Pro Glu Arg Ile Arg Val Thr Pro
                275                 280                 285

Gly Ser Gln Asp Ala Pro Thr Gly Asp Val Ala Cys Val Arg Ala Thr
                290                 295                 300

Val Thr Asp Leu Thr Phe Gln Gly Pro Val Val Arg Leu Ser Leu Ala
305                 310                 315                 320

Ala Pro Asp Asp Ser Thr Val Ile Ala His Val Gly Pro Glu Gln Asp
                325                 330                 335

Leu Pro Leu Leu Arg Pro Gly Asp Asp Val Tyr Val Ser Trp Ala Pro
                340                 345                 350

Glu Ala Ser Leu Val Leu Pro Gly Asp Asp Ile Pro Thr Thr Glu Asp
```

```
                           355                 360                 365
Leu Glu Glu Met Leu Asp Asp Ser
       370                 375

(2) INFORMATION FOR SEQ ID NO:90:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:90:

GAGAGACTCG AGGTGATCGA GATCGACCAT GTC                                     33

(2) INFORMATION FOR SEQ ID NO:91:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:91:

AGAGACTCGA GCAATCGGGA AGCGTGACTC A                                       31

(2) INFORMATION FOR SEQ ID NO:92:

(i) SEQUENCE CHARACTERISTICS:
        (A) LENGTH: 323 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:92:

GTCGACTACA AGAAGACTT CAACGACAAC GAGCAGTGGT TCGCCAAGGT CAAGGAGCCG          60

TTGTCGCGCA AGCAGGACAT AGGCGCCGAC CTGGTGATCC CCACCGAGTT CATGGCCGCG        120

CGCGTCAAGG GCCTGGGATG GCTCAATGAG ATCAGCGAAG CCGGCGTGCC CAATCGCAAG        180

AATCTGCGTC AGGACCTGTT GGACTCGAGC ATCGACGAGG GCCGCAAGTT CACCGCGCCG        240

TACATGACCG GCATGGTCGG TCTCGCCTAC AACAAGGCAG CCACCGGACG CGATATCCGC        300

ACCATCGACG ACCTCTGGGA TCC                                               323

(2) INFORMATION FOR SEQ ID NO:93:

(i) SEQUENCE CHARACTERISTICS:
        (A) LENGTH: 1341 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:93:

CCCCACCCCC TTCCCTGGAG CCGACGAAAG GCACCCGCAC ATGTCCCGTG ACATCGATCC         60

CCACCTGCTG GCCGAATGA CCGCACGCCG CACCTTGCGT CGCCGCTTCA TCGGCGGTGG        120

CGCCGCGGCC GCCGCGGGCC TGACCCTCGG TTCGTCGTTC CTGGCGGCGT GCGGGTCCGA        180

CAGTGGGACC TCGAGCACCA CGTCACAGGA CAGCGGCCCC GCCAGCGGCG CCCTGCGCGT        240
```

```
CTCCAACTGG CCGCTCTATA TGGCCGACGG TTTCATCGCA GCGTTCCAGA CCGCCTCGGG      300

CATCACGGTC GACTACAAAG AAGACTTCAA CGACAACGAG CAGTGGTTCG CCAAGGTCAA      360

GGAGCCGTTG TCGCGCAAGC AGGACATAGG CGCCGACCTG GTGATCCCCA CCGAGTTCAT      420

GGCCGCGCGC GTCAAGGGCC TGGGATGGCT CAATGAGATC AGCGAAGCCG GCGTGCCCAA      480

TCGCAAGAAT CTGCGTCAGG ACCTGTTGGA CTCGAGCATC GACGAGGGCC GCAAGTTCAC      540

CGCGCCGTAC ATGACCGGCA TGGTCGGTCT CGCCTACAAC AAGGCAGCCA CCGGACGCGA      600

TATCCGCACC ATCGACGACC TCTGGGATCC CGCGTTCAAG GGCCGCGTCA GTCTGTTCTC      660

CGACGTCCAG GACGGCCTCG GCATGATCAT GCTCTCGCAG GGCAACTCGC CGGAGAATCC      720

GACCACCGAG TCCATTCAGC AGGCGGTCGA TCTGGTCCGC AACAGAACG ACAGGGGGTC       780

AGATCCGTCG CTTCACCGGC AACGACTACG CCGACGACCT GGCCGCAGAA ACATCGCCAT      840

CGCGCAGGCG TACTCCGGTG ACGTCGTGCA GCTGCAGGCG GACAACCCCG ATCTGCAGTT      900

CATCGTTCCC GAATCCGGCG GCGACTGGTT CGTCGACACG ATGGTGATCC CGTACACCAC      960

GCAGAACCAG AAGGCCGCCG AGGCGTGGAT CGACTACATC TACGACCGAG CCAACTACGC     1020

CAAGCTGGTC GCGTTCACCC AGTTCGTGCC CGCACTCTCG GACATGACCG ACGAACTCGC     1080

CAAGGTCGAT CCTGCATCGG CGGAGAACCC GCTGATCAAC CCGTCGGCCG AGGTGCAGGC     1140

GAACCTGAAG TCGTGGGCGG CACTGACCGA CGAGCAGACG CAGGAGTTCA ACACTGCGTA     1200

CGCCGCCGTC ACCGGCGGCT GACGCGGTGG TAGTGCCGAT GCGAGGGGCA TAAATGGCCC     1260

TGCGGACGCG AGGAGCATAA ATGGCCGGTG TCGCCACCAG CAGCCGTCAG CGGACAAGGT     1320

CGCTCCGTAT CTGATGGTCC T                                               1341
```

(2) INFORMATION FOR SEQ ID NO:94:

(i) SEQUENCE CHARACTERISTICS:
        (A) LENGTH: 393 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:94:

```
Met Ser Arg Asp Ile Asp Pro His Leu Leu Ala Arg Met Thr Ala Arg
 1               5                  10                  15

Arg Thr Leu Arg Arg Arg Phe Ile Gly Gly Gly Ala Ala Ala Ala Ala
                20                  25                  30

Gly Leu Thr Leu Gly Ser Ser Phe Leu Ala Ala Cys Gly Ser Asp Ser
            35                  40                  45

Gly Thr Ser Ser Thr Thr Ser Gln Asp Ser Gly Pro Ala Ser Gly Ala
        50                  55                  60

Leu Arg Val Ser Asn Trp Pro Leu Tyr Met Ala Asp Gly Phe Ile Ala
65                  70                  75                  80

Ala Phe Gln Thr Ala Ser Gly Ile Thr Val Asp Tyr Lys Glu Asp Phe
                85                  90                  95

Asn Asp Asn Glu Gln Trp Phe Ala Lys Val Lys Glu Pro Leu Ser Arg
                100                 105                 110

Lys Gln Asp Ile Gly Ala Asp Leu Val Ile Pro Thr Glu Phe Met Ala
            115                 120                 125

Ala Arg Val Lys Gly Leu Gly Trp Leu Asn Glu Ile Ser Glu Ala Gly
        130                 135                 140

Val Pro Asn Arg Lys Asn Leu Arg Gln Asp Leu Leu Asp Ser Ser Ile
```

```
                145                 150                 155                 160
Asp Glu Gly Arg Lys Phe Thr Ala Pro Tyr Met Thr Gly Met Val Gly
                    165                 170                 175
Leu Ala Tyr Asn Lys Ala Ala Thr Gly Arg Asp Ile Arg Thr Ile Asp
                180                 185                 190
Asp Leu Trp Asp Pro Ala Phe Lys Gly Arg Val Ser Leu Phe Ser Asp
                195                 200                 205
Val Gln Asp Gly Leu Gly Met Ile Met Leu Ser Gln Gly Asn Ser Pro
            210                 215                 220
Glu Asn Pro Thr Thr Glu Ser Ile Gln Gln Ala Val Asp Leu Val Arg
225                 230                 235                 240
Glu Gln Asn Asp Arg Gly Ser Asp Pro Ser Leu His Arg Gln Arg Leu
                245                 250                 255
Arg Arg Arg Pro Gly Arg Arg Asn Ile Ala Ile Ala Gln Ala Tyr Ser
                260                 265                 270
Gly Asp Val Val Gln Leu Gln Ala Asp Asn Pro Asp Leu Gln Phe Ile
                275                 280                 285
Val Pro Glu Ser Gly Gly Asp Trp Phe Val Asp Thr Met Val Ile Pro
            290                 295                 300
Tyr Thr Thr Gln Asn Gln Lys Ala Ala Glu Ala Trp Ile Asp Tyr Ile
305                 310                 315                 320
Tyr Asp Arg Ala Asn Tyr Ala Lys Leu Val Ala Phe Thr Gln Phe Val
                325                 330                 335
Pro Ala Leu Ser Asp Met Thr Asp Glu Leu Ala Lys Val Asp Pro Ala
                340                 345                 350
Ser Ala Glu Asn Pro Leu Ile Asn Pro Ser Ala Glu Val Gln Ala Asn
                355                 360                 365
Leu Lys Ser Trp Ala Ala Leu Thr Asp Glu Gln Thr Gln Glu Phe Asn
            370                 375                 380
Thr Ala Tyr Ala Ala Val Thr Gly Gly
385                 390
```

(2) INFORMATION FOR SEQ ID NO:95:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:95:

ATGTCCCGTG ACATCGATCC CC                                  22

(2) INFORMATION FOR SEQ ID NO:96:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:96:

ATCGGCACTA CCACCGCGTC A                                   21

(2) INFORMATION FOR SEQ ID NO:97:

(i) SEQUENCE CHARACTERISTICS:
           (A) LENGTH: 861 base pairs
           (B) TYPE: nucleic acid
           (C) STRANDEDNESS: single
           (D) TOPOLOGY: linear (ii) MOLECULE TYPE: Genomic DNA (xi) SEQUENCE DESCRIPTION: SEQ ID NO:97:

```
GCCGGCGCTC GCATATCTCG CGATCTTCTT CCGTGGTGCC GTTCTTCTCG CTGGCACGCA    60
CCTCGTTGTC GGAGACCGGC GGCTCGGTGT TCATGCCGAC GCTGACGTTC GCCTGGGACT   120
TCGGCAACTA CGTCGACGCG TTCACGATGT ACCACGAGCA GATCTTCCGC TCGTTCGGCT   180
ACGCGTTCGT CGCCACGGTG CTGTGCCTGT TGCTGGCGTT CCCGCTGGCC TACGTCATCG   240
CGTTCAAGGC CGGCCGGTTC AAGAACCTGA TCCTGGGGCT GGTGATCCTG CCGTTCTTCG   300
TCACGTTCCT GATCCGCACC ATTGCGTGGA AGACGATCCT GGCCGACGAA GGCTGGGTGG   360
TCACCGCGCT GGGCGCCATC GGGCTGCTGC CTGACGAGGG CCGGCTGCTG TCCACCAGCT   420
GGGCGGTCAT CGGCGGTCTG ACCTACAACT GGATCATCTT CATGATCCTG CCGCTGTACG   480
TCAGCCTGGA GAAGATCGAC CCGCGTCTGC TGGAGGCCTC CCAGGACCTC TACTCGTCGG   540
CGCCGCGCAG CTTCGGCAAG GTGATCCTGC CGATGGCGAT GCCCGGGGTG CTGGCCGGGA   600
GCATGCTGGT GTTCATCCCG GCCGTCGGCG ACTTCATCAA CGCCGACTAT CTCGGCAGTA   660
CCCAGACCAC CATGATCGGC AACGTGATCC AGAAGCAGTT CCTGGTCGTC AAGGACTATC   720
CGGCGGCGGC CGCGCTGAGT CTGGGGCTGA TGTTGCTGAT CCTGATCGGC GTGCTCCTCT   780
ACACACGGGC GCTGGGTTCG GAGGATCTGG TATGACCACC CAGGCAGGCG CCGCACTGGC   840
CACCGCCGCC CAGCAGGATC C                                             861
```

(2) INFORMATION FOR SEQ ID NO:98:

(i) SEQUENCE CHARACTERISTICS:
           (A) LENGTH: 259 amino acids
           (B) TYPE: amino acid
           (C) STRANDEDNESS: single
           (D) TOPOLOGY: linear (ii) MOLECULE TYPE: protein (xi) SEQUENCE DESCRIPTION: SEQ ID NO:98:

```
Val Val Pro Phe Phe Ser Leu Ala Arg Thr Ser Leu Ser Glu Thr Gly
 1               5                  10                  15

Gly Ser Val Phe Met Pro Thr Leu Thr Phe Ala Trp Asp Phe Gly Asn
             20                  25                  30

Tyr Val Asp Ala Phe Thr Met Tyr His Glu Gln Ile Phe Arg Ser Phe
         35                  40                  45

Gly Tyr Ala Phe Val Ala Thr Val Leu Cys Leu Leu Leu Ala Phe Pro
     50                  55                  60

Leu Ala Tyr Val Ile Ala Phe Lys Ala Gly Arg Phe Lys Asn Leu Ile
65                  70                  75                  80

Leu Gly Leu Val Ile Leu Pro Phe Phe Val Thr Phe Leu Ile Arg Thr
                 85                  90                  95

Ile Ala Trp Thr Ile Leu Ala Asp Glu Gly Trp Val Val Thr Ala Leu
            100                 105                 110

Gly Ala Ile Gly Leu Leu Pro Asp Glu Gly Arg Leu Leu Ser Thr Ser
        115                 120                 125

Trp Ala Val Ile Gly Gly Leu Thr Tyr Asn Trp Ile Ile Phe Met Ile
    130                 135                 140
```

```
Leu Pro Leu Tyr Val Ser Leu Glu Lys Ile Asp Pro Arg Leu Leu Glu
145                 150                 155                 160

Ala Ser Gln Asp Leu Tyr Ser Ser Ala Pro Arg Ser Phe Gly Lys Val
            165                 170                 175

Ile Leu Pro Met Ala Met Pro Gly Val Leu Ala Gly Ser Met Leu Val
            180                 185                 190

Phe Ile Pro Ala Val Gly Asp Phe Ile Asn Ala Asp Tyr Leu Gly Ser
            195                 200                 205

Thr Gln Thr Thr Met Ile Gly Asn Val Ile Gln Lys Gln Phe Leu Val
            210                 215                 220

Val Lys Asp Tyr Pro Ala Ala Ala Leu Ser Leu Gly Leu Met Leu
225                 230                 235                 240

Leu Ile Leu Ile Gly Val Leu Tyr Thr Arg Ala Leu Gly Ser Glu
            245                 250                 255

Asp Leu Val
```

(2) INFORMATION FOR SEQ ID NO:99:

(i) SEQUENCE CHARACTERISTICS:
        (A) LENGTH: 277 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:99:

```
GTAATCTTTG CTGGAGCCCG TACGCCGGTA GGCAAACTCA TGGGTTCGCT CAAGGACTTC      60

AAGGGCAGCG ATCTCGGTGC CGTGGCGATC AAGGGCGCCC TGGAGAAAGC CTTCCCCGGC     120

GTCGACGACC CTGCTCGTCT CGTCGAGTAC GTGATCATGG GCCAAGTGCT CTCCGCCGGC     180

GCCGGCCAGA TGCCCGCCCG CCAGGCCGCC GTCGCCGCCG GCATCCCGTG GGACGTCGCC     240

TCGCTGACGA TCAACAAGAT GTGCCTGTCG GGCATCG                              277
```

(2) INFORMATION FOR SEQ ID NO:100:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:100:

```
Val Ile Phe Ala Gly Ala Arg Thr Pro Val Gly Lys Leu Met Gly Ser
1               5                  10                  15

Leu Lys Asp Phe Lys Gly Ser Asp Leu Gly Ala Val Ala Ile Lys Gly
            20                  25                  30

Ala Leu Glu Lys Ala Phe Pro Gly Val Asp Asp Pro Ala Arg Leu Val
            35                  40                  45

Glu Tyr Val Ile Met Gly Gln Val Leu Ser Ala Gly Ala Gly Gln Met
            50                  55                  60

Pro Ala Arg Gln Ala Ala Val Ala Ala Gly Ile Pro Trp Asp Val Ala
65                  70                  75                  80

Ser Leu Thr Ile Asn Lys Met Cys Leu Ser Gly Ile
            85                  90
```

(2) INFORMATION FOR SEQ ID NO:101:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Other
        (B) LOCATION: 1...1
        (D) OTHER INFORMATION: Residue can be either Glu or Pro (A) NAME/KEY: Other
        (B) LOCATION: 2...2
        (D) OTHER INFORMATION: Residue can be either Pro or Glu (xi) SEQUENCE DESCRIPTION: SEQ ID NO:101:

Xaa Xaa Ala Asp Arg Gly Xaa Ser Lys Tyr Arg Xaa
1               5                   10

(2) INFORMATION FOR SEQ ID NO:102:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:102:

Xaa Ile Asp Glu Ser Leu Phe Asp Ala Glu Glu Lys Met Glu Lys Ala
1               5                   10                  15

Val Ser Val Ala Arg Asp Ser Ala
            20

(2) INFORMATION FOR SEQ ID NO:103:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:103:

Xaa Xaa Ile Ala Pro Ala Thr Ser Gly Thr Leu Ser Glu Phe Xaa Ala
1               5                   10                  15

Xaa Lys Gly Val Thr Met Glu
            20

(2) INFORMATION FOR SEQ ID NO:104:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:104:

Pro Asn Val Pro Asp Ala Phe Ala Val Leu Ala Asp Arg Val Gly
1               5                   10                  15

(2) INFORMATION FOR SEQ ID NO:105:

(i) SEQUENCE CHARACTERISTICS:

```
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:105:

Xaa Ile Arg Val Gly Val Asn Gly Phe
 1               5

(2) INFORMATION FOR SEQ ID NO:106:

(i) SEQUENCE CHARACTERISTICS:
        (A) LENGTH: 485 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:106:

AGCGGCTGGG ACATCAACAC CGCCGCCTTC GAGTGGTACG TCGACTCGGG TCTCGCGGTG      60

ATCATGCCCG TCGGCGGGCA GTCCAGCTTC TACAGCGACT GGTACAGCCC GGCCTGCGGT     120

AAGGCCGGCT GCCAGACCTA CAAGTGGGAG ACGTTCCTGA CCCAGGAGCT GCCGGCCTAC     180

CTCGCCGCCA ACAAGGGGGT CGACCCGAAC CGCAACGCGG CCGTCGGTCT GTCCATGGCC     240

GGTTCGGCGG CGCTGACGCT GGCGATCTAC CACCCGCAGC AGTTCCAGTA CGCCGGGTCG     300

CTGTCGGGCT ACCTGAACCC GTCCGAGGGG TGGTGGCCGA TGCTGATCAA CATCTCGATG     360

GGTGACGCGG GCGGCTACAA GGCCAACGAC ATGTGGGGTC GCACCGAGGA CCCGAGCAGC     420

GCCTGGAAGC GCAACGACCC GATGGTCAAC ATCGGCAAGC TGGTCGCCAA CAACACCCCC     480

CTCTC                                                                485
```